US007459153B2

(12) United States Patent
Wadell et al.

(10) Patent No.: US 7,459,153 B2
(45) Date of Patent: Dec. 2, 2008

(54) VIRAL VECTORS FOR GENE THERAPY

(76) Inventors: Göran Wadell, Slädvägen 4, S-903 39 Umeå (SE); Ya-fang Mei, Gluntens väg 8, S-907 37 Umeå (SE); Anna Segerman, Rullstensgatan 21, S-906 55 Umeå (SE); Johan Skog, Historiegränd 4C, S-907 34 Umeå (SE); Kristina Lindman, Blåbärsvägen 50, S-903 39 Umeå (SE)

( * ) Notice: Subject to any disclaimer, the term of this patent is extended or adjusted under 35 U.S.C. 154(b) by 677 days.

(21) Appl. No.: 10/250,304

(22) PCT Filed: Jan. 4, 2002

(86) PCT No.: PCT/SE02/00013

§ 371 (c)(1), (2), (4) Date: Jan. 23, 2004

(87) PCT Pub. No.: WO02/053759

PCT Pub. Date: Jul. 11, 2002

(65) Prior Publication Data

US 2004/0136958 A1 Jul. 15, 2004

Related U.S. Application Data

(60) Provisional application No. 60/260,358, filed on Jan. 8, 2001.

(30) Foreign Application Priority Data

Jan. 4, 2001 (SE) .................................. 0100035

(51) Int. Cl.
*C12N 15/63* (2006.01)
*C12N 15/861* (2006.01)
*C07H 21/00* (2006.01)
*C07H 21/04* (2006.01)
*A61K 48/00* (2006.01)
*C07K 14/00* (2006.01)
*C07K 14/075* (2006.01)

(52) U.S. Cl. .................... 424/93.2; 424/93.1; 424/93.6; 435/320.1; 536/23.1; 536/23.7; 536/23.72

(58) Field of Classification Search ...................... None
See application file for complete search history.

(56) References Cited

U.S. PATENT DOCUMENTS 6,054,467 A * 4/2000 Gjerset ....................... 514/309
6,524,572 B1 * 2/2003 Li .............................. 424/93.2
6,555,367 B1 * 4/2003 Spence et al. ............ 435/320.1

FOREIGN PATENT DOCUMENTS

EP       1 054 064 A1    11/2000

OTHER PUBLICATIONS

Stone et al., J. Virol., 2005, vol. 79, No. 8, pp. 5090-5104.*
Current Biology Ltd., Bramson et al., "The use of adenoviral vectors for gene therapy and gene transfer in vivo", pp. 590-595, 1995.
Journal of Virology, Segerman et al, "Adenovirus Types 11p and 35p Show HIgh Binding Efficiencies for Committed Hematopoietic Cell Lines and Are infective to These Cell Lines", pp. 1457-1467, 1999.
Journal of General Virology, W.C. Russell, "Update on adenovirus and its vectors", pp. 2573-2604, 2000.

* cited by examiner

*Primary Examiner*—David Guzo
(74) *Attorney, Agent, or Firm*—Young & Thompson

(57) ABSTRACT

Adenovirus types 11p and 4p show a higher binding affinity and infectivity than type 5 for endothelial and carcinoma cell lines. Adenovirus type 11p shows a stronger binding to cells for neural origin, such as glioblastoma, neuroblastoma and medulloblastoma. The fact that adenovirus type 11 has a comparatively low prevalence in society, together with its high affinity and infectivity, makes it very suitable for use in gene therapy.

15 Claims, 8 Drawing Sheets

SEQUENCE LISTING

<160> NUMBER OF SEQ ID NOS: 2

<210> SEQ ID NO 1

<211> LENGTH: 34793
<212> TYPE: DNA
<213> ORGANISM: Adenovirus serotype 11

<400> SEQUENCE: 1

```
catcatcaat aatatacctt atagatggaa tggtgccaat atgtaaatga ggtgatttta      60
aaaagtgtgg atcgtgtggt gattggctgt ggggttaacg gctaaaaggg gcggtgcgac     120
cgtgggaaaa tgacgttttg tgggggtgga gttttttttgc aagttgtcgc gggaaatgtg    180
acgcataaaa aggcttttttt ctcacggaac tacttagttt tcccacggta tttaacagga    240
aatgaggtag ttttgaccgg atgcaagtga aaattgttga ttttcgcgcg aaaactgaat     300
gaggaagtgt ttttctgaat aatgtggtat ttatggcagg gtggagtatt tgttcagggc     360
caggtagact ttgacccatt acgtggaggt ttcgattacc gtgttttttta cctgaatttc    420
cgcgtaccgt gtcaaagtct tctgttttta cgtaggtgtc agctgatcgc tagggtattt     480
atacctcagg gtttgtgtca agaggccact cttgagtgcc agcgagaaga gttttctcct    540
ctgcgccggc agtttaataa taaaaaaatg agagatttgc gatttctgcc tcaggaaata    600
atctctgctg agactggaaa tgaaatattg gagcttgtgg tgcacgccct gatgggagac    660
gatccggagc cacctgtgca gcttttttgag cctcctacgc ttcaggaact gtatgattta    720
gaggtagagat gatcggagga ttctaatgag gaagctgtaa atggcttttt taccgattct    780
atgcttttag ctgctaatga agggttagaa ttagatccgc cttttggacac ttttgatact    840
ccaggggtaa ttgtggaaag cggtacaggt gtaagaaaat tacctgattt gagttccgtg    900
gactgtgatt tgcactgcta tgaagacggg tttcctccga gtgatgagga ggaccatgaa    960
aaggagcagt ccatgcagac tgcagcgggt gagggagtga aggctgccaa tgttggtttt   1020
cagttggatt gcccggagct tcctggacat ggctgtaagt cttgtgaatt tcacaggaaa   1080
aatactggag taaggaact gttatgttcg ctttgttata tgagaacgca ctgccacttt    1140
atttacagta agtgtgttta agttaaaatt taaaggaata tgctgttttt cacatgtata   1200
ttgagtgtga gttttgtgct tcttattata ggtcctgtgt ctgatgctga tgaatcacca   1260
tctcctgatt ctactaccctc acctcctgag attcaagcac ctgttcctgt ggacgtgcgc   1320
aagcccattc ctgtgaagct taagcctggg aaacgtccag cagtggaaaa acttgaggac   1380
ttgttacagg gtggggacgg acctttggac ttgagtacac ggaaacgtcc aagacaataa    1440
gtgttccata tccgtgttta cttaaggtga cgtcaatatt tgtgtgacag tgcaatgtaa   1500
taaaaatatg ttaactgttc actggttttt attgcttttt gggcggggac tcaggtatat   1560
aagtagaagc agacctgtgt ggttagctca taggagctgg ctttcatcca tggaggtttg   1620
ggccattttg gaagacctta ggaagactag gcaactgtta gagaacgctt cggacggagt   1680
ctccggtttt tggagattct ggttcgctag tgaattagct agggtagttt ttaggataaa   1740
acaggactat aaacaagaat tgaaaagtt gttggtagat tgcccaggac ttttttgaagc    1800
tcttaatttg ggccatcagg ttcactttaa agaaaaagtt ttatcagttt tagacttttc    1860
aaccccaggt agaactgctg ctgctgtggc ttttcttact tttatattag ataaatggat   1920
cccgcagact catttcagca ggggatacgt tttggatttc atagccacag cattgtggag    1980
aacatggaag gttcgcaaga tgaggacaat cttaggttac tggccagtgc agcctttggg    2040
tgtagcggga atcctgaggc atccaccggt catgccagcg gttctggagg aggaacagca    2100
agaggacaac ccgagagccg gcctggaccc tccagtggag gaggcggagt agctgacttg    2160
tctcctgaac tgcaacgggt gcttactgga tctacgtcca ctggacggga taggggcgtt   2220
```

```
aagagggaga  gggcatctag  tggtactgat  gctagatctg  agttggcttt  aagtttaatg   2280
agtcgcagac  gtcctgaaac  catttggtgg  catgaggttc  agaaagaggg  aagggatgaa   2340
gtttctgtat  tgcaggagaa  atattcactg  aacaggtga   aaacatgttg  gttggagcct   2400
gaggatgatt  gggaggtggc  cattaaaaat  tatgccaaga  tagctttgag  gcctgataaa   2460
cagtataaga  ttactagacg  gattaatatc  cggaatgctt  gttacatatc  tggaaatggg   2520
gctgaggtgg  taatagatac  tcaagacaag  gcagttatta  gatgctgcat  gatggatatg   2580
tggcctgggg  tagtcggtat  ggaagcagta  acttttgtaa  atgttaagtt  taggggagat   2640
ggttataatg  gaatagtgtt  tatggccaat  accaaactta  tattgcatgg  ttgtagcttt   2700
tttggtttca  acaatacctg  tgtagatgcc  tggggacagg  ttagtgtacg  ggatgtagt    2760 ttctatgcgt  gttggattgc  cacagctggc  agaaccaaga  gtcaattgtc  tctgaagaaa   2820
tgcatatttc  aaagatgtaa  cctgggcatt  ctgaatgaag  gcgaagcaag  ggtccgccac   2880
tgcgcttcta  cagatactgg  atgttttatt  ttgattaagg  gaaatgccag  cgtaaagcat   2940
aacatgattt  gcggtgcttc  cgatgagagg  ccttatcaaa  tgctcacttg  tgctggtggg   3000
cattgtaata  tgctggctac  tgtgcatatt  gtttcccatc  aacgcaaaaa  atggcctgtt   3060
tttgatcaca  atgtgatgac  gaagtgtacc  atgcatgcag  gtgggcgtag  aggaatgttt   3120
atgccttacc  agtgtaacat  gaatcatgtg  aaagtgttgt  tggaaccaga  tgccttttcc   3180
agaatgagcc  taacaggaat  ttttgacatg  aacatgcaaa  tctggaagat  cctgaggtat   3240
gatgatacga  gatcgagggt  acgcgcatgc  gaatgcggag  gcaagcatgc  caggttccag   3300
ccggtgtgtg  tagatgtgac  tgaagatctc  agaccggatc  atttggttat  tgcccgcact   3360
ggagcagagt  tcggatccag  tggagaagaa  actgactaag  gtgagtattg  gaaaactttt   3420
ggggtgggat  tttcagatgg  acagattgag  taaaaatttg  tttttctgt   cttgcagctg   3480 tcatgagtgg  aaacgcttct  tttaaggggg  gagtcttcag  cccttatctg  acagggcgtc   3540
tcccatcctg  ggcaggagtt  cgtcagaatg  ttatgggatc  tactgtggat  ggaagacccg   3600
tccaacccgc  caattcttca  acgctgacct  atgctacttt  aagttcttca  cctttggacg   3660
cagctgcagc  tgccgccgcc  gcttctgttg  ccgctaacac  tgtgcttgga  atgggttact   3720
atggaagcat  catggctaat  tccacttcct  ctaataaccc  ttctaccctg  actcaggaca   3780
agttacttgt  ccttttggcc  cagctggagg  ctttgaccca  acgtctgggt  gaactttctc   3840
agcaggtggt  cgagttgcga  gtacaaactg  agtctgctgt  cggcacggca  aagtctaaat   3900
aaaaaaatcc  cagaatcaat  gaataaataa  acaagcttgt  tgttgattta  aaatcaagtg   3960
tttttatttc  atttttcgcg  cacggtatgc  cctagaccac  cgatctctat  cattgagaac   4020
tcggtggatt  ttttccagga  tcctatagag  gtgggattga  atgtttagat  acatgggcat   4080
taggccgtct  ttggggtgga  gatagctcca  ttgaagggat  tcatgctccg  ggtagtgtt   4140 gtaaatcacc  cagtcataac  aaggtcgcag  tgcatggtgt  tgcacaatat  cttttagaag   4200
taggctgatt  gccacagata  agcccttggt  gtaggtgttt  acaaaccggt  tgagctggga   4260
tgggtgcatt  cggggtgaaa  ttatgtgcat  tttggattgg  attttttaagt  tggcaatatt  4320 gccgccaaga  tcccgtcttg  ggttcatgtt  atgaaggacc  accaagacgg  tgtatccggt   4380
acatttagga  aatttatcgt  gcagcttgga  tggaaaagcg  tggaaaaatt  tggagacacc   4440
cttgtgtcct  ccaagatttt  ccatgcactc  atccatgata  atagcaatgg  ggccgtgggc   4500
agcggcgcgg  gcaaacacgt  tccgtgggtc  tgacacatca  tagttatgtt  cctgagttaa   4560
```

```
atcatcataa gccatttttaa tgaatttggg gcggagagta ccagattggg gtatgaatgt    4620
tccttcgggc cccggagcat agttcccctc acagatttgc atttcccaag ctttcagttc    4680
cgagggtgga atcatgtcca cctgggggc tatgaaaaac accgtttctg ggcgggggt     4740 gattaattgt gatgatagca aatttctgag caattgagat ttgccacatc cggtggggcc    4800
ataaatgatt ccgattacgg gttgcaggtg gtagtttagg gaacggcaac tgccgtcttc    4860
tcgaagcaag ggggccacct cgttcatcat ttcccttaca tgcatatttt cccgcaccaa    4920
atccattagg aggcgctctc ctcctagtga tagaagttct tgtagtgagg aaaagttttt    4980
cagcggtttc agaccgtcag ccatgggcat tttggagaga gtttgctgca aaagttctag    5040
tctgttccac agttcagtga tgtgttctat ggcatctcga tccagcagac ctcctcgttt    5100
cgcgggtttg gacggctcct ggaatagggt atgagacgat gggcgtccag cgctgccagg    5160
gttcggtcct tccagggtct cagtgttcga gtcaggttg tttccgtcac agtgaagggg    5220
tgtgcgcctg cttgggcgct tgccagggtg cgcttcagac tcatcctgct ggtcgaaaac    5280
ttctgtcgct tggcgccctg tatgtcggcc aagtagcagt ttaccatgag ttcgtagttg    5340
agcgcctcgg ctgcgtggcc tttggcgcgg agcttacctt tggaagtttt cttgcatacc    5400
gggcagtata ggcatttcag cgcatacaac ttgggcgcaa ggaaaacgga ttctggggag    5460
tatgcatctg cgccgcagga ggcgcaaaca gtttcacatt ccaccagcca ggttaaatcc    5520
ggttcattgg ggtcaaaaac aagttttccg ccatattttt tgatgcgttt cttacctttg    5580
gtctccatga gttcgtgtcc tcgttgagtg acaaacaggc tgtccgtgtc cccgtagact    5640
gattttacag gcctcttctc cagtggagtg cctcggtctt cttcgtacag gaactctgac    5700
cactctgata caaaggcgcg cgtccaggcc agcacaaagg aggctatgtg ggaggggtag    5760
cgatcgttgt caaccagggg gtccacccttt tccaaagtat gcaaacacat gtcaccctct    5820
tcaacatcca ggaatgtgat tggcttgtag gtgtatttca cgtgacctgg ggtccccgct    5880
gggggggtat aaaaggggc ggttctttgc tcttcctcac tgtcttccgg atcgctgtcc    5940
aggaacgtca gctgttgggg taggtattcc ctctcgaagg cgggcatgac ctctgcactc    6000
aggttgtcag tttctaagaa cgaggaggat ttgatattga cagtgccggt tgagatgcct    6060
ttcatgaggt tttcgtccat ttggtcagaa aacacaattt ttttattgtc aagtttggtg    6120
gcaaatgatc catacagggc gttggataaa agtttggcaa tggatcgcat ggtttggttc    6180
ttttccttgt ccgcgcgctc tttgcggcg atgttgagtt ggacatactc gcgtgccagg    6240
cacttccatt cggggaagat agttgttaat tcatctggca cgattctcac ttgccaccct    6300
cgattatgca aggtaattaa atccacactg gtggccacct cgcctcgaag gggttcattg    6360
gtccaacaga gcctacctcc tttcctagaa cagaaagggg gaagtgggtc tagcataagt    6420
tcatcgggag ggtctgcatc catggtaaag attcccggaa gtaaatcctt atcaaaatag    6480
ctgatgggag tggggtcatc taaggccatt tgccattctc gagctgccag tgcgcgctca    6540
tatgggttaa ggggactgcc ccatggcatg ggatgggtga gtgcagaggc atacatgcca    6600
cagatgtcat agacgtagat gggatcctca aagatgccta tgtaggttgg atagcatcgc    6660 cccctctga tacttgctcg cacatagtca tatagttcat gtgatggcgc tagcagcccc    6720
ggacccaagt tggtgcgatt gggttttct gttctgtaga cgatctggcg aaagatggcg    6780
tgagaattgg aagagatggt gggtctttga aaaatgttga aatgggcatg aggtagacct    6840
acagagtctc tgcaaaagtg ggcataagat tcttgaagct tggttaccag ttcggcggtg    6900
acaagtacgt ctagggcgca gtagtcaagt gtttcttgaa tgatgtcata acctggttgg    6960
```

```
tttttcttttt cccacagttc gcggttgaga aggtattctt cgcgatcctt ccagtactct   7020
tctagcggaa acccgtcttt gtctgcacgg taagatccta gcatgtagaa ctgattaact   7080
gccttgtaag ggcagcagcc cttctctacg ggtagagagt atgcttgagc agcttttcgt   7140
agcgaagcgt gagtaagggc aaaggtgtct ctgaccatga ctttgagaaa ttggtatttg   7200
aagtcgatgt cgtcacaggc tccctgttcc cagagttgga agtctacccg tttcttgtag   7260
gcggggttgg gcaaagcgaa agtaacatca ttgaagagaa tcttaccggc tctgggcata   7320
aaattgcgag tgatgcgaaa aggctgtggt acttccgctc gattgttgat cacctgggca   7380
gctaggacga tctcgtcgaa accgttgatg ttgtgtccta cgatgtataa ttctatgaaa   7440
cgcggcgtgc ctctgacgtg aggtagctta ctgagctcat caaaggttag gtctgtgggg   7500
tcagataagg cgtagtgttc gagagcccat tcgtgcaggt gaggatttgc atgtaggaat   7560
gatgaccaaa gatctaccgc cagtgctgtt tgtaactggt cccgatactg acgaaaatgc   7620
cggccaattg ccattttttc tggagtgaca cagtagaagg ttctggggtc ttgttgccat   7680
cgatcccact tgagtttaat ggctagatcg tgggccatgt tgacgagacg ctcttctcct   7740
gagagtttca tgaccagcat gaaaggaact agttgtttgc caaaggatcc catccaggtg   7800 taagttttcca catcgtaggt caggaagagt cttttctgtgc gaggatgaga gccgatcggg   7860
aagaactgga tttcctgcca ccagttggag gattggctgt tgatgtgatg aagtagaag    7920 tttctgcggc gcgccgagca ttcgtgtttg tgcttgtaca gacggccgca gtagtcgcag   7980
cgttgcacgg gttgtatctc gtgaatgagt tgtacctggc ttcccttgac gagaaatttc   8040
agtgggaagc cgaggcctgg cgattgtatc tcgtgctctt ctatattcgc tgtatcggcc   8100
tgttcatctt ctgtttcgat ggtggtcatg ctgacgagcc cccgcgggag gcaagtccag   8160
acctcggcgc gggaggggcg gagctgaagg acgagagcgc gcaggctgga gctgtccaga   8220
gtcctgagac gctgcggact caggttagta ggtaggaca gaaagattaac ttgcatgatc   8280 ttttccaggg cgtgcgggag gttcagatgg tacttgattt ccacaggttc gtttgtagag   8340
acgtcaatgg cttgcagggt tccgtgtcct ttgggcgcca ctaccgtacc tttgtttttt   8400
cttttgatcg gtggtggctc tcttgcttct tgcatgctca gaagcggtga cggggacgcg   8460
cgccgggcgg cagcggttgt tccggacccg agggcatggc tggtagtggc acgtcggcgc   8520
cgcgcacggg caggttctgg tactgcgctc tgagaagact tgcgtgcgcc accacgcgtc   8580
gattgacgtc ttgtatctga cgtctctggg tgaaagctac cggccccgtg agcttgaacc   8640
tgaaagagag ttcaacagaa tcaatttcgg tatcgttaac ggcagcttgt ctcagtatt    8700 cttgtacgtc accagagttg tcctggtagg cgatctccgc catgaactgc tcgatttctt   8760
cctcctgaag atctccgcga cccgctcttt cgacggtggc cgcgaggtca ttggagatac   8820
ggcccatgag ttgggagaat gcattcatgc ccgcctcgtt ccagacgcgg ctgtaaacca   8880 cggcccccctc ggagtctctt gcgcgcatca ccacctgagc gaggttaagc tccacgtgtc   8940
tggtgaagac cgcatagttg cataggcgct gaaaaaggta gttgagtgtg gtggcaatgt   9000
gttcggcgac gaagaaatac atgatccatc gtctcagcgg catttcgcta acatcgccca   9060
gagcttccaa gcgctccatg gcctcgtaga agtccacggc aaaattaaaa aactgggagt   9120
ttcgcgcgga cacggtcaat tcctcctcga aagacggat gagttcggct atggtggccc    9180
gtacttcgcg ttcgaaggct cccgggatct cttcttcctc ttctatctct tcttccacta   9240
acatctcttc ttcgtcttca ggcgggggcg gagggggcac gcggcgacgt cgacggcgca   9300
```

```
cgggcaaacg gtcgatgaat cgttcaatga cctctccgcg gcggcggcgc atggtttcag    9360
tgacggcgcg gccgttctcg cgcggtcgca gagtaaaaac accgccgcgc atctccttaa    9420
agtggtgact gggaggttct ccgtttggga gggagagggc gctgattata cattttatta    9480
attggcccgt agggactgca cgcagagatc tgatcgtgtc aagatccacg ggatctgaaa    9540
acctttcgac gaaagcgtct aaccagtcac agtcacaagg taggctgagt acggcttctt    9600
gtgggcgggg gtggttatgt gttcggtctg ggtcttctgt ttcttcttca tctcgggaag    9660
gtgagacgat gctgctggtg atgaaattaa agtaggcagt tctaagacgg cggatggtgg    9720
cgaggagcac caggtctttg ggtccggctt gctggatacg caggcgattg gccattcccc    9780
aagcattatc ctgacatcta gcaagatctt tgtagtagtc ttgcatgagc cgttctacgg    9840
gcacttcttc ctcacccgtt ctgccatgca tacgtgtgag tccaaatccg cgcattggtt    9900
gtaccagtgc caagtcagct acgactcttt cggcgaggat ggcttgctgt acttgggtaa    9960
gggtggcttc aaagtcatca aaatccacaa agcggtggta agctcctgta ttaatggtgt   10020
aagcacagtt ggccatgact gaccagttaa ctgtctggtg accagggcgc acgagctcgg   10080
tgtatttaag gcgcgaatag gcgcgggtgt caaagatgta atcgttgcag gtgcgcacca   10140
gatactggta ccctataaga aaatgcggcg gtggttggcg gtagagaggc catcgttctg   10200
tagctggagc gccaggggcg aggtcttcca acataaggcg gtgatagccg tagatgtacc   10260
tggacatcca ggtgattcct gcggcggtag tagaagcccg aggaaactcg cgtacgcggt   10320
tccaaatgtt gcgtagcggc atgaagtagt tcattgtagg cacggtttga ccagtgaggc   10380
gcgcgcagtc attgatgctc tatagacacg gagaaaatga aagcgttcag cgactcgact   10440
ccgtagcctg gaggaacgtg aacgggttgg gtcgcggtgt accccggttc gagacttgta   10500
ctcgagccgg ccggagccgc ggctaacgtg gtattggcac tcccgtctcg acccagccta   10560
caaaaatcca ggatacggaa tcgagtcgtt ttgctggttt ccgaatggca gggaagtgag   10620
tcctattttt ttttttttgc cgctcagatg catcccgtgc tgcgacagat gcgcccccaa   10680
caacagcccc cctcgcagca gcagcagcag caatcacaaa aggctgtccc tgcaactact   10740
gcaactgccg ccgtgagcgg tgcggacagc ccgcctatga tctggacttg gaagagggcg   10800
aaggactggc acgtctaggt gcgccttcac ccgagcggca tccgcgagtt caactgaaaa   10860
aagattctcg cgaggcgtat gtgccccaac agaacctatt tagagacaga agcggcgagg   10920
agccggagga gatgcgagct tcccgcttta acgcgggtcg tgagctgcgt cacggtttgg   10980
accgaagacg agtgttgcgg gacgaggatt tcgaagttga tgaaatgaca gggatcagtc   11040
ctgccagggc acacgtggct gcagccaacc ttgtatcggc ttacgagcag acagtaaagg   11100
aagagcgtaa cttccaaaag tcttttaata atcatgtgcg aaccctgatt gcccgcgaag   11160
aagttaccct tggtttgatg catttgtggg atttgatgga agctatcatt cagaacccta   11220
ctagcaaacc tctgaccgcc cagctgtttc tggtggtgca acacagcaga acaatgagg    11280 ctttcagaga ggcgctgctg aacatcaccg aacccgaggg gagatggttg tatgatctta   11340
tcaacattct acagagtatc atagtgcagg agcggagcct gggcctggcc gagaaggtgg   11400
ctgccatcaa ttactcggtt ttgagcttgg gaaaatatta cgctcgcaaa atctacaaga   11460
ctccatacgt tccatagac aaggaggtga agatagatgg gttctacatg cgcatgacgc    11520
tcaaggtctt gaccctgagc gatgatcttg gggtgtatcg caatgacaga atgcatcgcg   11580
cggttagcgc cagcaggagg cgcgagttaa gcgacaggga actgatgcac agtttgcaaa   11640
gagctctgac tggagctgga accgagggtg agaattactt cgacatggga gctgacttgc   11700
```

```
agtggcagcc tagtcgcagg gctctgagcg ccgcgacggc aggatgtgag cttccttaca   11760
tagaagaggc ggatgaaggc gaggaggaag agggcgagta cttggaagac tgatggcaca   11820
acccgtgttt tttgctagat ggaacagcaa gcaccggatc ccgcaatgcg ggcggcgctg   11880
cagagccagc cgtccggcat taactcctcg gacgattgga cccaggccat gcaacgtatc   11940
atggcgttga cgactcgcaa ccccgaagcc tttagacagc aaccccaggc caaccgtcta   12000
tcggccatca tggaagctgt agtgccttcc cgctctaatc ccactcatga aaggtcctg    12060
gccatcgtga acgcgttggt ggagaacaaa gctattcgtc cagatgaggc cggactggta   12120
tacaacgctc tcttagaacg cgtggctcgc tacaacagta gcaatgtgca aaccaatttg   12180
gaccgtatga taacagatgt acgcgaagcc gtgtctcagc gcgaaaggtt ccagcgtgat   12240
gccaacctgg gttcgctggt ggcgttaaat gctttcttga gtactcagcc tgctaatgtg   12300
ccgcgtggtc aacaggatta tactaacttt ttaagtgctt tgagactgat ggtatcagaa   12360
gtacctcaga gcgaagtgta tcagtccggt cctgattact tctttcagac tagcagacag   12420
ggcttgcaga cggtaaatct gagccaagct tttaaaaacc ttaaaggttt gtggggagtg   12480
catgccccgg taggagaaag agcaaccgtg tctagcttgt taactccgaa ctcccgccta   12540
ttattactgt tggtagctcc tttcaccgac agcggtagca tcgaccgtaa ttcctatttg   12600
ggttacctac taaacctgta tcgcgaagcc atagggcaaa gtcaggtgga cgagcagacc   12660
tatcaagaaa ttacccaagt cagtcgcgct ttgggacagg aagacactgg cagtttggaa   12720
gccactctga acttcttgct taccaatcgg tctcaaaaga tccctcctca atatgctctt   12780
actgcggagg aggagaggat ccttagatat gtgcagcaga gcgtgggatt gtttctgatg   12840
caagaggggg caactccgac tgcagcactg gacatgacag cgcgaaatat ggagcccagc   12900
atgtatgcca gtaaccgacc tttcattaac aaactgctgg actacttgca cagagctgcc   12960
gctatgaact ctgattattt caccaatgcc atcttaaacc cgcactggct gcccccacct   13020
ggtttctaca cgggcgaata tgacatgccc gaccctaatg acggatttct gtgggacgac   13080
gtggacagcg atgttttttc acctctttct gatcatcgca cgtggaaaaa ggaaggcggc   13140
gatagaatgc attcttctgc atcgctgtcc ggggtcatgg gtgctaccgc ggctgagccc   13200
gagtctgcaa gtccttttcc tagtctaccc ttttctctac acagtgtacg tagcagcgaa   13260
gtgggtagaa taagtcgccc gagtttaatg ggcgaagagg agtatctaaa cgattccttg   13320
ctcagaccgg caagagaaaa aaatttccca aacaatggaa tagaaagttt ggtggataaa   13380
atgagtagat ggaagactta tgctcaggat cacagagacg agcctgggat catggggatt   13440
acaagtagag cgagccgtag acgccagcgc catgacagac agagggtct tgtgtgggac    13500
gatgaggatt cggccgatga tagcagcgtg ctggacttgg gtgggagagg aaggggcaac   13560
ccgtttgctc atttgcgccc tcgcttgggt ggtatgttgt aaaaaaaaat aaaaaaaaaa   13620
ctcaccaagg ccatggcgac gagcgtacgt tcgttcttct ttattatctg tgtctagtat   13680
aatgaggcga tcgtgctag gcggagcggt ggtgtatccg gagggtcctc ctccttcgta    13740
cgagagcgtg atgcagcagc agcaggcgac ggcggtgatg caatcccac tggaggctcc    13800
ctttgtgcct ccgcgatacc tggcacctac ggagggcaga acagcattc gttattcgga    13860
actggcacct cagtacgata ccaccaggtt gtatctggtg acaacaagt cggcggacat    13920
tgcttctctg aactatcaga atgaccacag caacttcttg accacggtgg tgcaaaacaa   13980
tgactttacc cctacggaag ccagcaccca gaccattaac tttgatgaac gatcgcggtg   14040
```

```
gggcggtcag ctaaagacca tcatgcatac taacatgcca aacgtgaacg agtatatgtt   14100
tagtaacaag ttcaaagcgc gtgtgatggt gtccagaaaa cctcccgacg gtgctgcagt   14160 tgggatact  tatgatcaca agcaggatat tttgaaatat gagtggttcg agtttacttt   14220
gccagaaggc aacttttcag ttactatgac tattgatttg atgaacaatg ccatcataga   14280
taattacttg aaagtgggta gacagaatgg agtgcttgaa agtgacattg gtgttaagtt   14340
cgacaccagg aacttcaagc tgggatggga tcccgaaacc aagttgatca tgcctggagt   14400
gtatacgtat gaagccttcc atcctgacat tgtcttactg cctggctgcg gagtggattt   14460
taccgagagt cgtttgagca accttcttgg tatcagaaaa aaacagccat ttcaagaggg   14520
ttttaagatt ttgtatgaag atttagaagg tggtaatatt ccggccctct ggatgtaga    14580 tgcctatgag aacagtaaga aagaacaaaa agccaaaata gaagctgcta cagctgctgc   14640
agaagctaag gcaaacatag ttgccagcga ctctacaagg gttgctaacg ctggagaggt   14700
cagaggagac aattttgcgc caacacctgt tccgactgca gaatcattat tggccgatgt   14760
gtctgaagga acggacgtga aactcactat tcaacctgta gaaaaagata gtaagaatag   14820
aagctataat gtgttggaag acaaaatcaa cacagcctat cgcagttggt atctttcgta   14880
caattatggc gatcccgaaa aaggagtgcg ttcctggaca ttgctcacca cctcagatgt   14940
cacctgcgga gcagagcagg tctactggtc gcttccagac atgatgaagg atcctgtcac   15000
tttccgctcc actagacaag tcagtaacta ccctgtggtg ggtgcagagc ttatgcccgt   15060
cttctcaaag agcttctaca acgaacaagc tgtgtactcc cagcagctcc gccagtccac   15120
ctcgcttacg cacgtcttca accgctttcc tgagaaccag attttaatcc gtccgccggc   15180
gcccaccatt accaccgtca gtgaaaacgt tcctgctctc acagatcacg ggaccctgcc   15240
gttgcgcagc agtatccggg gagtccaacg tgtgaccgtt actgacgcca gacgccgcac   15300
ctgtccctac gtgtacaagg cactgggcat agtcgcaccg cgcgtccttt caagccgcac   15360
tttctaaaaa aaaaaaaaat gtccattctt atctcgccca gtaataacac cggttggggt   15420
ctgcgcgctc caagcaagat gtacggaggc gcacgcaaac gttctaccca acatcctgtc   15480
cgtgttcgcg gacatttcg cgctccatgg ggcgccctca agggccgcac tcgcgttcga    15540
accaccgtcg atgatgtaat cgatcaggtg gttgccgacg cccgtaatta tactcctact   15600
gcgcctacat ctactgtgga tgcagttatt gacagtgtag tggctgacgc tcgcaactat   15660
gctcgacgta agagccggcg aaggcgcatt gccagacgcc accgagctac cactgccatg   15720
cgagccgcaa gagctctgct acgaagagct agacgcgtgg ggcgaagagc catgcttagg   15780
gcggccagac gtgcagcttc gggcgccagc gccggcaggt cccgcaggca agcagccgct   15840
ttcgcagcgg cgactattgc cgacatggcc caatcgcgaa gaggcaatgt atactggtg    15900 cgtgacgctg ccaccggtca acgtgtaccc gtgcgcaccc gtcccctcg cacttagaag    15960 atactgagca gtctccgatg ttgtgtccca gcggcgagga tgtccaagcg caaatacaag   16020
gaagaaatgc tgcaggttat cgcacctgaa gtctacggcc aaccgttgaa ggatgaaaaa   16080
aaaccccgca aaatcaagcg ggttaaaaag gacaaaaaag aagaggaaga tggcgatgat   16140
gggctggcgg agtttgtgcg cgagtttgcc ccacggcgac gcgtgcaatg cgtgggcgc    16200 aaagttcgac atgtgttgag acctggaact tcggtggtct ttacacccgg cgagcgttca   16260
agcgctactt ttaagcgttc ctatgatgag gtgtacgggg atgatgatat tcttgagcag   16320
gcggctgacc gattaggcga gtttgctat ggcaagcgta gtagaataac ttccaaggat    16380
gagacagtgt cgataccctt ggatcatgga aatcccaccc ctagtcttaa accggtcact   16440
```

```
ttgcagcaag tgttacccgt aactccgcga acaggtgtta aacgcgaagg tgaagatttg    16500
tatcccacta tgcaactgat ggtacccaaa cgccagaagt tggaggacgt tttggagaaa    16560
gtaaaagtgg atccagatat tcaacctgag gttaaagtga gacccattaa gcaggtagcg    16620
cctggtctgg gggtacaaac tgtagacatt aagattccca ctgaaagtat ggaagtgcaa    16680
actgaacccg caaagcctac tgccacctcc actgaagtgc aaacggatcc atggatgccc    16740
atgcctatta caactgacgc cgccggtccc actcgaagat cccgacgaaa gtacggtcca    16800
gcaagtctgt tgatgcccaa ttatgttgta cacccatcta ttattcctac tcctggttac    16860
cgaggcactc gctactatcg cagccgaaac agtacctccc gccgtcgccg caagacacct    16920
gcaaatcgca gtcgtcgccg tagacgcaca agcaaaccga ctcccggcgc cctggtgcgg    16980
caagtgtacc gcaatggtag tgcggaacct ttgacactgc cgcgtgcgcg ttaccatccg    17040
agtatcatca cttaatcaat gttgccgctg cctccttgca gatatggccc tcacttgtcg    17100
ccttcgcgtt cccatcactg gttaccgagg aagaaactcg cgccgtagaa gagggatgtt    17160
gggacgcgga atgcgacgct acaggcgacg gcgtgctatc cgcaagcaat tgcggggtgg    17220
ttttttacca gccttaattc caattatcgc tgctgcaatt ggcgcgatac caggcatagc    17280
ttccgtggcg gttcaggcct cgcaacgaca ttgacattgg aaaaaaacgt ataaataaaa    17340 aaaaaaaat acaatggact ctgacactcc tggtcctgtg actatgtttt cttagagatg    17400
gaagacatca atttttcatc cttggctccg cgacacggca cgaagccgta catgggcacc    17460
tggagcgaca tcggcacgag ccaactgaac ggggcgcct tcaattggag cagtatctgg    17520
agcgggctta aaaattttgg ctcaaccata aaaacatacg ggaacaaagc ttggaacagc    17580
agtacaggac aggcgcttag aaataaactt aaagaccaga acttccaaca aaagtagtc    17640 gatgggatag cttccggcat caatggagtg gtagatttgg ctaaccaggc tgtgcagaaa    17700
aagataaaca gtcgtttgga cccgccgcca gcaaccccag gtgaaatgca agtggaggaa    17760
gaaattcctc cgccagaaaa acgaggcgac aagcgtccgc gtcccgattt ggaagagacg    17820
ctggtgacgc gcgtagatga accgccttct tatgaggaag caacgaagct tggaatgccc    17880
accactagac cgatagcccc aatggccacc ggggtgatga aaccttctca gttgcatcga    17940
cccgtcacct tggatttgcc ccctcccctt gctgctactg ctgtacccgc ttctaagcct    18000
gtcgctgccc cgaaaccagt cgccgtagcc aggtcacgtc ccgggggcgc tcctcgtcca    18060
aatgcgcact ggcaaaatac tctgaacagc atcgtgggtc taggcgtgca aagtgtaaaa    18120
cgccgtcgct gcttttaatt aaatatggag tagcgcttaa cttgcctatc tgtgtatatg    18180
tgtcattaca cgccgtcaca gcagcagagg aaaaaaggaa gaggtcgtgc gtcgacgctg    18240
agttactttc aagatggcca ccccatcgat gctgccccaa tgggcataca tgcacatcgc    18300
cggacaggat gcttcggagt acctgagtcc gggtctggtg cagttcgccc gcgccacaga    18360
cacctacttc aatctgggaa ataagtttag aaatcccacc gtagcgccga cccacgatgt    18420
gaccaccgac cgtagccagc ggctcatgtt gcgcttcgtg cccgttgacc gggaggacaa    18480
tacatactct tacaaagtgc ggtacacccct ggccgtgggc gacaacagag tgctggatat    18540
ggccagcacg ttcttttgaca ttaggggtgt gttggacaga ggtcccagtt tcaaacccta    18600
ttctggtacg gcttacaact ccctggctcc taaaggcgct ccaaatacat ctcagtggat    18660
tgcagaaggt gtaaaaaata caactggtga ggaacacgta acagaagagg aaaccaatac    18720
tactacttac acttttggca atgctcctgt aaaagctgaa gctgaaatta caaaagaagg    18780
```

```
actcccagta ggtttggaag tttcagatga agaaagtaaa ccgatttatg ctgataaaac   18840
atatcagcca gaacctcagc tgggagatga aacttggact gaccttgatg gaaaaaccga   18900
aaagtatgga ggcagggctc tcaaacccga tactaagatg aaaccatgct acgggtcctt   18960
tgccaaacct actaatgtga aaggcggtca ggcaaaacaa aaaacaacgg agcagccaaa   19020
tcagaaagtc gaatatgata tcgacatgga gttttttgat gcggcatcgc agaaaacaaa   19080
cttaagtcct aaaattgtca tgtatgcaga aaatgtaaat ttggaaactc cagacactca   19140
tgtagtgtac aaacctggaa cagaagacac aagttccgaa gctaatttgg gacaacaatc   19200
tatgcccaac agacccaact acattggctt cagagataac tttattggac ttatgtacta   19260
taacagtact ggtaacatgg gggtgctggc tggtcaagcg tctcagttaa atgcagtggt   19320
tgacttgcag gacagaaaca cagaactttc ttaccaactc ttgcttgact ctctgggcga   19380
cagaaccaga tactttagca tgtggaatca ggctgtggac agttatgatc ctgatgtacg   19440
tgttattgaa aatcatggtg tggaagatga acttcccaac tactgttttc cactggacgg   19500
cataggtgtt ccaacaacca gttacaaatc aatagttcca aatggagaca atgcgcctaa   19560
ttggaaggaa cctgaagtaa atggaacaag tgagatcgga cagggtaatt tgtttgccat   19620
ggaaattaac cttcaagcca atctatggcg aagtttcctt tattccaatg tggctctata   19680
tctcccagac tcgtacaaat acaccccgtc caatgtcact cttccagaaa acaaaaacac   19740
ctacgactac atgaacgggc gggtggtgcc gccatctcta gtagacacct atgtgaacat   19800
tggtgccagg tggtctctgg atgccatgga caatgtcaac ccattcaacc accaccgtaa   19860
cgctggcttg cgttaccgat ccatgcttct gggtaacgga cgttatgtgc ctttccacat   19920
acaagtgcct caaaaattct tcgctgttaa aaacctgctg cttctcccag gctcctacac   19980
ttatgagtgg aactttagga aggatgtgaa catggttcta cagagttccc tcggtaacga   20040
cctgcgggta gatggcgcca gcatcagttt cacgagcatc aacctctatg ctacttttt   20100
ccccatggct cacaacaccg cttccaccct tgaagccatg ctgcggaatg acaccaatga   20160
tcagtcattc aacgactacc tatctgcagc taacatgctc tacccccattc ctgccaatgc   20220
aaccaatatt cccatttcca ttccttctcg caactgggcg gctttcagag ctggtcatt   20280
taccagactg aaaaccaaag aaactccctc tttggggtct ggatttgacc cctactttgt   20340
ctattctggt tctattccct acctggatgg taccttctac ctgaaccaca cttttaagaa   20400
ggtttccatc atgtttgact cttcagtgag ctggcctgga aatgacaggt tactatctcc   20460
taacgaattt gaaataaagc gcactgtgga tggcgaaggc tacaacgtag cccaatgcaa   20520
catgaccaaa gactggttct tggtacagat gctcgccaac tacaacatcg gctatcaggg   20580
cttctacatt ccagaaggat acaaagatcg catgtattca ttttttcagaa acttccagcc   20640
catgagcagg caggtggttg atgaggtcaa ttacaaagac ttcaaggccg tcgccatacc   20700
ctaccaacac aacaactctg gctttgtggg ttacatggct ccgaccatgc gccaaggtca   20760
accctatccc gctaactatc cctatccact cattggaaca actgccgtaa atagtgttac   20820
gcagaaaaag ttcttgtgtg acagaaccat gtggcgcata ccgttctcga gcaacttcat   20880
gtctatgggg gcccttacag acttgggaca gaatatgctc tatgccaact cagctcatgc   20940
tctggacatg acctttgagg tggatccat ggatgagccc accctgcttt atcttctctt   21000
cgaagttttc gacgtggtca gagtgcatca gccacaccgc ggcatcatcg aggcagtcta   21060
cctgcgtaca ccgttctcgg ccggtaacgc taccacgtaa gaagcttctt gcttcttgca   21120
aatagcagct gcaaccatgg cctgcggatc ccaaaacggc tccagcgagc aagagctcag   21180
```

```
agccattgtc caagacctgg gttgcggacc ctattttttg ggaacctacg ataagcgctt    21240
cccggggttc atggcccccg ataagctcgc ctgtgccatt gtaaatacgg ccggacgtga    21300
gacgggggga gagcactggt tggctttcgg ttggaaccca cgttctaaca cctgctacct    21360
ttttgatcct tttggattct cggatgatcg tctcaaacag atttaccagt ttgaatatga    21420
gggtctcctg cgccgcagcg ctcttgctac caaggaccgc tgtattacgc tggaaaaatc    21480
tacccagacc gtgcagggtc cccgttctgc cgcctgcgga ctttctgct gcatgttcct     21540
tcacgccttt gtgcactggc ctgaccgtcc catggacgaa accccacca tgaaattgct     21600
aactggagtg ccaaacaaca tgcttcattc tcctaaagtc cagcccaccc tgtgtgacaa    21660
tcaaaaagca ctctaccatt tcttaatac ccattcgcct tattttcgct cccatcgtac     21720
acacatcgaa agggccactg cgttcgaccg tatggatgtt caataatgac tcatgtaaac    21780
aacgtgttca ataaacatca ctttattttt ttacatgtat caaggctctg cattacttat    21840
ttatttacaa gtcgaatggg ttctgacgag aatcagaatg acccgcaggc agtgatacgt    21900
tgcggaactg atacttgggt tgccacttga attcggaat caccaacttg gaaccggta      21960
tatcgggcag gatgtcactc cacagctttc tggtcagctg caaagctcca agcaggtcag    22020
gagccgaaat cttgaaatca caattaggac cagtgctttg agcgcgagag ttgcggtaca    22080
ccggattgca gcactgaaac accatcagcg acggatgtct cacgcttgcc agcacggtgg    22140
gatctgcaat catgcccaca tccagatctt cagcattggc aatgctgaac ggggtcatct    22200
tgcaggtctg cctacccatg gcgggcaccc aattaggctt gtggttgcaa tcgcagtgca    22260
ggggatcag tatcatcttg gcctgatcct gtctgattcc tggatacacg gctctcatga     22320
aagcatcata ttgcttgaaa gcctgctggg ctttactacc ctcggtataa acatcccgc     22380
aggacctgct cgaaaactgg ttagctgcac agccggcatc attcacacag cagcgggcgt    22440
cattgttagc tatttgcacc acacttctgc cccagcggtt ttgggtgatt ttggttcgct    22500
cgggattctc ctttaaggct cgttgtccgt tctcgctggc cacatccatc tcgataatct    22560
gctccttctg aatcataata ttgccatgca ggcacttcag cttgccctca taatcattgc    22620
agccatgagg ccacaacgca cagcctgtac attcccaatt atggtgggcg atctgagaaa    22680
aagaatgtat cattccctgc agaaatcttc ccatcatcgt gctcagtgtc ttgtgactag    22740
tgaaagttaa ctggatgcct cggtgctcct cgtttacgta ctggtgacag atgcgcttgt    22800
attgttcgtg ttgctcaggc attagtttaa aagaggttct aagttcgtta ccagcctgt     22860
acttctccat cagcagacac atcacttcca tgcctttctc ccaagcagac accaggggca    22920
agctaatcgg attcttaaca gtgcaggcag cagctcctt agccagaggg tcatctttag     22980
cgatcttctc aatgcttctt ttgccatcct tctcaacgat gcgcacgggc gggtagctga    23040
aacccactgc tacaagttgc gcctcttctc tttcttcttc gctgtcttga ctgatgtctt    23100
gcatggggat atgtttggtc ttccttggct tcttttggg gggtatcgga ggaggaggac     23160
tgtcgctccg ttccggagac agggaggatt gtgacgtttc gctcaccatt accaactgac    23220
tgtcggtaga agaacctgac cccacacggc gacaggtgtt tctcttcggg ggcagaggtg    23280
gaggcgattg cgaagggctg cggtccgacc tggaaggcgg atgactggca gaacccttc     23340
cgcgttcggg ggtgtgctcc ctgtggcggt cgcttaactg atttccttcg cggctggcca    23400
ttgtgttctc ctaggcagag aaacaacaga catggaaact cagccattgc tgtcaacatc    23460
gccacgagtg ccatcacatc tcgtcctcag cgacgaggaa aaggagcaga gcttaagcat    23520
```

```
tccaccgccc agtcctgcca ccacctctac cctagaagat aaggaggtcg acgcatctca    23580
tgacatgcag aataaaaaag cgaaagagtc tgagacagac atcgagcaag acccgggcta    23640
tgtgacaccg gtggaacacg aggaagagtt gaaacgcttt ctagagagag aggatgaaaa    23700
ctgcccaaaa caacgagcag ataactatca ccaagatgct ggaaataggg atcagaacac    23760
cgactacctc atagggcttg acggggaaga cgcgctcctt aaacatctag caagacagtc    23820
gctcatagtc aaggatgcat tattggacag aactgaagtg cccatcagtg tggaagagct    23880
cagccgcgcc tacgagctta acctcttttc acctcgtact cccccaaaac gtcagccaaa    23940
cggcacctgc gagccaaatc ctcgcttaaa cttttatcca gcttttgctg tgccagaagt    24000
actggctacc tatcacatct tttttaaaaa tcaaaaaatt ccagtctcct gccgcgctaa    24060
tcgcacccgc gccgatgccc tactcaatct gggacctggt tcacgcttac ctgatatagc    24120
ttccttggaa gaggttccaa agatcttcga gggtctgggc aataatgaga ctcgggccgc    24180
aaatgctctg caaagggag aaaatggcat ggatgagcat cacagcgttc tggtggaatt    24240
ggaaggcgat aatgccagac tcgcagtact caagcgaagc atcgaggtca cacacttcgc    24300
atatcccgct gtcaacctgc cccctaaagt catgacggcg tcatggacc agttactcat    24360 taagcgcgca agtccccttt cagaagacat gcatgaccca gatgcctgtg atgagggtaa    24420
accagtggtc agtgatgagc agctaacccg atggctgggc accgactctc cagggatt    24480 ggaagagcgt cgcaagctta tgatggccgt ggtgctggtt accgtagaac tagagtgtct    24540
ccgacgtttc tttaccgatt cagaaacctt gcgcaaactc gaagagaatc tgcactacac    24600
ttttagacac ggctttgtgc ggcaggcatg caagatatct aacgtggaac tcaccaacct    24660
ggtttcctac atgggtattc tgcatgagaa tcgcctagga caaagcgtgc tgcacagcac    24720
cctgaagggg gaagcccgcc gtgattacat ccgcgattgt gtctatctgt acctgtgcca    24780
aacgtggcaa accggcatgg gtgtatggca gcaatgttta gaagaacaga acttgaaaga    24840
gcttgacaag ctcttacaga aatctcttaa ggttctgtgg acagggttcg acgagcgcac    24900
cgtcgcttcc gacctggcag acctcatctt cccagagcgt ctcagggtta ctttgcgaaa    24960
cggattgcct gactttatga gccagagcat gcttaacaat tttcgctctt tcatcctgga    25020
acgctccggt atcctgcccg ccacctgctg cgcactgccc tccgactttg tgcctctcac    25080
ctaccgcgag tgccccccgc cgctatggag tcactgctac ctgttccgtc tggccaacta    25140
tctctcctac cactcggatg tgatcgagga tgtgagcgga gacggcttgc tggagtgtca    25200
ctgccgctgc aatctgtgca cgccccaccg gtccctagct tgcaaccccc agttgatgag    25260
cgaaacccag ataataggca cctttgaatt gcaaggcccc agcagccaag gcgatgggtc    25320
ttctcctggg caaagtttaa aactgacccc gggactgtgg acctccgcct acttgcgcaa    25380
gtttgctccg gaagattacc accctatga aatcaagttc tatgaggacc aatcacagcc    25440
tccaaaggcc gaactttcgg cctgcgtcat cacccagggg gcaattctgg cccaattgca    25500
agccatccaa aaatcccgcc aagaatttct actgaaaaag ggtaaggggg tctaccttga    25560
cccccagacc ggcgaggaac tcaacacaag gttccctcag gatgtcccaa cgacgagaaa    25620
acaagaagtt gaaggtgcag ccgccgcccc cagaagatat ggaggaagat gggacagtc    25680 aggcagagga ggcggaggag gacagtctgg aggacagtct ggaggaagac agtttggagg    25740
aggaaaacga ggaggcagag gaggtggaag aagtaaccgc cgacaaacag ttatcctcgg    25800
ctgcggagac aagcaacagc gctaccatct ccgctccgag tcgaggaacc cggcggcgtc    25860
ccagcagtag atgggacgag accggacgct tcccgaaccc aaccagcgct tccaagaccg    25920
```

```
gtaagaagga tcggcaggga tacaagtcct ggcgggggca taagaatgcc atcatctcct    25980
gcttgcatga gtgcggggc  aacatatcct tcacgcggcg ctacttgcta ttccaccatg    26040
gggtgaactt tccgcgcaat gttttgcatt actaccgtca cctccacagc ccctactata    26100
gccagcaaat cccggcagtc tcgacagata aagacagcgg cggcgacctc aacagaaaa    26160 ccagcagcgg cagttagaaa atacacaaca agtgcagcaa caggaggatt aaagattaca    26220
gccaacgagc cagcgcaaac ccgagagtta agaaatcgga tctttccaac cctgtatgcc    26280
atcttccagc agagtcgggg tcaagagcag gaactgaaaa taaaaaaccg atctctgcgt    26340
tcgctcacca gaagttgttt gtatcacaag agcgaagatc aacttcagcg cactctcgag    26400
gacgccgagc ctctcttcaa caagtactgc gcgctgactc ttaaagagta ggcagcgacc    26460
gcgcttattc aaaaaaggcg ggaattacat catcctcgac atgagtaaag aaattcccac    26520
gccttacatg tggagttatc aaccccaaat gggattggcg gcaggcgcct cccaggacta    26580
ctccacccgc atgaattggc tcagcgccgg gccttctatg atttctcgag ttaatgatat    26640
acgcgcctac cgaaaccaaa tacttttgga acagtcagct cttaccacca cgccccgcca    26700
acaccttaat cccagaaatt ggcccgccgc cctagtgtac caggaaagtc ccgctcccac    26760
cactgtatta cttcctcgag acgcccaggc cgaagtccaa atgactaatg caggtgcgca    26820
gttagctggc ggctccaccc tatgtcgtca caggcctcgg cataatataa aacgcctgat    26880
gatcagaggc cgaggtatcc agctcaacga cgagtcggtg agctctccgc ttggtctacg    26940
accagacgga atctttcaga ttgccggctg cgggagatct tccttcaccc ctcgtcaggc    27000
tgttctgact ttggaaagtt cgtcttcgca accccgctcg gcggaatcg  gaccgttca     27060 atttgtggag gagtttactc cctctgtcta cttcaacccc ttctccggat ctcctgggca    27120
ttacccggac gagttcatac cgaacttcga cgcgattagc gagtcagtgg acggctacga    27180
ttgatgtctg gtgacgcggc tgagctatct cggctgcgac atctagacca ctgccgccgc    27240
tttcgctgct ttgcccggga actcattgag ttcatctact tcgaactccc caaggatcac    27300
cctcaaggtc cggcccacgg agtgcggatt ctatcgaag  gcaaaataga ctctcgcctg    27360
caacgaattt tctcccagcg gcccgtgctg atcgagcgag accagggaaa caccacggtt    27420
tccatctact gcatttgtaa tcaccccgga ttgcatgaaa gcctttgctg tcttatgtgt    27480
actgagttta ataaaaactg aattaagact ctcctacgga ctgccgcttc ttcaacccgg    27540
attttacaac cagaagaacg aaacttttcc tgtcgtccag gactctgtta acttcacctt    27600
tcctactcac aaactagaag ctcaacgact acaccgcttt tccagaagca ttttccctac    27660
taatactact ttcaaaaccg gaggtgagct ccaaggtctt cctacagaaa acccttgggt    27720
ggaagcgggc cttgtagtgc taggaattct tgcgggtggg cttgtgatta ttcttttgcta   27780 cctatacaca ccttgcttca cttttcttagt ggtgttgtgg tattggttta aaaatgggg    27840 cccatactag tcttgcttgt tttactttcg cttttggaac cgggttctgc caattacgat    27900
ccatgtctag acttcgaccc agaaaactgc acacttactt ttgcacccga cacaagccgc    27960
atctgtggag ttcttattaa gtgcggatgg gaatgcaggt ccgttgaaat tacacacaat    28020
aacaaaacct ggaacaatac cttatccacc acatgggagc caggagttcc cgagtggtac    28080
actgtctctg tccgaggtcc tgacggttcc atccgcatta gtaacaacac tttcattttt    28140
tctgaaatgt gcgatctggc catgttcatg agcaaacagt attctctatg gcctcctagc    28200
aaggacaaca tcgtaacgtt ctccattgct tattgcttgt gcgcttgcct tcttactgct    28260
```

```
ttactgtgcg tatgcataca cctgcttgta accactcgca tcaaaaacgc caataacaaa    28320
gaaaaaatgc cttaacctct ttctgtttac agacatggct tctcttacat ctctcatatt    28380
tgtcagcatt gtcactgccg ctcatggaca acagtcgtc tctatccctc taggacataa     28440
ttacactctc ataggacccc caatcacttc agaggtcatc tgggccaaac tgggaagcgt    28500
tgattacttt gatataatct gcaacaaaac aaaaccaata atagtaactt gcaacataca    28560
aaatcttaca ttgattaatg ttagcaaagt ttacagcggt tactattatg gttatgacag    28620
atacagtagt caatatagaa attacttggt tcgtgttacc cagttgaaaa ccacgaaaat    28680
gccaaatatg gcaaagattc gatccgatga caattctcta gaacttttta catctcccac    28740
cacacccgac gaaaaaaaca tcccagattc aatgattgca attgttgcag cggtggcagt    28800
ggtgatggca ctaataataa tatgcatgct tttatatgct tgtcgctaca aaagtttca    28860 tcctaaaaaa caagatctcc tactaaggct taacatttaa tttcttttta tacagccatg    28920
gtttccacta ccacattcct tatgcttact agtctcgcaa ctctgacttc tgctcgctca    28980 caccctcactg taactatagg ctcaaactgc acactaaaag gacctcaagg tggtcatgtc    29040
ttttggtgga gaatatatga caatggatgg tttacaaaac catgtgacca acctggtaga    29100
tttttctgca acggcagaga cctaaccatt atcaacgtga cagcaaatga caaaggcttc    29160
tattatggaa ccgactataa aagtagttta gattataaca ttattgtact gccatctacc    29220
actccagcac cccgcacaac tactttctct agcagcagtg tcgctaacaa tacaatttcc    29280
aatccaacct ttgccgcgct tttaaaacgc actgtgaata attctacaac ttcacataca    29340
acaatttcca cttcaacaat cagcattatc gctgcagtga caattggaat atctattctt    29400
gtttttacca taacctacta cgcctgctgc tatagaaaag acaaacataa aggtgatcca    29460
ttacttagat ttgatattta atttgttctt ttttttttta tttacagtat ggtgaacacc    29520
aatcatggta cctagaaatt tcttcttcac catactcatt tgtgcattta atgtttgcgc    29580
tactttcaca gcagtagcca cagcaacccc agactgtata ggagcatttg cttcctatgc    29640 acttttttgct tttgttactt gcatctgcgt atgtagcata gtctgcctgg ttattaattt    29700
tttccaactt atagactgga tccttgtgcg aattgcctac ctgcgccacc atcccgaata    29760
ccgcaaccaa aatatcgcgg cacttcttag actcatctaa aaccatgcag gctatactac    29820
caatattttt gcttctattg cttccctacg ctgtctcaac cccagctgcc tatagtactc    29880
caccagaaca cctagaaaaa tgcaaattcc aacaaccgtg gtcatttctt gcttgctatc    29940
gagaaaaatc agaaatttcc ccaaatttaa taatgattgc tggaataatt aatataatct    30000
gttgcaccat aatttcattt ttgatatacc ccctatttga ttttggctgg aatgctccca    30060
atgcacatga tcatccacaa gacccagagg aacacattcc cctacaaaac atgcaacatc    30120
caatagcgct aatagattac gaaagtgaac cacaacccc actactccct gctattagtt     30180
acttcaacct aaccggcgga gatgactgaa acactcacca cctccaattc cgccgaggat    30240
ctgctcgata tggacggccg cgtctcagaa cagcgactcg cccaactacg catccgccag    30300
cagcaggaac gcgcggccaa agagctcaga gatgtcatcc aaattcacca atgcaaaaaa    30360
ggcatattct gtttggtaaa acaagccaag atatcctacg agatcaccgc tactgaccat    30420
cgcctctctt acgaacttgg cccccaacga caaaaattta cctgcatggt gggaatcaac    30480
cccatagtta tcacccagca aagtggagat actaagggtt gcattcactg ctcctgcgat    30540
tccatcgagt gcacctacac cctgctgaag accctatgcg gcctaagaga cctgctacca    30600
atgaattaaa aaatgattaa taaaaaatca cttacttgaa atcagcaata aggtctctgt    30660
```

```
tgaaattttc tcccagcagc acctcacttc cctcttccca actctggtat tctaaacccc   30720
gttcagcggc atactttctc catactttaa aggggatgtc aaattttagc tcctctcctg   30780
tacccacaat cttcatgtct ttcttcccag atgaccaaga gagtccggct cagtgactcc   30840
ttcaaccctg tctacccccta tgaagatgaa agcacctccc aacaccccett tataaaccca   30900 gggtttattt ccccaaatgg cttcacacaa agcccaaacg gagttcttac tttaaaatgt   30960
ttaaccccac taacaaccac aggcggatct ctacagctaa aagtgggagg gggacttaca   31020
gtggatgaca ccaacggttt tttgaaagaa aacataagtg ccaccacacc actcgttaag   31080
actggtcact ctataggttt accactagga gccggattgg gaacgaatga aaataaactt   31140
tgtatcaaat taggacaagg acttacattc aattcaaaca acatttgcat tgatgacaat   31200
attaacacct tatggacagg agtcaacccc accgaagcca actgtcaaat catgaactcc   31260
agtgaatcta atgattgcaa attaattcta acactagtta aaactggagc actagtcact   31320
gcatttgttt atgttatagg agtatctaac aattttaata tgctaactac acacagaaat   31380
ataaatttta ctgcagagct gttttttcgat tctactggta atttactaac tagactctca   31440
tccctcaaaa ctccacttaa tcataaatca ggacaaaaca tggctactgg tgccattact   31500
aatgctaaag gtttcatgcc cagcacgact gcctatcctt tcaatgataa ttctagagaa   31560
aaagaaaact acatttacgg aacttgttac tacacagcta gtgatcgcac tgcttttccc   31620
attgacatat ctgtcatgct taaccgaaga gcaataaatg acgagacatc atattgtatt   31680
cgtataactt ggtcctggaa cacaggagat gccccagagg tgcaaacctc tgctacaacc   31740
ctagtcacct ccccatttac cttttactac atcagagaag acgactgaca aataaagttt   31800
aacttgttta tttgaaaatc aattcacaaa atccgagtag ttattttgcc tccccttcc   31860 catttaacag aatacaccaa tctctcccca cgcacagctt taaacatttg gataccatta   31920
gatatagaca tggttttaga ttccacattc caaacagttt cagagcgagc caatctgggg   31980
tcagtgatag ataaaaatcc atcgggatag tcttttaaag cgctttcaca gtccaactgc   32040
tgcggatgga ctccggagtc tggatcacgg tcatctggaa aagaacgat gggaatcata   32100 atccgaaaac ggtatcggac gattgtgtct catcaaaccc acaagcagcc gctgtctgcg   32160
tcgctccgtg cgactgctgt ttatgggatc agggtccaca gtgtcctgaa gcatgatttt   32220
aatagccctt aacatcaact ttctggtgcg atgcgcgcag caacgcattc tgatttcact   32280
caaatctttg cagtaggtac aacacattat tacaatattg tttaataaac cataattaaa   32340
agcgctccag ccaaaactca tatctgatat aatcgcccct gcatgaccat cataccaaag   32400
tttaatataa attaaatgac gttccctcaa aaacacacta cccacataca tgatctcttt   32460
tggcatgtgc atattaacaa tctgtctgta ccatggacaa cgttggttaa tcatgcaacc   32520
caatataacc ttccggaacc acactgccaa caccgctccc ccagccatgc attgaagtga   32580
accctgctga ttacaatgac aatgaagaac ccaattctct cgaccgtgaa tcacttgaga   32640
atgaaaaata tctatagtgg cacaacatag acataaatgc atgcatcttc tcataatttt   32700
taactcctca ggatttagaa acatatccca gggaatagga agctcttgca gaacagtaaa   32760
gctggcagaa caaggaagac cacgaacaca acttacacta tgcatagtca tagtatcaca   32820
atctggcaac agcgggtggt cttcagtcat agaagctcgg gtttcatttt cctcacaacg   32880
tggtaactgg gctctggtgt aagggtgatg tctggcgcat gatgtcgagc gtgcgcgcaa   32940
ccttgtcata atggagttgc ttcctgacat tctcgtattt tgtatagcaa aacgcggccc   33000
```

```
tggcagaaca cactcttctt cgccttctat cctgccgctt agcgtgttcc gtgtgatagt    33060
tcaagtacaa ccacactctt aagttggtca aaagaatgct ggcttcagtt gtaatcaaaa    33120
ctccatcgca tctaatcgtt ctgaggaaat catccacggt agcatatgca aatcccaacc    33180
aagcaatgca actggattgt gtttcaagca ggagaggaga gggaagagac ggaagaacca    33240
tgttaatttt tattccaaac gatctcgcag tacttcaaat tgtagatcgc gcagatggca    33300
tctctcgccc ccactgtgtt ggtgaaaaag cacagctaga tcaaagaaa tgcgattttc     33360
aaggtgctca acggtggctt ccagcaaagc ctccacgcgc acatccaaga caaaagaat     33420
accaaaagaa ggagcatttt ctaactcctc aatcatcata ttacattcct gcaccattcc    33480
cagataattt tcagctttcc agccttgaat tattcgtgtc agttcttgtg gtaaatccaa    33540
tccacacatt acaaacaggt cccggagggc gccctccacc accattctta aacacaccct    33600
cataatgaca aaatatcttg ctcctgtgtc acctgtagcg aattgagaat ggcaacatca    33660
attgacatgc ccttggctct aagttcttct ttaagttcta gttgtaaaaa ctctctcata    33720
ttatcaccaa actgcttagc cagaagcccc ccgggaacaa gagcagggga cgctacagtg    33780
cagtacaagc gcagacctcc ccaattggct ccagcaaaaa caagattgga ataagcatat    33840
tgggaaccgc cagtaatatc atcgaagttg ctggaaatat aatcaggcag agtttcttgt    33900
aaaaattgaa taaagaaaaa atttgccaaa aaacattca aaacctctgg gatgcaaatg      33960
caataggtta ccgcgctgcg ctccaacatt gttagttttg aattagtctg caaaaataaa    34020
aaaaaaaaca agcgtcatat catagtagcc tgacgaacag atggataaat cagtcttttcc   34080
atcacaagac aagccacagg gtctccagct cgaccctcgt aaaacctgtc atcatgatta    34140
aacaacagca ccgaaagttc ctcgcggtga ccagcatgaa taattcttga tgaagcatac    34200
aatccagaca tgttagcatc agttaacgag aaaaaacagc caacatagcc tttgggtata    34260
attatgctta atcgtaagta tagcaaagcc acccctcgcg gatacaaagt aaaaggcaca    34320
ggagaataaa aaatataatt atttctctgc tgctgttcag gcaacgtcgc ccccggtccc    34380
tctaaataca catacaaagc ctcatcagcc atggcttacc agacaaagta cagcgggcac    34440
acaaagcaca agctctaaag tgactctcca acctctccac aatatatata tacacaagcc    34500
ctaaactgac gtaatgggag taaagtgtaa aaaatcccgc caaacccaac acacaccccg    34560
aaactgcgtc accagggaaa agtacagttt cacttccgca atcccaacag gcgtaacttc    34620
ctctttctca cggtacgtga tatcccacta acttgcaacg tcattttccc acggtcgcac    34680
cgccccttt agccgttaac cccacagcca atcaccacga gatccacact ttttaaaaatc    34740
acctcattta catattggca ccattccatc tataaggtat attattgatg atg           34793
```

<210> SEQ ID NO 2
<211> LENGTH: 11300
<212> TYPE: PRT
<213> ORGANISM: Adenovirus serotype 11

<400> SEQUENCE: 2

```
His His Gln Tyr Thr Leu Met Glu Trp Cys Gln Tyr Val Asn Glu Val
  1               5                  10                  15

Ile Leu Lys Ser Val Asp Arg Val Val Ile Gly Cys Gly Val Asn Gly
             20                  25                  30

Lys Gly Arg Cys Asp Arg Gly Lys Met Thr Phe Cys Gly Gly Gly Val
         35                  40                  45

Phe Leu Gln Val Val Ala Gly Asn Val Thr His Lys Lys Ala Phe Phe
     50                  55                  60
```

```
Ser Arg Asn Tyr Leu Val Phe Pro Arg Tyr Leu Thr Gly Asn Glu Val
 65                  70                  75                  80

Val Leu Thr Gly Cys Lys Lys Leu Leu Ile Phe Ala Arg Lys Leu Asn
                 85                  90                  95

Glu Glu Val Phe Phe Ile Met Trp Tyr Leu Trp Gln Gly Gly Val Phe
            100                 105                 110

Val Gln Gly Gln Val Asp Phe Asp Pro Leu Arg Gly Gly Phe Asp Tyr
        115                 120                 125

Arg Val Phe Tyr Leu Asn Phe Arg Val Pro Cys Gln Ser Leu Leu Phe
    130                 135                 140

Leu Arg Arg Cys Gln Leu Ile Ala Arg Val Phe Ile Pro Gln Gly Leu
145                 150                 155                 160

Cys Gln Glu Ala Thr Leu Glu Cys Gln Arg Glu Phe Ser Pro Leu
                165                 170                 175

Arg Arg Gln Phe Asn Asn Lys Lys Met Arg Asp Leu Arg Phe Leu Pro
                180                 185                 190

Gln Glu Ile Ile Ser Ala Glu Thr Gly Asn Glu Ile Leu Glu Leu Val
                195                 200                 205

Val His Ala Leu Met Gly Asp Asp Pro Glu Pro Val Gln Leu Phe
    210                 215                 220

Glu Pro Pro Thr Leu Gln Glu Leu Tyr Asp Leu Glu Val Glu Gly Ser
225                 230                 235                 240

Glu Asp Ser Asn Glu Glu Ala Val Asn Gly Phe Phe Thr Asp Ser Met
                245                 250                 255

Leu Leu Ala Ala Asn Glu Gly Leu Glu Leu Asp Pro Pro Leu Asp Thr
                260                 265                 270

Phe Asp Thr Pro Gly Val Ile Val Glu Ser Gly Thr Gly Val Arg Lys
            275                 280                 285

Leu Pro Asp Leu Ser Ser Val Asp Cys Asp Leu His Cys Tyr Glu Asp
    290                 295                 300

Gly Phe Pro Pro Ser Asp Glu Glu Asp His Glu Lys Glu Gln Ser Met
305                 310                 315                 320

Gln Thr Ala Ala Gly Glu Gly Val Lys Ala Ala Asn Val Gly Phe Gln
                325                 330                 335

Leu Asp Cys Pro Glu Leu Pro Gly His Gly Cys Lys Ser Cys Glu Phe
                340                 345                 350

His Arg Lys Asn Thr Gly Val Lys Glu Leu Leu Cys Ser Leu Cys Tyr
            355                 360                 365

Met Arg Thr His Cys His Phe Ile Tyr Ser Lys Cys Val Val Lys Ile
    370                 375                 380

Arg Asn Met Leu Phe Phe Thr Cys Ile Leu Ser Val Ser Phe Val Leu
385                 390                 395                 400

Leu Ile Ile Gly Pro Val Ser Asp Ala Asp Glu Ser Pro Ser Pro Asp
                405                 410                 415

Ser Thr Thr Ser Pro Pro Glu Ile Gln Ala Pro Val Pro Val Asp Val
                420                 425                 430

Arg Lys Pro Ile Pro Val Lys Leu Lys Pro Gly Lys Arg Pro Ala Val
            435                 440                 445

Glu Lys Leu Glu Asp Leu Leu Gln Gly Gly Asp Gly Pro Leu Asp Leu
    450                 455                 460

Ser Thr Arg Lys Arg Pro Arg Gln Val Phe His Ile Arg Val Tyr Leu
465                 470                 475                 480
```

```
Arg Arg Gln Tyr Leu Cys Asp Ser Ala Met Lys Tyr Val Asn Cys Ser
            485                 490                 495

Leu Val Phe Ile Ala Phe Trp Ala Gly Thr Gln Val Tyr Lys Lys Gln
            500                 505                 510

Thr Cys Val Val Ser Ser Glu Leu Ala Phe Ile His Gly Gly Leu Gly
            515                 520                 525

His Phe Gly Arg Pro Glu Asp Ala Thr Val Arg Glu Arg Phe Gly Arg
            530                 535                 540

Ser Leu Arg Phe Leu Glu Ile Leu Val Arg Ile Ser Gly Ser Phe Asp
545                 550                 555                 560

Lys Thr Gly Leu Thr Arg Ile Lys Val Val Gly Arg Leu Pro Arg Thr
                565                 570                 575

Phe Ser Ser Phe Gly Pro Ser Gly Ser Leu Arg Lys Ser Phe Ile Ser
            580                 585                 590

Phe Arg Leu Phe Asn Pro Arg Asn Cys Cys Cys Gly Phe Ser Tyr
            595                 600                 605

Phe Tyr Ile Arg Met Asp Pro Ala Asp Ser Phe Gln Gln Gly Ile Arg
            610                 615                 620

Phe Gly Phe His Ser His Ser Ile Val Glu Asn Met Glu Gly Ser Gln
625                 630                 635                 640

Asp Glu Asp Asn Leu Arg Leu Leu Ala Ser Ala Phe Gly Cys Ser
                645                 650                 655

Gly Asn Pro Glu Ala Ser Thr Gly His Ala Ser Gly Ser Gly Gly Gly
            660                 665                 670

Thr Ala Arg Gly Gln Pro Glu Ser Arg Pro Gly Pro Ser Ser Gly Gly
            675                 680                 685

Gly Gly Val Ala Asp Leu Ser Pro Glu Leu Gln Arg Val Leu Thr Gly
690                 695                 700

Ser Thr Ser Thr Gly Arg Asp Arg Gly Val Lys Arg Glu Arg Ala Ser
705                 710                 715                 720

Ser Gly Thr Asp Ala Arg Ser Glu Leu Ala Leu Ser Leu Met Ser Arg
            725                 730                 735

Arg Arg Pro Glu Thr Ile Trp Trp His Glu Val Gln Lys Glu Gly Arg
            740                 745                 750

Asp Glu Val Ser Val Leu Gln Glu Lys Tyr Ser Leu Glu Gln Val Lys
            755                 760                 765

Thr Cys Trp Leu Glu Pro Glu Asp Asp Trp Glu Val Ala Ile Lys Asn
            770                 775                 780

Tyr Ala Lys Ile Ala Leu Arg Pro Asp Lys Gln Tyr Lys Ile Thr Arg
785                 790                 795                 800

Arg Ile Asn Ile Arg Asn Ala Cys Tyr Ile Ser Gly Asn Gly Ala Glu
                805                 810                 815

Val Val Ile Asp Thr Gln Asp Lys Ala Val Ile Arg Cys Cys Met Met
            820                 825                 830

Asp Met Trp Pro Gly Val Val Gly Met Glu Ala Val Thr Phe Val Asn
            835                 840                 845

Val Lys Phe Arg Gly Asp Gly Tyr Asn Gly Ile Val Phe Met Ala Asn
            850                 855                 860

Thr Lys Leu Ile Leu His Gly Cys Ser Phe Phe Gly Phe Asn Asn Thr
865                 870                 875                 880

Cys Val Asp Ala Trp Gly Gln Val Ser Val Arg Gly Cys Ser Phe Tyr
                885                 890                 895

Ala Cys Trp Ile Ala Thr Ala Gly Arg Thr Lys Ser Gln Leu Ser Leu
```

-continued

```
                900             905             910
Lys Lys Cys Ile Phe Gln Arg Cys Asn Leu Gly Ile Leu Asn Glu Gly
            915                 920                 925

Glu Ala Arg Val Arg His Cys Ala Ser Thr Asp Thr Gly Cys Phe Ile
        930                 935                 940

Leu Ile Lys Gly Asn Ala Ser Val Lys His Asn Met Ile Cys Gly Ala
945                 950                 955                 960

Ser Asp Glu Arg Pro Tyr Gln Met Leu Thr Cys Ala Gly Gly His Cys
                965                 970                 975

Asn Met Leu Ala Thr Val His Ile Val Ser His Gln Arg Lys Lys Trp
            980                 985                 990

Pro Val Phe Asp His Asn Val Met Thr Lys Cys Thr Met His Ala Gly
        995                 1000                1005

Gly Arg Arg Gly Met Phe Met Pro Tyr Gln Cys Asn Met Asn His Val
    1010                1015                1020

Lys Val Leu Leu Glu Pro Asp Ala Phe Ser Arg Met Ser Leu Thr Gly
1025                1030                1035                1040

Ile Phe Asp Met Asn Met Gln Ile Trp Lys Ile Leu Arg Tyr Asp Asp
                1045                1050                1055

Thr Arg Ser Arg Val Arg Ala Cys Glu Cys Gly Gly Lys His Ala Arg
            1060                1065                1070

Phe Gln Pro Val Cys Val Asp Val Thr Glu Asp Leu Arg Pro Asp His
        1075                1080                1085

Leu Val Ile Ala Arg Thr Gly Ala Glu Phe Gly Ser Ser Gly Glu Glu
    1090                1095                1100

Thr Asp Gly Glu Tyr Trp Glu Asn Phe Gly Val Gly Phe Ser Asp Gly
1105                1110                1115                1120

Gln Ile Glu Lys Phe Val Phe Ser Val Leu Gln Leu Ser Val Glu Thr
                1125                1130                1135

Leu Leu Leu Arg Gly Glu Ser Ser Ala Leu Ile Gln Gly Val Ser His
            1140                1145                1150

Pro Gly Gln Glu Phe Val Arg Met Leu Trp Asp Leu Leu Trp Met Glu
        1155                1160                1165

Asp Pro Ser Asn Pro Pro Ile Leu Gln Arg Pro Met Leu Leu Val Leu
    1170                1175                1180

His Leu Trp Thr Gln Leu Gln Leu Pro Pro Pro Leu Leu Pro Leu
1185                1190                1195                1200

Thr Leu Cys Leu Glu Trp Val Thr Met Glu Ala Ser Trp Leu Ile Pro
                1205                1210                1215

Leu Pro Leu Ile Thr Leu Leu Pro Leu Arg Thr Ser Tyr Leu Ser Phe
            1220                1225                1230

Trp Pro Ser Trp Arg Leu Pro Asn Val Trp Asn Phe Leu Ser Arg
        1235                1240                1245

Trp Ser Ser Cys Glu Tyr Lys Leu Ser Leu Leu Ser Ala Arg Gln Ser
    1250                1255                1260

Leu Asn Lys Lys Ile Pro Glu Ser Met Asn Lys Thr Ser Leu Leu Leu
1265                1270                1275                1280

Ile Asn Gln Val Phe Leu Phe His Phe Ser Arg Thr Val Cys Pro Arg
                1285                1290                1295

Pro Pro Ile Ser Ile Ile Glu Asn Ser Val Asp Phe Gln Asp Pro
            1300                1305                1310

Ile Glu Val Gly Leu Asn Val Ile His Gly His Ala Val Phe Gly Val
        1315                1320                1325
```

-continued

```
Glu Ile Ala Pro Leu Lys Gly Phe Met Leu Arg Gly Ser Val Val Asn
    1330                1335                1340

His Pro Val Ile Thr Arg Ser Gln Cys Met Val Leu His Asn Ile Phe
1345                1350                1355                1360

Lys Ala Asp Cys His Arg Ala Leu Gly Val Gly Val Tyr Lys Pro Val
                1365                1370                1375

Glu Leu Gly Trp Val His Ser Gly Asn Tyr Val His Phe Gly Leu Asp
            1380                1385                1390

Phe Val Gly Asn Ile Ala Ala Lys Ile Pro Ser Trp Val His Val Met
        1395                1400                1405

Lys Asp His Gln Asp Gly Val Ser Gly Thr Phe Arg Lys Phe Ile Val
    1410                1415                1420

Gln Leu Gly Trp Lys Ser Val Glu Lys Phe Gly Asp Thr Leu Val Ser
1425                1430                1435                1440

Ser Lys Ile Phe His Ala Leu Ile His Asp Asn Ser Asn Gly Ala Val
                1445                1450                1455

Gly Ser Gly Ala Gly Lys His Val Pro Trp Val His Ile Ile Val Met
            1460                1465                1470

Phe Leu Ser Ile Ile Ile Ser His Phe Asn Glu Phe Gly Ala Glu Ser
        1475                1480                1485

Thr Arg Leu Gly Tyr Glu Cys Ser Phe Gly Pro Arg Ser Ile Val Pro
    1490                1495                1500

Leu Thr Asp Leu His Phe Pro Ser Phe Gln Phe Arg Gly Trp Asn His
1505                1510                1515                1520

Val His Leu Gly Gly Tyr Glu Lys His Arg Phe Trp Gly Gly Asp
                1525                1530                1535

Leu Gln Ile Ser Glu Gln Leu Arg Phe Ala Thr Ser Gly Gly Ala Ile
            1540                1545                1550

Asn Asp Ser Asp Tyr Gly Leu Gln Val Val Val Gly Thr Ala Thr Ala
        1555                1560                1565

Val Phe Ser Lys Gln Gly Gly His Leu Val His His Phe Pro Tyr Met
    1570                1575                1580

His Ile Phe Pro His Gln Ile His Glu Ala Leu Ser Ser Lys Phe Leu
1585                1590                1595                1600

Gly Lys Val Phe Gln Arg Phe Gln Thr Val Ser His Gly His Phe Gly
                1605                1610                1615

Glu Ser Leu Leu Gln Lys Phe Ser Val Pro Gln Phe Ser Asp Val Phe
            1620                1625                1630

Tyr Gly Ile Ser Ile Gln Gln Thr Ser Ser Phe Arg Gly Phe Gly Arg
        1635                1640                1645

Leu Leu Glu Gly Met Arg Arg Trp Ala Ser Ser Ala Ala Arg Val Arg
    1650                1655                1660

Ser Phe Gln Gly Leu Ser Val Arg Val Arg Val Val Ser Val Thr Val
1665                1670                1675                1680

Lys Gly Cys Ala Pro Ala Trp Ala Leu Ala Arg Val Arg Phe Arg Leu
                1685                1690                1695

Ile Leu Leu Val Glu Asn Phe Cys Arg Leu Ala Pro Cys Met Ser Ala
            1700                1705                1710

Lys Gln Phe Thr Met Ser Ser Leu Ser Ala Ser Ala Ala Trp Pro Leu
        1715                1720                1725

Ala Arg Ser Leu Pro Leu Glu Val Phe Leu His Thr Gly Gln Tyr Arg
    1730                1735                1740
```

-continued

```
His Phe Ser Ala Tyr Asn Leu Gly Ala Arg Lys Thr Asp Ser Gly Glu
1745                1750                1755                1760

Tyr Ala Ser Ala Pro Gln Glu Ala Gln Thr Val Ser His Ser Thr Ser
                1765                1770                1775

Gln Val Lys Ser Gly Ser Leu Gly Ser Lys Thr Ser Phe Pro Pro Tyr
            1780                1785                1790

Phe Leu Met Arg Phe Leu Pro Leu Val Ser Met Ser Ser Cys Pro Arg
        1795                1800                1805

Val Thr Asn Arg Leu Ser Val Ser Pro Thr Asp Phe Thr Gly Leu Phe
    1810                1815                1820

Ser Ser Gly Val Pro Arg Ser Ser Tyr Arg Asn Ser Asp His Ser
1825                1830                1835                1840

Asp Thr Lys Ala Arg Val Gln Ala Ser Thr Lys Glu Ala Met Trp Glu
                1845                1850                1855

Gly Arg Ser Leu Ser Thr Arg Gly Ser Thr Phe Ser Lys Val Cys Lys
            1860                1865                1870

His Met Ser Pro Ser Ser Thr Ser Arg Asn Val Ile Gly Leu Val Tyr
        1875                1880                1885

Phe Thr Pro Gly Val Pro Ala Gly Gly Val Lys Gly Ala Val Leu Cys
    1890                1895                1900

Ser Ser Ser Leu Ser Ser Gly Ser Leu Ser Arg Asn Val Ser Cys Trp
1905                1910                1915                1920

Gly Arg Tyr Ser Leu Ser Lys Ala Gly Met Thr Ser Ala Leu Arg Leu
                1925                1930                1935

Ser Val Ser Lys Asn Glu Glu Asp Leu Ile Leu Thr Val Pro Val Glu
            1940                1945                1950

Met Pro Phe Met Arg Phe Ser Ser Ile Trp Ser Glu Asn Thr Ile Phe
        1955                1960                1965

Leu Leu Ser Ser Leu Val Ala Asn Asp Pro Tyr Arg Ala Leu Asp Lys
    1970                1975                1980

Ser Leu Ala Met Asp Arg Met Val Trp Phe Phe Ser Leu Ser Ala Arg
1985                1990                1995                2000

Ser Leu Ala Ala Met Leu Ser Trp Thr Tyr Ser Arg Ala Arg His Phe
                2005                2010                2015

His Ser Gly Lys Ile Val Val Asn Ser Ser Gly Thr Ile Leu Thr Cys
            2020                2025                2030

His Pro Arg Leu Cys Lys Val Ile Lys Ser Thr Leu Val Ala Thr Ser
        2035                2040                2045

Pro Arg Arg Gly Ser Leu Val Gln Gln Ser Leu Pro Pro Phe Leu Glu
    2050                2055                2060

Gln Lys Gly Gly Ser Gly Ser Ser Ile Ser Ser Ser Gly Gly Ser Ala
2065                2070                2075                2080

Ser Met Val Lys Ile Pro Gly Ser Lys Ser Leu Ser Lys Leu Met Gly
                2085                2090                2095

Val Gly Ser Ser Lys Ala Ile Cys His Ser Arg Ala Ala Ser Ala Arg
            2100                2105                2110

Ser Tyr Gly Leu Arg Gly Leu Pro His Gly Met Gly Trp Val Ser Ala
        2115                2120                2125

Glu Ala Tyr Met Pro Gln Met Ser Thr Met Gly Ser Ser Lys Met Pro
    2130                2135                2140

Met Val Gly His Arg Pro Pro Leu Ile Leu Ala Arg Thr Ser Tyr Ser
2145                2150                2155                2160

Ser Cys Asp Gly Ala Ser Ser Pro Gly Pro Lys Leu Val Arg Leu Gly
```

```
                    2165                2170                2175
Phe Ser Val Leu Thr Ile Trp Arg Lys Met Ala Glu Leu Glu Met
            2180                2185                2190
Val Gly Leu Lys Met Leu Lys Trp Ala Gly Arg Pro Thr Glu Ser Leu
            2195                2200                2205
Thr Lys Trp Ala Asp Ser Ser Leu Val Thr Ser Ser Ala Val Thr Ser
            2210                2215                2220
Thr Ser Arg Ala Gln Ser Ser Val Ser Met Met Ser Pro Gly Trp Phe
2225                2230                2235                2240
Phe Phe Ser His Ser Ser Arg Leu Arg Arg Tyr Ser Ser Arg Ser Phe
            2245                2250                2255
Gln Tyr Ser Ser Ser Gly Asn Pro Ser Leu Ser Ala Arg Asp Pro Ser
            2260                2265                2270
Met Asn Leu Thr Ala Leu Gly Gln Gln Pro Phe Ser Thr Gly Arg Glu
            2275                2280                2285
Tyr Ala Ala Ala Phe Arg Ser Glu Ala Val Arg Ala Lys Val Ser Leu
            2290                2295                2300
Thr Met Thr Leu Arg Asn Trp Tyr Leu Lys Ser Met Ser Ser Gln Ala
2305                2310                2315                2320
Pro Cys Ser Gln Ser Trp Lys Ser Thr Arg Phe Leu Ala Gly Leu Gly
            2325                2330                2335
Lys Ala Lys Val Thr Ser Leu Lys Arg Ile Leu Pro Ala Leu Gly Ile
            2340                2345                2350
Lys Leu Arg Val Met Arg Lys Gly Cys Gly Thr Ser Ala Arg Leu Leu
            2355                2360                2365
Ile Thr Trp Ala Ala Arg Thr Ile Ser Ser Lys Pro Leu Met Leu Cys
            2370                2375                2380
Pro Thr Met Tyr Asn Ser Met Lys Arg Gly Val Pro Leu Thr Gly Ser
2385                2390                2395                2400
Leu Leu Ser Ser Ser Lys Val Arg Ser Val Gly Ser Asp Lys Ala Cys
            2405                2410                2415
Ser Arg Ala His Ser Cys Arg Gly Phe Ala Cys Arg Asn Asp Asp Gln
            2420                2425                2430
Arg Ser Thr Ala Ser Ala Val Cys Asn Trp Ser Arg Tyr Arg Lys Cys
            2435                2440                2445
Arg Pro Ile Ala Ile Phe Ser Gly Val Thr Gln Lys Val Leu Gly Ser
            2450                2455                2460
Cys Cys His Arg Ser His Leu Ser Leu Met Ala Arg Ser Trp Ala Met
2465                2470                2475                2480
Leu Thr Arg Arg Ser Ser Pro Glu Ser Phe Met Thr Ser Met Lys Gly
            2485                2490                2495
Thr Ser Cys Leu Pro Lys Asp Pro Ile Gln Val Val Ser Thr Ser Val
            2500                2505                2510
Arg Lys Ser Leu Ser Val Arg Gly Glu Pro Ile Gly Lys Asn Trp Ile
            2515                2520                2525
Ser Cys His Gln Leu Glu Asp Trp Leu Leu Met Trp Lys Lys Phe Leu
            2530                2535                2540
Arg Arg Ala Glu His Ser Cys Leu Cys Leu Tyr Arg Arg Pro Gln Ser
2545                2550                2555                2560
Gln Arg Cys Thr Gly Cys Ile Ser Met Ser Cys Thr Trp Leu Pro Leu
            2565                2570                2575
Thr Arg Asn Phe Ser Gly Lys Pro Arg Pro Gly Asp Cys Ile Ser Cys
            2580                2585                2590
```

-continued

```
Ser Ser Ile Phe Ala Val Ser Ala Cys Ser Ser Val Ser Met Val
        2595                2600                2605

Val Met Leu Thr Ser Pro Arg Gly Arg Gln Val Gln Thr Ser Ala Arg
    2610                2615                2620

Glu Gly Arg Ser Arg Thr Arg Ala Arg Arg Leu Glu Leu Ser Arg Val
2625                2630                2635                2640

Leu Arg Arg Cys Gly Leu Arg Leu Val Gly Arg Asp Arg Arg Leu Thr
            2645                2650                2655

Cys Met Ile Phe Ser Arg Ala Cys Gly Arg Phe Arg Trp Tyr Leu Ile
        2660                2665                2670

Ser Thr Gly Ser Phe Val Glu Thr Ser Met Ala Cys Arg Val Pro Cys
        2675                2680                2685

Pro Leu Gly Ala Thr Thr Val Pro Leu Phe Phe Leu Leu Ile Gly Gly
        2690                2695                2700

Gly Ser Leu Ala Ser Cys Met Leu Arg Ser Gly Asp Gly Asp Ala Arg
2705                2710                2715                2720

Arg Ala Ala Ala Val Val Pro Asp Pro Arg Ala Trp Leu Val Val Ala
            2725                2730                2735

Arg Arg Arg Arg Ala Arg Ala Gly Ser Gly Thr Ala Leu Glu Asp Leu
        2740                2745                2750

Arg Ala Pro Pro Arg Val Asp Arg Leu Val Ser Asp Val Ser Gly Lys
        2755                2760                2765

Leu Pro Ala Pro Ala Thr Lys Arg Val Gln Gln Asn Gln Phe Arg Tyr
    2770                2775                2780

Arg Arg Gln Leu Val Ser Val Phe Leu Val Arg His Gln Ser Cys Pro
2785                2790                2795                2800

Gly Arg Arg Ser Pro Pro Thr Ala Arg Phe Leu Pro Glu Asp Leu
            2805                2810                2815

Arg Asp Pro Leu Phe Arg Arg Trp Pro Arg Gly His Trp Arg Tyr Gly
        2820                2825                2830

Pro Val Gly Arg Met His Ser Cys Pro Pro Arg Ser Arg Arg Gly Cys
        2835                2840                2845

Lys Pro Arg Pro Pro Arg Ser Leu Leu Arg Ala Ser Pro Pro Glu Arg
        2850                2855                2860

Gly Ala Pro Arg Val Trp Arg Pro His Ser Cys Ile Gly Ala Glu Lys
2865                2870                2875                2880

Gly Ser Val Trp Trp Gln Cys Val Arg Arg Arg Asn Thr Ser Ile
            2885                2890                2895

Val Ser Ala Ala Phe Arg His Arg Pro Glu Leu Pro Ser Ala Pro Trp
        2900                2905                2910

Pro Arg Arg Ser Pro Arg Gln Asn Lys Thr Gly Ser Phe Ala Arg Thr
        2915                2920                2925

Arg Ser Ile Pro Pro Arg Glu Asp Gly Val Arg Leu Trp Trp Pro Val
    2930                2935                2940

Leu Arg Val Arg Arg Leu Pro Gly Ser Leu Leu Pro Leu Leu Ser Leu
2945                2950                2955                2960

Leu Pro Leu Thr Ser Leu Leu Arg Leu Gln Ala Gly Ala Glu Gly Ala
            2965                2970                2975

Arg Gly Asp Val Asp Gly Ala Arg Ala Asn Gly Arg Ile Val Gln Pro
        2980                2985                2990

Leu Arg Gly Gly Gly Ala Trp Phe Gln Arg Arg Gly Arg Ser Arg Ala
        2995                3000                3005
```

```
Val Ala Glu Lys His Arg Arg Ala Ser Pro Ser Gly Asp Trp Glu Val
    3010                3015                3020

Leu Arg Leu Gly Gly Arg Gly Arg Leu Tyr Ile Leu Leu Ile Gly Pro
3025                3030                3035                3040

Gly Leu His Ala Glu Ile Ser Cys Gln Asp Pro Arg Asp Leu Lys Thr
            3045                3050                3055

Phe Arg Arg Lys Arg Leu Thr Ser His Ser His Lys Val Gly Val Arg
            3060                3065                3070

Leu Leu Val Gly Gly Gly Gly Tyr Val Phe Gly Leu Gly Leu Leu Phe
            3075                3080                3085

Leu Leu His Leu Gly Lys Val Arg Arg Cys Cys Trp Asn Ser Arg Gln
            3090                3095                3100

Phe Asp Gly Gly Trp Trp Arg Gly Ala Pro Gly Leu Trp Val Arg Leu
3105                3110                3115                3120

Ala Gly Tyr Ala Gly Asp Trp Pro Phe Pro Lys His Tyr Pro Asp Ile
            3125                3130                3135

Gln Asp Leu Cys Ser Ser Leu Ala Ala Val Leu Arg Ala Leu Leu Pro
            3140                3145                3150

His Pro Phe Cys His Ala Tyr Val Val Gln Ile Arg Ala Leu Val Val
            3155                3160                3165

Pro Val Pro Ser Gln Leu Arg Leu Phe Arg Arg Gly Trp Leu Ala Val
            3170                3175                3180

Leu Gly Gly Trp Leu Glu Ser His Gln Asn Pro Gln Ser Gly Gly Lys
3185                3190                3195                3200

Leu Leu Tyr Trp Cys Lys His Ser Trp Pro Leu Thr Ser Leu Ser Gly
            3205                3210                3215

Asp Gln Gly Ala Arg Ala Arg Cys Ile Gly Ala Asn Arg Arg Gly Cys
            3220                3225                3230

Gln Arg Cys Asn Arg Cys Arg Cys Ala Pro Thr Gly Thr Leu Glu
            3235                3240                3245

Asn Ala Ala Val Val Gly Gly Arg Glu Ala Ile Val Leu Leu Glu Arg
            3250                3255                3260

Gln Gly Arg Gly Leu Pro Thr Gly Gly Asp Ser Arg Arg Cys Thr Trp
3265                3270                3275                3280

Thr Ser Arg Phe Leu Arg Arg Lys Pro Glu Glu Thr Arg Val Arg Gly
            3285                3290                3295

Ser Lys Cys Cys Val Ala Ala Ser Ser Ser Leu Ala Arg Phe Asp Gln
            3300                3305                3310

Gly Ala Arg Ser His Cys Ser Ile Asp Thr Glu Lys Met Lys Ala Phe
            3315                3320                3325

Ser Asp Ser Thr Pro Pro Gly Thr Thr Gly Trp Val Ala Val Tyr
            3330                3335                3340

Pro Gly Ser Arg Leu Val Leu Glu Pro Ala Gly Ala Ala Ala Asn Val
3345                3350                3355                3360

Val Leu Ala Leu Pro Ser Arg Pro Ser Leu Gln Lys Ser Arg Ile Arg
            3365                3370                3375

Asn Arg Val Val Leu Leu Val Ser Glu Trp Gln Gly Ser Glu Ser Tyr
            3380                3385                3390

Phe Phe Phe Phe Ala Ala Gln Met His Pro Val Leu Arg Gln Met Arg
            3395                3400                3405

Pro Gln Gln Gln Pro Pro Ser Gln Gln Gln Gln Gln Ser Gln Lys
            3410                3415                3420

Ala Val Pro Ala Thr Thr Ala Thr Ala Ala Val Ser Gly Ala Asp Ser
```

```
                    -continued
3425             3430             3435             3440

Pro Pro Met Ile Trp Thr Trp Lys Arg Ala Lys Asp Trp His Val Val
                3445             3450             3455

Arg Leu His Pro Ser Gly Ile Arg Glu Phe Asn Lys Lys Ile Leu Ala
                3460             3465             3470

Arg Arg Met Cys Pro Asn Arg Thr Tyr Leu Glu Thr Glu Ala Ala Arg
                3475             3480             3485

Ser Arg Arg Arg Cys Glu Leu Pro Ala Leu Thr Arg Val Val Ser Cys
                3490             3495             3500

Val Thr Val Trp Thr Glu Asp Glu Cys Cys Gly Thr Arg Ile Ser Lys
3505             3510             3515             3520

Leu Met Lys Gln Gly Ser Val Leu Pro Gly His Thr Trp Leu Gln Pro
                3525             3530             3535

Thr Leu Tyr Arg Leu Thr Ser Arg Gln Arg Lys Ser Val Thr Ser Lys
                3540             3545             3550

Ser Leu Leu Ile Ile Met Cys Glu Pro Leu Pro Ala Lys Lys Leu Pro
                3555             3560             3565

Leu Val Cys Ile Cys Gly Ile Trp Lys Leu Ser Phe Arg Thr Leu Leu
                3570             3575             3580

Ala Asn Leu Pro Pro Ser Cys Phe Trp Trp Cys Asn Thr Ala Glu Thr
3585             3590             3595             3600

Met Arg Leu Ser Glu Arg Arg Cys Thr Ser Pro Asn Pro Arg Gly Asp
                3605             3610             3615

Gly Cys Met Ile Leu Ser Thr Phe Tyr Arg Val Ser Cys Arg Ser Gly
                3620             3625             3630

Ala Trp Ala Trp Pro Arg Arg Trp Leu Pro Ser Ile Thr Arg Phe Ala
                3635             3640             3645

Trp Glu Asn Ile Thr Leu Ala Lys Ser Thr Arg Leu His Thr Phe Pro
                3650             3655             3660

Thr Arg Arg Arg Met Gly Ser Thr Cys Ala Arg Ser Arg Ser Pro Ala
3665             3670             3675             3680

Met Ile Leu Gly Cys Ile Ala Met Thr Glu Cys Ile Ala Arg Leu Ala
                3685             3690             3695

Pro Ala Gly Gly Ala Ser Ala Thr Gly Asn Cys Thr Val Cys Lys Glu
                3700             3705             3710

Leu Leu Glu Leu Glu Pro Arg Val Arg Ile Thr Ser Thr Trp Glu Leu
                3715             3720             3725

Thr Cys Ser Gly Ser Leu Val Ala Gly Leu Ala Pro Arg Arg Gln Asp
                3730             3735             3740

Val Ser Phe Leu Thr Lys Arg Met Lys Ala Arg Lys Arg Ala
3745             3750             3755             3760

Ser Thr Trp Lys Thr Asp Gly Thr Thr Arg Val Phe Cys Met Glu Gln
                3765             3770             3775

Gln Ala Pro Asp Pro Ala Met Arg Ala Ala Leu Gln Ser Gln Pro Ser
                3780             3785             3790

Gly Ile Asn Ser Ser Asp Asp Trp Thr Gln Ala Met Gln Arg Ile Met
                3795             3800             3805

Ala Leu Thr Thr Arg Asn Pro Glu Ala Phe Arg Gln Gln Pro Gln Ala
                3810             3815             3820

Asn Arg Leu Ser Ala Ile Met Glu Ala Val Val Pro Ser Arg Ser Asn
                3825             3830             3835             3840

Pro Thr His Glu Lys Val Leu Ala Ile Val Asn Ala Leu Val Glu Asn
                3845             3850             3855
```

-continued

Lys Ala Ile Arg Pro Asp Glu Ala Gly Leu Val Tyr Asn Ala Leu Leu
              3860                3865                3870

Glu Arg Val Ala Arg Tyr Asn Ser Ser Asn Val Gln Thr Asn Leu Asp
         3875                3880                3885

Arg Met Ile Thr Asp Val Arg Glu Ala Val Ser Gln Arg Glu Arg Phe
         3890                3895                3900

Gln Arg Asp Ala Asn Leu Gly Ser Leu Val Ala Leu Asn Ala Phe Leu
3905                3910                3915                3920

Ser Thr Gln Pro Ala Asn Val Pro Arg Gly Gln Gln Asp Tyr Thr Asn
              3925                3930                3935

Phe Leu Ser Ala Leu Arg Leu Met Val Ser Glu Val Pro Gln Ser Glu
              3940                3945                3950

Val Tyr Gln Ser Gly Pro Asp Tyr Phe Phe Gln Thr Ser Arg Gln Gly
              3955                3960                3965

Leu Gln Thr Val Asn Leu Ser Gln Ala Phe Lys Asn Leu Lys Gly Leu
              3970                3975                3980

Trp Gly Val His Ala Pro Val Gly Glu Arg Ala Thr Val Ser Ser Leu
3985                3990                3995                4000

Leu Thr Pro Asn Ser Arg Leu Leu Leu Leu Val Ala Pro Phe Thr
              4005                4010                4015

Asp Ser Gly Ser Ile Asp Arg Asn Ser Tyr Leu Gly Tyr Leu Leu Asn
              4020                4025                4030

Leu Tyr Arg Glu Ala Ile Gly Gln Ser Gln Val Asp Glu Gln Thr Tyr
              4035                4040                4045

Gln Glu Ile Thr Gln Val Ser Arg Ala Leu Gly Gln Glu Asp Thr Gly
              4050                4055                4060

Ser Leu Glu Ala Thr Leu Asn Phe Leu Leu Thr Asn Arg Ser Gln Lys
4065                4070                4075                4080

Ile Pro Pro Gln Tyr Ala Leu Thr Ala Glu Glu Arg Ile Leu Arg
              4085                4090                4095

Tyr Val Gln Gln Ser Val Gly Leu Phe Leu Met Gln Glu Gly Ala Thr
              4100                4105                4110

Pro Thr Ala Ala Leu Asp Met Thr Ala Arg Asn Met Glu Pro Ser Met
              4115                4120                4125

Tyr Ala Ser Asn Arg Pro Phe Ile Asn Lys Leu Leu Asp Tyr Leu His
              4130                4135                4140

Arg Ala Ala Ala Met Asn Ser Asp Tyr Phe Thr Asn Ala Ile Leu Asn
4145                4150                4155                4160

Pro His Trp Leu Pro Pro Gly Phe Tyr Thr Gly Glu Tyr Asp Met
              4165                4170                4175

Pro Asp Pro Asn Asp Gly Phe Leu Trp Asp Asp Val Asp Ser Asp Val
              4180                4185                4190

Phe Ser Pro Leu Ser Asp His Arg Thr Trp Lys Lys Glu Gly Gly Asp
              4195                4200                4205

Arg Met His Ser Ser Ala Ser Leu Ser Gly Val Met Gly Ala Thr Ala
              4210                4215                4220

Ala Glu Pro Glu Ser Ala Ser Pro Phe Pro Ser Leu Pro Phe Ser Leu
4225                4230                4235                4240

His Ser Val Arg Ser Ser Glu Val Gly Arg Ile Ser Arg Pro Ser Leu
              4245                4250                4255

Met Gly Glu Glu Glu Tyr Leu Asn Asp Ser Leu Leu Arg Pro Ala Arg
              4260                4265                4270

```
Glu Lys Asn Phe Pro Asn Asn Gly Ile Glu Ser Leu Val Asp Lys Met
        4275                4280                4285

Ser Arg Trp Lys Thr Tyr Ala Gln Asp His Arg Asp Glu Pro Gly Ile
    4290                4295                4300

Met Gly Ile Thr Ser Arg Ala Ser Arg Arg Gln Arg His Asp Arg
4305                4310                4315                4320

Gln Arg Gly Leu Val Trp Asp Asp Glu Asp Ser Ala Asp Asp Ser Ser
                4325                4330                4335

Val Leu Asp Leu Gly Gly Arg Gly Arg Gly Asn Pro Phe Ala His Leu
            4340                4345                4350

Arg Pro Arg Leu Gly Gly Met Leu Lys Lys Ile Lys Lys Lys Leu Thr
        4355                4360                4365

Lys Ala Met Ala Thr Ser Val Arg Ser Phe Phe Phe Ile Ile Cys Val
    4370                4375                4380

Tyr Asn Glu Ala Ser Arg Ala Arg Arg Ser Gly Gly Val Ser Gly Gly
4385                4390                4395                4400

Ser Ser Ser Phe Val Arg Glu Arg Asp Ala Ala Ala Gly Asp Gly
                4405                4410                4415

Gly Asp Ala Ile Pro Thr Gly Gly Ser Leu Cys Ala Ser Ala Ile Pro
            4420                4425                4430

Gly Thr Tyr Gly Gly Gln Lys Gln His Ser Leu Phe Gly Thr Gly Thr
        4435                4440                4445

Ser Val Arg Tyr His Gln Val Val Ser Gly Gly Gln Gln Val Gly Gly
    4450                4455                4460

His Cys Phe Ser Glu Leu Ser Glu Pro Gln Gln Leu Leu Asp His Gly
4465                4470                4475                4480

Gly Ala Lys Gln Leu Tyr Pro Tyr Gly Ser Gln His Pro Asp His Leu
                4485                4490                4495

Thr Ile Ala Val Gly Arg Ser Ala Lys Asp His His Ala Tyr His Ala
            4500                4505                4510

Lys Arg Glu Arg Val Tyr Val Gln Val Gln Ser Ala Cys Asp Gly Val
        4515                4520                4525

Gln Lys Thr Ser Arg Arg Cys Cys Ser Trp Gly Tyr Leu Ser Gln Ala
    4530                4535                4540

Gly Tyr Phe Glu Ile Val Val Arg Val Tyr Phe Ala Arg Arg Gln Leu
4545                4550                4555                4560

Phe Ser Tyr Tyr Asp Tyr Phe Asp Glu Gln Cys His His Arg Leu Leu
                4565                4570                4575

Glu Ser Gly Thr Glu Trp Ser Ala Lys His Trp Cys Val Arg His Gln
            4580                4585                4590

Glu Leu Gln Ala Gly Met Gly Ser Arg Asn Gln Val Asp His Ala Trp
        4595                4600                4605

Ser Val Tyr Val Ser Leu Pro Ser His Cys Leu Thr Ala Trp Leu Arg
    4610                4615                4620

Ser Gly Phe Tyr Arg Glu Ser Phe Glu Gln Pro Ser Trp Tyr Gln Lys
4625                4630                4635                4640

Lys Thr Ala Ile Ser Arg Gly Phe Asp Phe Val Arg Phe Arg Arg Trp
                4645                4650                4655

Tyr Ser Gly Pro Leu Gly Cys Arg Cys Leu Glu Gln Glu Arg Thr Lys
            4660                4665                4670

Ser Gln Asn Arg Ser Cys Tyr Ser Cys Cys Arg Ser Gly Lys His Ser
        4675                4680                4685

Cys Gln Arg Leu Tyr Lys Gly Cys Arg Trp Arg Gly Gln Arg Arg Gln
```

-continued

```
                4690                4695                4700
Phe Cys Ala Asn Thr Cys Ser Asp Cys Arg Ile Ile Ile Gly Arg Cys
4705                4710                4715                4720

Val Arg Asn Gly Arg Glu Thr His Tyr Ser Thr Cys Arg Lys Arg Glu
                4725                4730                4735

Lys Leu Cys Val Gly Arg Gln Asn Gln His Ser Leu Ser Gln Leu Val
                4740                4745                4750

Ser Phe Val Gln Leu Trp Arg Ser Lys Arg Ser Ala Phe Leu Asp
                4755                4760                4765

Ile Ala His His Leu Arg Cys His Leu Arg Ser Arg Ala Gly Leu Leu
                4770                4775                4780

Val Ala Ser Arg His Asp Glu Gly Ser Cys His Phe Pro Leu His Thr
4785                4790                4795                4800

Ser Gln Leu Pro Cys Gly Gly Cys Arg Ala Tyr Ala Arg Leu Leu Lys
                4805                4810                4815

Glu Leu Leu Gln Arg Thr Ser Cys Val Leu Pro Ala Ala Pro Pro Val
                4820                4825                4830

His Leu Ala Tyr Ala Arg Leu Gln Pro Leu Ser Glu Pro Asp Phe Asn
                4835                4840                4845

Pro Ser Ala Gly Ala His His Tyr His Arg Gln Lys Arg Ser Cys Ser
                4850                4855                4860

His Arg Ser Arg Asp Pro Ala Val Ala Gln Gln Tyr Pro Gly Ser Pro
4865                4870                4875                4880

Thr Cys Asp Arg Tyr Arg Gln Thr Pro His Leu Ser Leu Arg Val Gln
                4885                4890                4895

Gly Thr Gly His Ser Arg Thr Ala Arg Pro Phe Lys Pro His Phe Leu
                4900                4905                4910

Lys Lys Lys Lys Met Ser Ile Leu Ile Ser Pro Ser Asn Asn Thr Gly
                4915                4920                4925

Trp Gly Leu Arg Ala Pro Ser Lys Met Tyr Gly Gly Ala Arg Lys Arg
                4930                4935                4940

Ser Thr Gln His Pro Val Arg Val Arg Gly His Phe Arg Ala Pro Trp
4945                4950                4955                4960

Gly Ala Leu Lys Gly Arg Thr Arg Val Arg Thr Thr Val Asp Val
                4965                4970                4975

Ile Asp Gln Val Val Ala Asp Ala Arg Asn Tyr Thr Pro Thr Ala Pro
                4980                4985                4990

Thr Ser Thr Val Asp Ala Val Ile Asp Ser Val Val Ala Asp Ala Arg
                4995                5000                5005

Asn Tyr Ala Arg Arg Lys Ser Arg Arg Arg Ile Ala Arg Arg His
     5010                5015                5020

Arg Ala Thr Thr Ala Met Arg Ala Ala Arg Ala Leu Leu Arg Ala
5025                5030                5035                5040

Arg Arg Val Gly Arg Arg Ala Met Leu Arg Ala Ala Arg Arg Ala Ala
                5045                5050                5055

Ser Gly Ala Ser Ala Gly Arg Ser Arg Arg Gln Ala Ala Ala Phe Ala
                5060                5065                5070

Ala Ala Thr Ile Ala Asp Met Ala Gln Ser Arg Arg Gly Asn Val Tyr
                5075                5080                5085

Trp Val Arg Asp Ala Ala Thr Gly Gln Arg Val Pro Val Arg Thr Arg
                5090                5095                5100

Pro Pro Arg Thr Lys Ile Leu Ser Ser Leu Arg Cys Cys Val Pro Ala
5105                5110                5115                5120
```

-continued

```
Ala Arg Met Ser Lys Arg Lys Tyr Lys Glu Glu Met Leu Gln Val Ile
            5125                5130                5135

Ala Pro Glu Val Tyr Gly Gln Pro Leu Lys Asp Glu Lys Lys Pro Arg
        5140                5145                5150

Lys Ile Lys Arg Val Lys Lys Asp Lys Lys Glu Glu Asp Gly Asp
    5155                5160                5165

Asp Gly Leu Ala Glu Phe Val Arg Glu Phe Ala Pro Arg Arg Val
5170                5175                5180

Gln Trp Arg Gly Arg Lys Val Arg His Val Leu Arg Pro Gly Thr Ser
5185                5190                5195                5200

Val Val Phe Thr Pro Gly Glu Arg Ser Ser Ala Thr Phe Lys Arg Ser
            5205                5210                5215

Tyr Asp Glu Val Tyr Gly Asp Asp Ile Leu Glu Gln Ala Ala Asp
        5220                5225                5230

Arg Leu Gly Glu Phe Ala Tyr Gly Lys Arg Ser Arg Ile Thr Ser Lys
            5235                5240                5245

Asp Glu Thr Val Ser Ile Pro Leu Asp His Gly Asn Pro Thr Pro Ser
        5250                5255                5260

Leu Lys Pro Val Thr Leu Gln Gln Val Leu Pro Val Thr Pro Arg Thr
5265                5270                5275                5280

Gly Val Lys Arg Glu Gly Glu Asp Leu Tyr Pro Thr Met Gln Leu Met
            5285                5290                5295

Val Pro Lys Arg Gln Lys Leu Glu Asp Val Leu Glu Lys Val Lys Val
            5300                5305                5310

Asp Pro Asp Ile Gln Pro Glu Val Lys Val Arg Pro Ile Lys Gln Val
        5315                5320                5325

Ala Pro Gly Leu Gly Val Gln Thr Val Asp Ile Lys Ile Pro Thr Glu
        5330                5335                5340

Ser Met Glu Val Gln Thr Glu Pro Ala Lys Pro Thr Ala Thr Ser Thr
5345                5350                5355                5360

Glu Val Gln Thr Asp Pro Trp Met Pro Met Pro Ile Thr Thr Asp Ala
            5365                5370                5375

Ala Gly Pro Thr Arg Arg Ser Arg Arg Lys Tyr Gly Pro Ala Ser Leu
            5380                5385                5390

Leu Met Pro Asn Tyr Val Val His Pro Ser Ile Ile Pro Thr Pro Gly
        5395                5400                5405

Tyr Arg Gly Thr Arg Tyr Tyr Arg Ser Arg Asn Ser Thr Ser Arg Arg
        5410                5415                5420

Arg Arg Lys Thr Pro Ala Asn Arg Ser Arg Arg Arg Arg Thr Ser
5425                5430                5435                5440

Lys Pro Thr Pro Gly Ala Leu Val Arg Gln Val Tyr Arg Asn Gly Ser
            5445                5450                5455

Ala Glu Pro Leu Thr Leu Pro Arg Ala Arg Tyr His Pro Ser Ile Ile
        5460                5465                5470

Thr Ser Met Leu Pro Leu Pro Pro Cys Arg Tyr Gly Pro His Leu Ser
        5475                5480                5485

Pro Ser Arg Ser His His Trp Leu Pro Arg Lys Lys Leu Ala Pro Lys
        5490                5495                5500

Arg Asp Val Gly Thr Arg Asn Ala Thr Leu Gln Ala Thr Ala Cys Tyr
5505                5510                5515                5520

Pro Gln Ala Ile Ala Gly Trp Phe Phe Thr Ser Leu Asn Ser Asn Tyr
        5525                5530                5535
```

-continued

Arg Cys Cys Asn Trp Arg Asp Thr Arg His Ser Phe Arg Gly Gly Ser
        5540                5545                5550

Gly Leu Ala Thr Thr Leu Thr Leu Glu Lys Asn Val Ile Lys Lys Lys
        5555                5560                5565

Lys Tyr Asn Gly Leu His Ser Trp Ser Cys Asp Tyr Val Phe Leu Glu
        5570                5575                5580

Met Glu Asp Ile Asn Phe Ser Ser Leu Ala Pro Arg His Gly Thr Lys
5585                5590                5595                5600

Pro Tyr Met Gly Thr Trp Ser Asp Ile Gly Thr Ser Gln Leu Asn Gly
            5605                5610                5615

Gly Ala Phe Asn Trp Ser Ser Ile Trp Ser Gly Leu Lys Asn Phe Gly
        5620                5625                5630

Ser Thr Ile Lys Thr Tyr Gly Asn Lys Ala Trp Asn Ser Ser Thr Gly
        5635                5640                5645

Gln Ala Leu Arg Asn Lys Leu Lys Asp Gln Asn Phe Gln Gln Lys Val
5650                5655                5660

Val Asp Gly Ile Ala Ser Gly Ile Asn Gly Val Val Asp Leu Ala Asn
5665                5670                5675                5680

Gln Ala Val Gln Lys Lys Ile Asn Ser Arg Leu Asp Pro Pro Pro Ala
        5685                5690                5695

Thr Pro Gly Glu Met Gln Val Glu Glu Glu Ile Pro Pro Glu Lys
        5700                5705                5710

Arg Gly Asp Lys Arg Pro Arg Pro Asp Leu Glu Glu Thr Leu Val Thr
        5715                5720                5725

Arg Val Asp Glu Pro Pro Ser Tyr Glu Glu Ala Thr Lys Leu Gly Met
        5730                5735                5740

Pro Thr Thr Arg Pro Ile Ala Pro Met Ala Thr Gly Val Met Lys Pro
5745                5750                5755                5760

Ser Gln Leu His Arg Pro Val Thr Leu Asp Leu Pro Pro Pro Ala
            5765                5770                5775

Ala Thr Ala Val Pro Ala Ser Lys Pro Val Ala Ala Pro Lys Pro Val
        5780                5785                5790

Ala Val Ala Arg Ser Arg Pro Gly Gly Ala Pro Arg Pro Asn Ala His
        5795                5800                5805

Trp Gln Asn Thr Leu Asn Ser Ile Val Gly Leu Gly Val Gln Ser Val
        5810                5815                5820

Lys Arg Arg Arg Cys Phe Leu Asn Met Glu Arg Leu Thr Cys Leu Ser
5825                5830                5835                5840

Val Tyr Met Cys His Tyr Thr Pro Ser Gln Gln Arg Lys Lys Gly
            5845                5850                5855

Arg Gly Arg Ala Ser Thr Leu Ser Tyr Phe Gln Asp Gly His Pro Ile
        5860                5865                5870

Asp Ala Ala Pro Met Gly Ile His Ala His Arg Arg Thr Gly Cys Phe
        5875                5880                5885

Gly Val Pro Glu Ser Gly Ser Gly Ala Val Arg Pro Arg His Arg His
        5890                5895                5900

Leu Leu Gln Ser Gly Lys Val Lys Ser His Arg Ser Ala Asp Pro Arg
5905                5910                5915                5920

Cys Asp His Arg Pro Pro Ala Ala His Val Ala Leu Arg Ala Arg Pro
            5925                5930                5935

Gly Gly Gln Tyr Ile Leu Leu Gln Ser Ala Val His Pro Gly Arg Gly
        5940                5945                5950

Arg Gln Gln Ser Ala Gly Tyr Gly Gln His Val Leu His Gly Cys Val

-continued

```
            5955                5960                5965
Gly Gln Arg Ser Gln Phe Gln Thr Leu Phe Trp Tyr Gly Leu Gln Leu
    5970                5975                5980
Pro Gly Ser Arg Arg Ser Lys Tyr Ile Ser Val Asp Cys Arg Arg Cys
5985                5990                5995                6000
Lys Lys Tyr Asn Trp Gly Thr Arg Asn Arg Arg Gly Asn Gln Tyr Tyr
            6005                6010                6015
Tyr Leu His Phe Trp Gln Cys Ser Cys Lys Ser Ser Asn Tyr Lys Arg
            6020                6025                6030
Arg Thr Pro Ser Arg Phe Gly Ser Phe Arg Arg Lys Thr Asp Leu Cys
            6035                6040                6045
Asn Ile Ser Ala Arg Thr Ser Ala Gly Arg Asn Leu Asp Pro Trp Lys
            6050                6055                6060
Asn Arg Lys Val Trp Arg Gln Gly Ser Gln Thr Arg Tyr Asp Glu Thr
6065                6070                6075                6080
Met Leu Arg Val Leu Cys Gln Thr Tyr Cys Glu Arg Arg Ser Gly Lys
            6085                6090                6095
Thr Lys Asn Asn Gly Ala Ala Lys Ser Glu Ser Arg Ile Tyr Arg His
            6100                6105                6110
Gly Val Phe Cys Gly Ile Ala Glu Asn Lys Leu Lys Ser Asn Cys His
            6115                6120                6125
Val Cys Arg Lys Cys Lys Phe Gly Asn Ser Arg His Ser Cys Ser Val
            6130                6135                6140
Gln Thr Trp Asn Arg Arg His Lys Phe Arg Ser Phe Gly Thr Thr Ile
6145                6150                6155                6160
Tyr Ala Gln Gln Thr Gln Leu His Trp Leu Gln Arg Leu Tyr Trp Thr
            6165                6170                6175
Tyr Val Leu Gln Tyr Trp His Gly Gly Ala Gly Trp Ser Ser Val Ser
            6180                6185                6190
Val Lys Cys Ser Gly Leu Ala Gly Gln Lys His Arg Thr Phe Leu Pro
            6195                6200                6205
Thr Leu Ala Leu Ser Gly Arg Gln Asn Gln Ile Leu His Val Glu Ser
            6210                6215                6220
Gly Cys Gly Gln Leu Ser Cys Thr Cys Tyr Lys Ser Trp Cys Gly Arg
6225                6230                6235                6240
Thr Ser Gln Leu Leu Phe Ser Thr Gly Arg His Arg Cys Ser Asn Asn
            6245                6250                6255
Gln Leu Gln Ile Asn Ser Ser Lys Trp Arg Gln Cys Ala Leu Glu Gly
            6260                6265                6270
Thr Ser Lys Trp Asn Lys Asp Arg Thr Gly Phe Val Cys His Gly Asn
            6275                6280                6285
Pro Ser Ser Gln Ser Met Ala Lys Phe Pro Leu Phe Gln Cys Gly Ser
            6290                6295                6300
Ile Ser Pro Arg Leu Val Gln Ile His Pro Val Gln Cys His Ser Ser
6305                6310                6315                6320
Arg Lys Gln Lys His Leu Arg Leu His Glu Arg Ala Gly Gly Ala Ala
            6325                6330                6335
Ile Ser Ser Arg His Leu Cys Glu His Trp Cys Gln Val Val Ser Gly
            6340                6345                6350
Cys His Gly Gln Cys Gln Pro Ile Gln Pro Pro Arg Trp Leu Ala
            6355                6360                6365
Leu Pro Ile His Ala Ser Gly Arg Thr Leu Cys Ala Phe Pro His Thr
            6370                6375                6380
```

```
Ser Ala Ser Lys Ile Leu Arg Cys Lys Pro Ala Ala Ser Pro Arg Leu
6385                6390                6395                6400

Leu His Leu Val Glu Leu Glu Gly Cys Glu His Gly Ser Thr Glu Phe
                6405                6410                6415

Pro Arg Arg Pro Ala Gly Arg Trp Arg Gln His Gln Phe His Glu His
            6420                6425                6430

Gln Pro Leu Cys Tyr Phe Phe Pro His Gly Ser Gln His Arg Phe His
        6435                6440                6445

Pro Ser His Ala Ala Glu His Gln Ser Val Ile Gln Arg Leu Pro Ile
    6450                6455                6460

Cys Ser His Ala Leu Pro His Ser Cys Gln Cys Asn Gln Tyr Ser His
6465                6470                6475                6480

Phe His Ser Phe Ser Gln Leu Gly Gly Phe Gln Arg Leu Val Ile Tyr
                6485                6490                6495

Gln Thr Glu Asn Gln Arg Asn Ser Leu Phe Gly Val Trp Ile Pro Leu
            6500                6505                6510

Leu Cys Leu Phe Trp Phe Tyr Ser Leu Pro Gly Trp Tyr Leu Leu Pro
        6515                6520                6525

Glu Pro His Phe Glu Gly Phe His Val Leu Phe Ser Glu Leu Ala
    6530                6535                6540

Trp Lys Gln Val Thr Ile Ser Arg Ile Asn Lys Ala His Cys Gly Trp
6545                6550                6555                6560

Arg Arg Leu Gln Arg Ser Pro Met Gln His Asp Gln Arg Leu Val Leu
                6565                6570                6575

Gly Thr Asp Ala Arg Gln Leu Gln His Arg Leu Ser Gly Leu Leu His
            6580                6585                6590

Ser Arg Arg Ile Gln Arg Ser His Val Phe Ile Phe Gln Lys Leu Pro
        6595                6600                6605

Ala His Glu Gln Ala Gly Gly Gln Leu Gln Arg Leu Gln Gly Arg
    6610                6615                6620

Arg His Thr Leu Pro Thr Gln Gln Leu Trp Leu Cys Gly Leu His Gly
6625                6630                6635                6640

Ser Asp His Ala Pro Arg Ser Thr Leu Ser Arg Leu Ser Leu Ser Thr
                6645                6650                6655

His Trp Asn Asn Cys Arg Lys Cys Tyr Ala Glu Lys Val Leu Val Gln
            6660                6665                6670

Asn His Val Ala His Thr Val Leu Glu Gln Leu His Val Tyr Gly Gly
        6675                6680                6685

Pro Tyr Arg Leu Gly Thr Glu Tyr Ala Leu Cys Gln Leu Ser Ser Cys
    6690                6695                6700

Ser Gly His Asp Leu Gly Gly Ser His Gly Ala His Pro Ala Leu Ser
6705                6710                6715                6720

Ser Leu Arg Ser Phe Arg Arg Gly Gln Ser Ala Ser Ala Thr Pro Arg
                6725                6730                6735

His His Arg Gly Ser Leu Pro Ala Tyr Thr Val Leu Gly Arg Arg Tyr
            6740                6745                6750

His Val Arg Ser Phe Leu Leu Leu Ala Asn Ser Ser Cys Asn His Gly
        6755                6760                6765

Leu Arg Ile Pro Lys Arg Leu Gln Arg Ala Arg Ala Gln Ser His Cys
    6770                6775                6780

Pro Arg Pro Gly Leu Arg Thr Leu Phe Phe Gly Asn Leu Arg Ala Leu
6785                6790                6795                6800
```

-continued

```
Pro Gly Val His Gly Pro Arg Ala Arg Leu Cys His Cys Lys Tyr Gly
            6805                6810                6815

Arg Thr Asp Gly Gly Arg Ala Leu Val Gly Phe Arg Leu Glu Pro Thr
        6820                6825                6830

Phe His Leu Leu Pro Phe Ser Phe Trp Ile Leu Gly Ser Ser Gln Thr
    6835                6840                6845

Asp Leu Pro Val Ile Gly Ser Pro Ala Pro Gln Arg Ser Cys Tyr Gln
6850                6855                6860

Gly Pro Leu Tyr Tyr Ala Gly Lys Ile Tyr Pro Asp Arg Ala Gly Ser
6865                6870                6875                6880

Pro Phe Cys Arg Leu Arg Thr Phe Leu Leu His Val Pro Ser Arg Leu
            6885                6890                6895

Cys Ala Leu Ala Pro Ser His Gly Arg Lys Pro His His Glu Ile Ala
        6900                6905                6910

Asn Trp Ser Ala Lys Gln His Ala Ser Phe Ser Ser Pro Ala His Pro
    6915                6920                6925

Val Gln Ser Lys Ser Thr Leu Pro Phe Ser Tyr Pro Phe Ala Leu Phe
6930                6935                6940

Ser Leu Pro Ser Tyr Thr His Arg Lys Gly His Cys Val Arg Pro Tyr
6945                6950                6955                6960

Gly Cys Ser Ile Met Thr His Val Asn Asn Val Phe Asn Lys His His
            6965                6970                6975

Phe Ile Phe Leu His Val Ser Arg Leu Cys Ile Thr Tyr Leu Phe Thr
        6980                6985                6990

Ser Arg Met Gly Ser Asp Glu Asn Gln Asn Asp Pro Gln Ala Val Ile
    6995                7000                7005

Arg Cys Gly Thr Asp Thr Trp Val Ala Thr Ile Arg Glu Ser Pro Thr
7010                7015                7020

Trp Glu Pro Val Tyr Arg Ala Gly Cys His Ser Thr Ala Phe Trp Ser
7025                7030                7035                7040

Ala Ala Lys Leu Gln Ala Gly Gln Glu Pro Lys Ser Asn His Asn Asp
            7045                7050                7055

Gln Cys Phe Glu Arg Glu Ser Cys Gly Thr Pro Asp Cys Ser Thr Glu
        7060                7065                7070

Thr Pro Ser Ala Thr Asp Val Ser Arg Leu Pro Ala Arg Trp Asp Leu
    7075                7080                7085

Gln Ser Cys Pro His Pro Asp Leu Gln His Trp Gln Cys Thr Gly Ser
7090                7095                7100

Ser Cys Arg Ser Ala Tyr Pro Trp Arg Ala Pro Asn Ala Cys Gly Cys
7105                7110                7115                7120

Asn Arg Ser Ala Gly Gly Ser Val Ser Ser Trp Pro Asp Pro Val Phe
            7125                7130                7135

Leu Asp Thr Arg Leu Ser Lys His His Ile Ala Lys Pro Ala Gly Leu
        7140                7145                7150

Tyr Tyr Pro Arg Tyr Lys Thr Ser Arg Arg Thr Cys Ser Lys Thr Gly
    7155                7160                7165

Leu His Ser Arg His His Ser His Ser Ser Gly Arg His Cys Leu Phe
    7170                7175                7180

Ala Pro His Phe Cys Pro Ser Gly Phe Gly Phe Trp Phe Ala Arg Asp
7185                7190                7195                7200

Ser Pro Leu Arg Leu Val Val Arg Ser Arg Trp Pro His Pro Ser Arg
            7205                7210                7215

Ser Ala Pro Ser Glu Ser Tyr Cys His Ala Gly Thr Ser Ala Cys Pro
```

-continued

```
                    7220              7225              7230
His Asn His Cys Ser His Glu Ala Thr Thr His Ser Leu Tyr Ile Pro
        7235              7240              7245
Asn Tyr Gly Gly Arg Ser Glu Lys Lys Asn Val Ser Phe Pro Ala Glu
        7250              7255              7260
Ile Phe Pro Ser Ser Cys Ser Val Ser Cys Asp Lys Leu Thr Gly Cys
7265              7270              7275              7280
Leu Gly Ala Pro Arg Leu Arg Thr Gly Asp Arg Cys Ala Cys Ile Val
            7285              7290              7295
Arg Val Ala Gln Ala Leu Val Lys Arg Phe Val Arg Tyr Pro Ala Cys
            7300              7305              7310
Thr Ser Pro Ser Ala Asp Thr Ser Leu Pro Cys Leu Ser Pro Lys Gln
        7315              7320              7325
Thr Pro Gly Ala Ser Ser Asp Ser Gln Cys Arg Gln Gln Leu Leu Pro
        7330              7335              7340
Glu Gly His Leu Arg Ser Ser Gln Cys Phe Phe Cys His Pro Ser Gln
7345              7350              7355              7360
Arg Cys Ala Arg Ala Gly Ser Asn Pro Leu Leu Gln Val Ala Pro Leu
            7365              7370              7375
Leu Phe Leu Leu Arg Cys Leu Asp Cys Leu Ala Trp Gly Tyr Val Trp
            7380              7385              7390
Ser Ser Leu Ala Ser Phe Trp Gly Val Ser Glu Glu Asp Cys Arg
        7395              7400              7405
Ser Val Pro Glu Thr Gly Arg Ile Val Thr Phe Arg Ser Pro Leu Pro
        7410              7415              7420
Thr Asp Cys Arg Lys Asn Leu Thr Pro His Gly Asp Arg Cys Phe Ser
7425              7430              7435              7440
Ser Gly Ala Glu Val Glu Ala Ile Ala Lys Gly Cys Gly Pro Thr Trp
            7445              7450              7455
Lys Ala Asp Asp Trp Gln Asn Pro Phe Arg Val Arg Gly Cys Ala Pro
            7460              7465              7470
Cys Gly Gly Arg Leu Thr Asp Phe Leu Arg Gly Trp Pro Leu Cys Ser
            7475              7480              7485
Pro Arg Gln Arg Asn Asn Arg His Gly Asn Ser Ala Ile Ala Val Asn
        7490              7495              7500
Ile Ala Thr Ser Ala Ile Thr Ser Arg Pro Gln Arg Arg Gly Lys Gly
7505              7510              7515              7520
Ala Glu Leu Lys His Ser Thr Ala Gln Ser Cys His His Leu Tyr Pro
            7525              7530              7535
Arg Arg Gly Gly Arg Ile Ser His Ala Glu Lys Ser Glu Arg Val
            7540              7545              7550
Asp Arg His Arg Ala Arg Pro Gly Leu Cys Asp Thr Gly Gly Thr Arg
        7555              7560              7565
Gly Arg Val Glu Thr Leu Ser Arg Glu Arg Gly Lys Leu Pro Lys Thr
        7570              7575              7580
Thr Ser Arg Leu Ser Pro Arg Cys Trp Lys Gly Ser Glu His Arg Leu
7585              7590              7595              7600
Pro His Arg Ala Arg Gly Arg Ala Pro Thr Ser Ser Lys Thr Val
            7605              7610              7615
Ala His Ser Gln Gly Cys Ile Ile Gly Gln Asn Ser Ala His Gln Cys
        7620              7625              7630
Gly Arg Ala Gln Pro Arg Leu Arg Ala Pro Leu Phe Thr Ser Tyr Ser
            7635              7640              7645
```

```
Pro Gln Thr Ser Ala Lys Arg His Leu Arg Ala Lys Ser Ser Leu Lys
    7650                7655                7660

Leu Leu Ser Ser Phe Cys Cys Ala Arg Ser Thr Gly Tyr Leu Ser His
7665                7670                7675                7680

Leu Phe Lys Ser Lys Asn Ser Ser Leu Leu Pro Arg Ser His Pro Arg
                7685                7690                7695

Arg Cys Pro Thr Gln Ser Gly Thr Trp Phe Thr Leu Thr Tyr Ser Phe
            7700                7705                7710

Leu Gly Arg Gly Ser Lys Asp Leu Arg Gly Ser Gly Gln Asp Ser Gly
        7715                7720                7725

Arg Lys Cys Ser Ala Lys Gly Arg Lys Trp His Gly Ala Ser Gln Arg
    7730                7735                7740

Ser Gly Gly Ile Gly Arg Arg Cys Gln Thr Arg Ser Thr Gln Ala Lys
7745                7750                7755                7760

His Arg Gly His Thr Leu Arg Ile Ser Arg Cys Gln Pro Ala Pro Ser
                7765                7770                7775

His Asp Gly Gly His Gly Pro Val Thr His Ala Arg Lys Ser Pro Phe
            7780                7785                7790

Arg Arg His Ala Pro Arg Cys Leu Gly Thr Ser Gly Gln Ala Ala Asn
        7795                7800                7805

Pro Met Ala Gly His Arg Leu Ser Gln Gly Phe Gly Arg Ala Ser Gln
    7810                7815                7820

Ala Tyr Asp Gly Arg Gly Ala Gly Tyr Arg Arg Thr Arg Val Ser Pro
7825                7830                7835                7840

Thr Phe Leu Tyr Arg Phe Arg Asn Leu Ala Gln Thr Arg Arg Glu Ser
                7845                7850                7855

Ala Leu His Phe Thr Arg Leu Cys Ala Ala Gly Met Gln Asp Ile Arg
            7860                7865                7870

Gly Thr His Gln Pro Gly Phe Leu His Gly Tyr Ser Ala Glu Ser Pro
        7875                7880                7885

Arg Thr Lys Arg Ala Ala Gln His Pro Glu Gly Gly Ser Pro Leu
    7890                7895                7900

His Pro Arg Leu Cys Leu Ser Val Pro Val Pro Asn Val Ala Asn Arg
7905                7910                7915                7920

His Gly Cys Met Ala Ala Met Phe Arg Arg Thr Glu Leu Glu Arg Ala
                7925                7930                7935

Gln Ala Leu Thr Glu Ile Ser Gly Ser Val Asp Arg Val Arg Arg Ala
            7940                7945                7950

His Arg Arg Phe Arg Pro Gly Arg Pro His Leu Pro Arg Ala Ser Gln
        7955                7960                7965

Gly Tyr Phe Ala Lys Arg Ile Ala Leu Tyr Glu Pro Glu His Ala Gln
    7970                7975                7980

Phe Ser Leu Phe His Pro Gly Thr Leu Arg Tyr Pro Ala Arg His Leu
7985                7990                7995                8000

Leu Arg Thr Ala Leu Arg Leu Cys Ala Ser His Leu Pro Arg Val Pro
                8005                8010                8015

Pro Ala Ala Met Glu Ser Leu Leu Pro Val Pro Ser Gly Gln Leu Ser
            8020                8025                8030

Leu Leu Pro Leu Gly Cys Asp Arg Gly Cys Glu Arg Arg Leu Ala
        8035                8040                8045

Gly Val Ser Leu Pro Leu Gln Ser Val His Ala Pro Pro Val Pro Ser
    8050                8055                8060
```

-continued

```
Leu Gln Pro Pro Val Asp Glu Arg Asn Pro Asp Asn Arg His Leu Ile
8065                8070                8075                8080

Ala Arg Pro Gln Gln Pro Arg Arg Trp Val Phe Ser Trp Ala Lys Phe
            8085                8090                8095

Lys Thr Asp Pro Gly Thr Val Asp Leu Arg Leu Leu Ala Gln Val Cys
            8100                8105                8110

Ser Gly Arg Leu Pro Pro Leu Asn Gln Val Leu Gly Pro Ile Thr Ala
        8115                8120                8125

Ser Lys Gly Arg Thr Phe Gly Leu Arg His His Pro Gly Gly Asn Ser
        8130                8135                8140

Gly Pro Ile Ala Ser His Pro Lys Ile Pro Pro Arg Ile Ser Thr Glu
8145                8150                8155                8160

Lys Gly Gly Gly Leu Pro Pro Asp Arg Arg Gly Thr Gln His Lys
            8165                8170                8175

Val Pro Ser Gly Cys Pro Asn Asp Glu Lys Thr Arg Ser Arg Cys Ser
            8180                8185                8190

Arg Arg Pro Gln Lys Ile Trp Arg Lys Ile Gly Thr Val Arg Gln Arg
        8195                8200                8205

Arg Arg Arg Arg Thr Val Trp Arg Thr Val Trp Arg Lys Thr Val Trp
        8210                8215                8220

Arg Arg Lys Thr Arg Arg Gln Arg Arg Trp Lys Lys Pro Pro Thr Asn
8225                8230                8235                8240

Ser Tyr Pro Arg Leu Arg Arg Gln Ala Thr Ala Leu Pro Ser Pro Leu
            8245                8250                8255

Arg Val Glu Glu Pro Gly Gly Val Pro Ala Val Asp Gly Thr Arg Pro
            8260                8265                8270

Asp Ala Ser Arg Thr Gln Pro Ala Leu Pro Arg Pro Val Arg Arg Ile
        8275                8280                8285

Gly Arg Asp Thr Ser Pro Gly Gly Ile Arg Met Pro Ser Ser Pro
        8290                8295                8300

Ala Cys Met Ser Ala Gly Ala Thr Tyr Pro Ser Arg Gly Ala Thr Cys
8305                8310                8315                8320

Tyr Ser Thr Met Gly Thr Phe Arg Ala Met Phe Cys Ile Thr Thr Val
            8325                8330                8335

Thr Ser Thr Ala Pro Thr Ile Ala Ser Lys Ser Arg Gln Ser Arg Gln
            8340                8345                8350

Ile Lys Thr Ala Ala Ala Thr Ser Asn Arg Lys Pro Ala Ala Ala Val
        8355                8360                8365

Arg Lys Tyr Thr Thr Ser Ala Ala Thr Gly Gly Leu Lys Ile Thr Ala
        8370                8375                8380

Asn Glu Pro Ala Gln Thr Arg Glu Leu Arg Asn Arg Ile Phe Pro Thr
8385                8390                8395                8400

Leu Tyr Ala Ile Phe Gln Gln Ser Arg Gly Gln Glu Gln Glu Leu Lys
            8405                8410                8415

Ile Lys Asn Arg Ser Leu Arg Ser Leu Thr Arg Ser Cys Leu Tyr His
            8420                8425                8430

Lys Ser Glu Asp Gln Leu Gln Arg Thr Leu Glu Asp Ala Glu Ala Leu
        8435                8440                8445

Phe Asn Lys Tyr Cys Ala Leu Thr Leu Lys Glu Ala Ala Thr Ala Leu
        8450                8455                8460

Ile Gln Lys Arg Arg Glu Leu His His Pro Arg His Glu Arg Asn Ser
8465                8470                8475                8480

His Ala Leu His Val Glu Leu Ser Thr Pro Asn Gly Ile Gly Gly Arg
```

```
                    8485           8490           8495
Arg Leu Pro Gly Leu Leu His Pro His Glu Leu Ala Gln Arg Arg Ala
                8500           8505           8510

Phe Tyr Asp Phe Ser Ser Tyr Thr Arg Leu Pro Lys Pro Asn Thr Phe
                8515           8520           8525

Gly Thr Val Ser Ser Tyr His His Ala Pro Pro Thr Pro Ser Gln Lys
                8530           8535           8540

Leu Ala Arg Arg Pro Ser Val Pro Gly Lys Ser Arg Ser His His Cys
8545           8550           8555           8560

Ile Thr Ser Ser Arg Arg Pro Gly Arg Ser Pro Asn Asp Cys Arg Cys
                8565           8570           8575

Ala Val Ser Trp Arg Leu His Pro Met Ser Ser Gln Ala Ser Ala Tyr
                8580           8585           8590

Lys Thr Pro Asp Asp Gln Arg Pro Arg Tyr Pro Ala Gln Arg Arg Val
                8595           8600           8605

Gly Glu Leu Ser Ala Trp Ser Thr Thr Arg Arg Asn Leu Ser Asp Cys
                8610           8615           8620

Arg Leu Arg Glu Ile Phe Leu His Pro Ser Ser Gly Cys Ser Asp Phe
8625           8630           8635           8640

Gly Lys Phe Val Phe Ala Thr Pro Leu Gly Arg Asn Arg Asp Arg Ser
                8645           8650           8655

Ile Cys Gly Gly Val Tyr Ser Leu Cys Leu Leu Gln Pro Leu Leu Arg
                8660           8665           8670

Ile Ser Trp Ala Leu Pro Gly Arg Val His Thr Glu Leu Arg Arg Asp
                8675           8680           8685

Arg Val Ser Gly Arg Leu Arg Leu Met Ser Gly Asp Ala Ala Glu Leu
                8690           8695           8700

Ser Arg Leu Arg His Leu Asp His Cys Arg Arg Phe Arg Cys Phe Ala
8705           8710           8715           8720

Arg Glu Leu Ile Glu Phe Ile Tyr Phe Glu Leu Pro Lys Asp His Pro
                8725           8730           8735

Gln Gly Pro Ala His Gly Val Arg Ile Ser Ile Glu Gly Lys Ile Asp
                8740           8745           8750

Ser Arg Leu Gln Arg Ile Phe Ser Gln Arg Pro Val Leu Ile Glu Arg
                8755           8760           8765

Asp Gln Gly Asn Thr Thr Val Ser Ile Tyr Cys Ile Cys Asn His Pro
8770           8775           8780

Gly Leu His Glu Ser Leu Cys Cys Leu Met Cys Thr Glu Phe Asn Lys
8785           8790           8795           8800

Asn Ile Lys Thr Leu Leu Arg Thr Ala Ala Ser Ser Thr Arg Ile Leu
                8805           8810           8815

Gln Pro Glu Glu Arg Asn Phe Ser Cys Arg Pro Gly Leu Cys Leu His
                8820           8825           8830

Leu Ser Tyr Ser Gln Thr Arg Ser Ser Thr Thr Pro Leu Phe Gln
                8835           8840           8845

Lys His Phe Pro Tyr Tyr Phe Gln Asn Arg Arg Ala Pro Arg Ser
                8850           8855           8860

Ser Tyr Arg Lys Pro Leu Gly Gly Ser Gly Pro Cys Ser Ala Arg Asn
8865           8870           8875           8880

Ser Cys Gly Trp Ala Cys Asp Tyr Ser Leu Leu Pro Ile His Thr Leu
                8885           8890           8895

Leu His Phe Leu Ser Gly Val Val Val Leu Val Lys Met Gly Pro Ile
                8900           8905           8910
```

```
Leu Val Leu Leu Val Leu Leu Ser Leu Leu Glu Pro Gly Ser Ala Asn
        8915                8920                8925

Tyr Asp Pro Cys Leu Asp Phe Asp Pro Glu Asn Cys Thr Leu Thr Phe
        8930                8935                8940

Ala Pro Asp Thr Ser Arg Ile Cys Gly Val Leu Ile Lys Cys Gly Trp
8945                8950                8955                8960

Glu Cys Arg Ser Val Glu Ile Thr His Asn Asn Lys Thr Trp Asn Asn
        8965                8970                8975

Thr Leu Ser Thr Thr Trp Glu Pro Gly Val Pro Glu Trp Tyr Thr Val
        8980                8985                8990

Ser Val Arg Gly Pro Asp Gly Ser Ile Arg Ile Ser Asn Asn Thr Phe
        8995                9000                9005

Ile Phe Ser Glu Met Cys Asp Leu Ala Met Phe Met Ser Lys Gln Tyr
        9010                9015                9020

Ser Leu Trp Pro Pro Ser Lys Asp Asn Ile Val Thr Phe Ser Ile Ala
9025                9030                9035                9040

Tyr Cys Leu Cys Ala Cys Leu Leu Thr Ala Leu Leu Cys Val Cys Ile
        9045                9050                9055

His Leu Leu Val Thr Thr Arg Ile Lys Asn Ala Asn Asn Lys Glu Lys
        9060                9065                9070

Met Pro Pro Leu Ser Val Tyr Arg His Gly Phe Ser Tyr Ile Ser His
        9075                9080                9085

Ile Cys Gln His Cys His Cys Arg Ser Trp Thr Asn Ser Arg Leu Tyr
        9090                9095                9100

Pro Ser Arg Thr Leu His Ser His Arg Thr Pro Asn His Phe Arg Gly
9105                9110                9115                9120

His Leu Gly Gln Thr Gly Lys Arg Leu Leu Tyr Asn Leu Gln Gln Asn
        9125                9130                9135

Lys Thr Asn Asn Ser Asn Leu Gln His Thr Lys Ser Tyr Ile Asp Cys
        9140                9145                9150

Gln Ser Leu Gln Arg Leu Leu Leu Trp Leu Gln Ile Gln Ser Ile Lys
        9155                9160                9165

Leu Leu Gly Ser Cys Tyr Pro Val Glu Asn His Glu Asn Ala Lys Tyr
        9170                9175                9180

Gly Lys Asp Ser Ile Arg Gln Phe Ser Arg Asn Phe Tyr Ile Ser His
9185                9190                9195                9200

His Thr Arg Arg Lys Lys His Pro Arg Phe Asn Asp Cys Asn Cys Cys
        9205                9210                9215

Ser Gly Gly Ser Gly Asp Gly Thr Asn Asn Asn Met His Ala Phe Ile
        9220                9225                9230

Cys Leu Ser Leu Gln Lys Val Ser Ser Lys Thr Arg Ser Pro Thr Lys
        9235                9240                9245

Ala His Leu Ile Ser Phe Tyr Thr Ala Met Val Ser Thr Thr Thr Phe
        9250                9255                9260

Leu Met Leu Thr Ser Leu Ala Thr Leu Thr Ser Ala Arg Ser His Leu
9265                9270                9275                9280

Thr Val Thr Ile Gly Ser Asn Cys Thr Leu Lys Gly Pro Gln Gly Gly
        9285                9290                9295

His Val Phe Trp Trp Arg Ile Tyr Asp Asn Gly Trp Phe Thr Lys Pro
        9300                9305                9310

Cys Asp Gln Pro Gly Arg Phe Phe Cys Asn Gly Arg Asp Leu Thr Ile
        9315                9320                9325
```

-continued

```
Ile Asn Val Thr Ala Asn Asp Lys Gly Phe Tyr Tyr Gly Thr Asp Tyr
    9330                9335                9340
Lys Ser Ser Leu Asp Tyr Asn Ile Ile Val Leu Pro Ser Thr Thr Pro
9345                9350                9355                9360
Ala Pro Arg Thr Thr Thr Phe Ser Ser Ser Val Ala Asn Asn Thr
                9365                9370                9375
Ile Ser Asn Pro Thr Phe Ala Ala Leu Leu Lys Arg Thr Val Asn Asn
            9380                9385                9390
Ser Thr Thr Ser His Thr Thr Ile Ser Thr Ser Thr Ile Ser Ile Ile
        9395                9400                9405
Ala Ala Val Thr Ile Gly Ile Ser Ile Leu Val Phe Thr Ile Thr Tyr
    9410                9415                9420
Tyr Ala Cys Cys Tyr Arg Lys Asp Lys His Lys Gly Asp Pro Leu Leu
9425                9430                9435                9440
Arg Phe Asp Ile Phe Val Leu Phe Phe Phe Ile Tyr Ser Met Val Asn
                9445                9450                9455
Thr Asn His Gly Thr Lys Phe Leu Leu His His Thr His Leu Cys Ile
            9460                9465                9470
Cys Leu Arg Tyr Phe His Ser Ser Ser His Ser Asn Pro Arg Leu Tyr
        9475                9480                9485
Arg Ser Ile Cys Phe Leu Cys Thr Phe Cys Phe Cys Tyr Leu His Leu
    9490                9495                9500
Arg Met His Ser Leu Pro Gly Tyr Phe Phe Pro Thr Tyr Arg Leu Asp
9505                9510                9515                9520
Pro Cys Ala Asn Cys Leu Pro Ala Pro Pro Ser Arg Ile Pro Gln Pro
                9525                9530                9535
Lys Tyr Arg Gly Thr Ser Thr His Leu Lys Pro Cys Arg Leu Tyr Tyr
            9540                9545                9550
Gln Tyr Phe Cys Phe Tyr Cys Phe Pro Thr Leu Ser Gln Pro Gln Leu
        9555                9560                9565
Pro Ile Val Leu His Gln Asn Thr Leu Glu Asn Ala Asn Ser Asn Asn
    9570                9575                9580
Arg Gly His Phe Leu Leu Ala Ile Glu Lys Asn Gln Lys Phe Pro Gln
9585                9590                9595                9600
Ile Leu Leu Glu Leu Ile Ser Val Ala Pro Phe His Phe Tyr Thr Pro
                9605                9610                9615
Tyr Leu Ile Leu Ala Gly Met Leu Pro Met His Met Ile Ile His Lys
            9620                9625                9630
Thr Gln Arg Asn Thr Phe Pro Tyr Lys Thr Cys Asn Ile Gln Arg Ile
        9635                9640                9645
Thr Lys Val Asn His Asn Pro His Tyr Ser Leu Leu Leu Val Thr Ser
    9650                9655                9660
Thr Pro Ala Glu Met Thr Glu Thr Leu Thr Thr Ser Asn Ser Ala Glu
9665                9670                9675                9680
Asp Leu Leu Asp Met Asp Gly Arg Val Ser Glu Gln Arg Leu Ala Gln
                9685                9690                9695
Leu Arg Ile Arg Gln Gln Glu Arg Ala Ala Lys Glu Leu Arg Asp
            9700                9705                9710
Val Ile Gln Ile His Gln Cys Lys Lys Gly Ile Phe Cys Leu Val Lys
    9715                9720                9725
Gln Ala Lys Ile Ser Tyr Glu Ile Thr Ala Thr Asp His Arg Leu Ser
9730                9735                9740
Tyr Glu Leu Gly Pro Gln Arg Gln Lys Phe Thr Cys Met Val Gly Ile
```

-continued

```
                9745                9750                9755                9760
Asn Pro Ile Val Ile Thr Gln Gln Ser Gly Asp Thr Lys Gly Cys Ile
                    9765                9770                9775
His Cys Ser Cys Asp Ser Ile Glu Cys Thr Tyr Thr Leu Leu Lys Thr
                    9780                9785                9790
Leu Cys Gly Leu Arg Asp Leu Leu Pro Met Asn Lys Met Ile Asn Lys
                    9795                9800                9805
Lys Ser Leu Thr Asn Gln Gln Gly Leu Cys Asn Phe Leu Pro Ala Ala
                    9810                9815                9820
Pro His Phe Pro Leu Pro Asn Ser Gly Ile Leu Asn Pro Val Gln Arg
9825                9830                9835                9840
His Thr Phe Ser Ile Leu Arg Gly Cys Gln Ile Leu Ala Pro Leu Leu
                    9845                9850                9855
Tyr Pro Gln Ser Ser Cys Leu Ser Ser Gln Met Thr Lys Arg Val Arg
                    9860                9865                9870
Leu Ser Asp Ser Phe Asn Pro Val Tyr Pro Tyr Glu Asp Glu Ser Thr
                    9875                9880                9885
Ser Gln His Pro Phe Ile Asn Pro Gly Phe Ile Ser Pro Asn Gly Phe
                    9890                9895                9900
Thr Gln Ser Pro Asn Gly Val Leu Thr Leu Lys Cys Leu Thr Pro Leu
9905                9910                9915                9920
Thr Thr Thr Gly Gly Ser Leu Gln Leu Lys Val Gly Gly Gly Leu Thr
                    9925                9930                9935
Val Asp Asp Thr Asn Gly Phe Leu Lys Glu Asn Ile Ser Ala Thr Thr
                    9940                9945                9950
Pro Leu Val Lys Thr Gly His Ser Ile Gly Leu Pro Leu Gly Ala Gly
                    9955                9960                9965
Leu Gly Thr Asn Glu Asn Lys Leu Cys Ile Lys Leu Gly Gln Gly Leu
                    9970                9975                9980
Thr Phe Asn Ser Asn Asn Ile Cys Ile Asp Asp Asn Ile Asn Thr Leu
9985                9990                9995                10000
Trp Thr Gly Val Asn Pro Thr Glu Ala Asn Cys Gln Ile Met Asn Ser
                    10005               10010               10015
Ser Glu Ser Asn Asp Cys Lys Leu Ile Leu Thr Leu Val Lys Thr Gly
                    10020               10025               10030
Ala Leu Val Thr Ala Phe Val Tyr Val Ile Gly Val Ser Asn Asn Phe
                    10035               10040               10045
Asn Met Leu Thr Thr His Arg Asn Ile Asn Phe Thr Ala Glu Leu Phe
                    10050               10055               10060
Phe  Asp Ser Thr Gly Asn Leu Leu Thr Arg Leu Ser Ser Leu Lys Thr
10065               10070               10075               10080
Pro Leu Asn His Lys Ser Gly Gln Asn Met Ala Thr Gly Ala Ile Thr
                    10085               10090               10095
Asn Ala Lys Gly Phe Met Pro Ser Thr Thr Ala Tyr Pro Phe Asn Asp
                    10100               10105               10110
Asn Ser Arg Glu Lys Glu Asn Tyr Ile Tyr Gly Thr Cys Tyr Tyr Thr
                    10115               10120               10125
Ala Ser Asp Arg Thr Ala Phe Pro Ile Asp Ile Ser Val Met Leu Asn
                    10130               10135               10140
Arg  Arg Ala Ile Asn Asp Glu Thr Ser Tyr Cys Ile Arg Ile Thr Trp
10145               10150               10155               10160
Ser Trp Asn Thr Gly Asp Ala Pro Glu Val Gln Thr Ser Ala Thr Thr
                    10165               10170               10175
```

```
Leu Val Thr Ser Pro Phe Thr Phe Tyr Tyr Ile Arg Glu Asp Asp Gln
        10180               10185               10190

Ile Lys Phe Asn Leu Phe Ile Lys Ser Ile His Lys Ile Arg Val Val
        10195               10200               10205

Ile Leu Pro Pro Pro Ser His Leu Thr Glu Tyr Thr Asn Leu Ser Pro
        10210               10215               10220

Arg  Thr Ala Leu Asn Ile Trp Ile Pro Leu Asp Ile Asp Met Val Leu
10225               10230               10235               10240

Asp Ser Thr Phe Gln Thr Val Ser Glu Arg Ala Asn Leu Gly Ser Val
        10245               10250               10255

Ile Asp Lys Asn Pro Ser Gly Ser Phe Lys Ala Leu Ser Gln Ser Asn
        10260               10265               10270

Cys Cys Gly Trp Thr Pro Glu Ser Gly Ser Arg Ser Ser Gly Arg Arg
        10275               10280               10285

Thr Met Gly Ile Ile Ile Arg Lys Arg Tyr Arg Thr Ile Val Ser His
        10290               10295               10300

Gln  Thr His Lys Gln Pro Leu Ser Ala Ser Leu Arg Ala Thr Ala Val
10305               10310               10315               10320

Tyr Gly Ile Arg Val His Ser Val Leu Lys His Asp Phe Asn Ser Pro
        10325               10330               10335

His Gln Leu Ser Gly Ala Met Arg Ala Ala Thr His Ser Asp Phe Thr
        10340               10345               10350

Gln Ile Phe Ala Val Gly Thr Thr His Tyr Tyr Asn Ile Val Thr Ile
        10355               10360               10365

Ile Lys Ser Ala Pro Ala Lys Thr His Ile Tyr Asn Arg Pro Cys Met
        10370               10375               10380

Thr Ile Ile Pro Lys Phe Asn Ile Asn Met Thr Phe Pro Gln Lys His
10385               10390               10395               10400

Thr Thr His Ile His Asp Leu Phe Trp His Val His Ile Asn Asn Leu
        10405               10410               10415

Ser Val Pro Trp Thr Thr Leu Val Asn His Ala Thr Gln Tyr Asn Leu
        10420               10425               10430

Pro Glu Pro His Cys Gln His Arg Ser Pro Ser His Ala Leu Lys Thr
        10435               10440               10445

Leu Leu Ile Thr Met Thr Met Lys Asn Pro Ile Leu Ser Thr Val Asn
        10450               10455               10460

His  Leu Arg Met Lys Asn Ile Tyr Ser Gly Thr Thr Thr Met His Ala
10465               10470               10475               10480

Ser Ser His Asn Phe Leu Leu Arg Ile Lys His Ile Pro Gly Asn Arg
        10485               10490               10495

Lys Leu Leu Gln Asn Ser Lys Ala Gly Arg Thr Arg Lys Thr Thr Asn
        10500               10505               10510

Thr Thr Tyr Thr Met His Ser His Ser Ile Thr Ile Trp Gln Gln Arg
        10515               10520               10525

Val Val Phe Ser His Arg Ser Ser Gly Phe Ile Phe Leu Thr Thr Trp
        10530               10535               10540

Leu  Gly Ser Gly Val Arg Val Met Ser Gly Ala Cys Arg Ala Cys Ala
10545               10550               10555               10560

Gln Pro Cys His Asn Gly Val Ala Ser His Ser Arg Ile Leu Tyr Ser
        10565               10570               10575

Lys Thr Arg Pro Trp Gln Asn Thr Leu Phe Phe Ala Phe Tyr Pro Ala
        10580               10585               10590
```

```
Ala Arg Val Pro Cys Asp Ser Ser Thr Thr Thr Leu Leu Ser Trp
        10595               10600               10605

Ser Lys Glu Cys Trp Leu Gln Leu Ser Lys Leu His Arg Ile Ser Phe
    10610               10615               10620

Gly Asn His Pro Arg His Met Gln Ile Pro Thr Lys Gln Cys Asn Trp
10625               10630               10635               10640

Ile Val Phe Gln Ala Gly Glu Glu Arg Glu Thr Glu Glu Pro Cys
                10645               10650               10655

Phe Leu Phe Gln Thr Ile Ser Gln Tyr Phe Lys Leu Ile Ala Gln Met
                10660               10665               10670

Ala Ser Leu Ala Pro Thr Val Leu Val Lys Lys His Ser Ile Lys Arg
        10675               10680               10685

Asn Ala Ile Phe Lys Val Leu Asn Gly Gly Phe Gln Gln Ser Leu His
        10690               10695               10700

Ala His Ile Gln Glu Gln Lys Asn Thr Lys Arg Arg Ser Ile Phe Leu
10705               10710               10715               10720

Leu Asn His His Ile Thr Phe Leu His His Ser Gln Ile Ile Phe Ser
                10725               10730               10735

Phe Pro Ala Leu Asn Tyr Ser Cys Gln Phe Leu Trp Ile Gln Ser Thr
        10740               10745               10750

His Tyr Lys Gln Val Pro Glu Gly Ala Leu His His His Ser Thr His
        10755               10760               10765

Pro His Asn Asp Lys Ile Ser Cys Ser Cys Val Thr Cys Ser Glu Leu
        10770               10775               10780

Arg Met Ala Thr Ser Ile Asp Met Pro Leu Ala Leu Ser Ser Ser Leu
10785               10790               10795               10800

Ser Ser Ser Cys Lys Asn Ser Leu Ile Leu Ser Pro Asn Cys Leu Ala
                10805               10810               10815

Arg Ser Pro Pro Gly Thr Arg Ala Gly Asp Ala Thr Val Gln Tyr Lys
        10820               10825               10830

Arg Arg Pro Pro Gln Leu Ala Pro Ala Lys Thr Arg Leu Glu Ala Tyr
        10835               10840               10845

Trp Glu Pro Pro Val Ile Ser Ser Lys Leu Leu Glu Ile Ser Gly Arg
        10850               10855               10860

Val Ser Cys Lys Asn Ile Lys Glu Lys Phe Ala Lys Lys Thr Phe Lys
10865               10870               10875               10880

Thr Ser Gly Met Gln Met Gln Val Thr Ala Leu Arg Ser Asn Ile Val
                10885               10890               10895

Ser Phe Glu Leu Val Cys Lys Asn Lys Lys Lys Asn Lys Arg His Ile
        10900               10905               10910

Ile Val Ala Arg Thr Asp Gly Ile Ser Leu Ser Ile Thr Arg Gln Ala
        10915               10920               10925

Thr Gly Ser Pro Ala Arg Pro Ser Asn Leu Ser Ser Leu Asn Asn Ser
        10930               10935               10940

Thr Glu Ser Ser Ser Arg Pro Ala Ile Ile Leu Asp Glu Ala Tyr Asn
10945               10950               10955               10960

Pro Asp Met Leu Ala Ser Val Asn Glu Lys Lys Gln Pro Thr Pro Leu
                10965               10970               10975

Gly Ile Ile Met Leu Asn Arg Lys Tyr Ser Lys Ala Thr Pro Arg Gly
                10980               10985               10990

Tyr Lys Val Lys Gly Thr Gly Glu Lys Ile Leu Phe Leu Cys Cys Cys
        10995               11000               11005

Ser Gly Asn Val Ala Pro Gly Pro Ser Lys Tyr Thr Tyr Lys Ala Ser
```

-continued

```
            11010              11015              11020
Ser Ala Met Ala Tyr Gln Thr Lys Tyr Ser Gly His Thr Lys His Lys
1102 5              11030              11035              11040

Leu Ser Asp Ser Pro Thr Ser Pro Gln Tyr Ile Tyr Thr Gln Ala Leu
              11045              11050              11055

Asn Arg Asn Gly Ser Lys Val Lys Ile Pro Pro Asn Pro Thr His Thr
            11060              11065              11070

Pro Lys Leu Arg His Gln Gly Lys Val Gln Phe His Phe Arg Asn Pro
            11075              11080              11085

Asn Arg Arg Asn Phe Leu Phe Leu Thr Val Arg Asp Ile Pro Leu Thr
            11090              11095              11100

Cys Asn Val Ile Phe Pro Arg Ser His Arg Pro Phe Pro Leu Thr Pro
11105              11110              11115              11120

Gln Pro Ile Thr Thr  Arg Ser Thr Leu Phe  Lys Ile Thr Ser Phe  Thr
                11125              11130              11135

Tyr Trp His His Ser Ile Tyr Lys Val Tyr Tyr Cys Gly Ile Asn Thr
              11140              11145              11150

Leu Ala Ile Ser His Leu Arg Lys Asn Arg Arg Leu His Gly Thr Arg
              11155              11160              11165

Lys Phe Arg Lys Thr Arg Ser Lys Pro Pro Arg Asn Gly Ser Lys Ser
        11170              11175              11180

Thr Trp Pro Thr Asn Thr Pro Pro Cys His Lys Tyr His Ile Ile Gln
11185              11190              11195              11200

Lys Asn Thr Ser Ser Phe Ser Phe Arg Ala Lys Ile Asn Asn Phe His
              11205              11210              11215

Leu His Pro Val Lys Thr Thr Ser Phe Pro Val Lys Tyr Arg Gly Lys
              11220              11225              11230

Thr Lys Phe Arg Glu Lys Lys Ala Phe Leu Cys Val Thr Phe Pro Ala
              11235              11240              11245

Thr Thr Cys Lys Lys Thr Pro Pro Pro Gln Asn Val Ile Phe Pro Arg
              11250              11255              11260

Ser  His Arg Pro Phe Pro Leu Thr Pro Gln Pro Ile Thr Thr Arg Ser
11265              11270              11275              11280

Thr Leu Phe Lys Ile Thr Ser Phe Thr Tyr Trp His His Ser Ile Tyr
              11285              11290              11295

Lys Val Tyr Tyr
              11300
```

VIRAL VECTORS FOR GENE THERAPY

The present invention concerns the field of gene therapy and in particular the use of specific adenoviral vector systems for gene therapy, said vector systems offering enhanced efficiency and specificity for gene delivery. The present invention also provides novel sequence information regarding a specific viral vector with high binding efficiency and infectivity to cells of neural origin, endothelial cells, carcinoma cells and dendritic cells.

BACKGROUND OF THE INVENTION

Gene transfer into neural cells has grown into a big field in neuroscience. The usage of gene transfer is ranging from treatment of genetic diseases, tumours and acquired degenerative encephalopaties such as Alzheimer's disease and Parkinson's disease to being a powerful tool in the study of biological mechanisms. An important application of gene transfer is gene therapy, which is when a therapeutic gene is inserted into the cells by ex vivo or in vivo techniques. One of the obstacles to overcome with gene therapy is to get the gene into the right cell type. The choice of cell depends on the nature of the disease. One example is cystic fibrosis, where clinical trials have already started to deliver a vector with a correct copy of the damaged gene (the CFTR gene) as an aerosol into the lungs. But even if the disease is manifest in the lung it is not certain that the correcting gene will enter the right cell type. In other diseases such as Haemophilia B where a blood clotting factor (IX) is missing in plasma, it is not as important to reach the damaged cell type. Even if the liver normally makes the clotting factor, it does not matter if the therapeutic gene is inserted in muscle cells, fibroblasts or even blood cells as long as the clotting protein is produced in therapeutic amounts and with the correct post-translational modifications. The protein accessibility to its target and the immunological status is also important. A protein that is normally expressed only inside the blood-brain barrier could for example be immunogenic if exposed on the outside.

There are two different approaches to deliver the DNA (target genes) into the cells. The first is the usage of non-viral vectors to insert the DNA. The non-viral approach consists of methods like direct injection of the DNA, mixing the DNA with polylysine or cationic lipids that allow the DNA to be internalised. Most of these approaches have a low efficiency of delivery and transient expression of the gene. The second and more widely used approach to insert the DNA is by using viral vectors. Viruses have evolved a mechanism to insert their DNA into cells very effectively, but the side effect is that humans have evolved an effective immune response to eliminate viruses from the body.

To function as a viral vector in the nervous system, the vector should have certain properties. Since almost all cells in the brain are non-dividing, the vector must be able to infect non-dividing cells. A good vector also needs to be non-toxic to the cells in the dose required for infection (direct cytotoxicity i.e. by capsid proteins and antigenicity). It should be replication deficient to prevent the virus from uncontrolled spreading and damage to the cells. After the DNA has entered the nucleus it should integrate in a site-specific location in the host chromosome or become a stable extra-chromosomal element (episome). The desired gene should be expressed without interfering with the cellular expression machinery.

Viral vectors used for gene delivery into the nervous system are herpes simplex-1 virus, adenovirus, adeno-associated virus and retrovirus such as lentivirus. All the viruses pathogenicity genes have been deleted and their ability to replicate has been incapacitated.

Adenoviruses are good candidates for gene therapy towards the nervous system for a number of reasons. They can infect both dividing and non-dividing cells, the viral genome is relatively stable and is easy to manipulate by recombinant DNA techniques. Replication of the virus is efficient in permissive cells and the pathogenicity is low. One of the obstacles to overcome with all viral vectors is to achieve a sustained expression. The viral vector evokes an immune response that is both cell mediated and humoral and the infected cells may become destroyed by the inflammatory response within a couple of weeks. The immune response evoked by adenoviral gene transfer is however different in the brain compared to in the peripheral tissues. The immune response in the brain is not sufficiently strong to eradicate the adenovirus infected cells. However, if the individual has had a previous exposure to the adenovirus or was inoculated with the virus later, a strong inflammatory response can be evoked also in the brain. Consequently, adenovirus serotypes of low prevalence in the society should preferentially be used as vectors to be more successful as gene delivery vectors.

The adenoviruses are a family of DNA viruses that can infect both dividing and non-dividing cells. They do not usually integrate into the host chromosome, instead they are replicated as extra-chromosomal elements inside the nucleus of the host cell. Adenoviruses can bind to a range of different cell types. The clinical picture of an adenovirus infection is often respiratory infection or gastro-enteritis. A tonsillitis similar to a streptococcus A infection is also not uncommon. Some of the adenovirus serotypes can cause epidemic keratoconjunctivitis or in some cases even meningitis or encephalitis.

There are at the present 51 known serotypes of adenovirus, which have been divided into six different subgenera, A-F, depending on their biological properties and genetic homology. Virus within the same subgenus shares more than 50% DNA homology whereas viruses in different subgenera have less than 20% homology (Wadell G., Adenoviruses (adenoviridae): General features. Encyclopaedia of Virology. Ed. Webster R. G., Granoff A., Academic Press Ltd London, pp 1-7, 1999).

Human adenoviruses are non-enveloped and about 80 nm in diameter with a 36 Kbp double stranded DNA. The virion capsid is composed of 240 hexon capsomers and 12 vertex capsomers. An antenna-like fibre projects from each vertex capsomer (located at the corners of the icosahedral capsid). The epitopes capable of making serotype specific antibodies and hence also the epitopes determining the serotype are located on the external portions of the hexons and on the most distal knob of the fibre.

Infection starts with the attachment of the fibre knob to a cellular receptor on the permissive cell. The cellular receptor for the virus fibre is coxsackievirus-adenovirus receptor (CAR) for all subgenera except subgenus B. Additional cellular receptors for adenoviruses are the major histocompatibility complex class I (MHC-I) alpha2 and sialic acid. The viral penton base then binds to the cellular integrin $\alpha_v\beta_3$ and the virus is internalised by endocytosis into an endosome. Upon fusion with a lysosome, the pH is lowered leading to alterations in the viral capsid, releasing the virion from the endo-lysosome. The virion is then transported to the nucleus where the replication and transcription takes place. The spliced mRNA is translated in the cytoplasm. Production of the fibre protein can be detected 9-11 h after infection. The structural proteins are then translocated into the nucleus where assembly of new virions takes place.

PRIOR ART

EP 1 054 064 discloses adenovirus derived gene delivery vehicles comprising at least one element of adenovirus type 35. The nucleic acid sequence of adenovirus 35 is enclosed in said patent application, published on Nov. 22, 2000. The sequence is also available through the EBI/EMBL database under access number AAC8884. The homology between this sequence, and the sequence disclosed in the present application is quite high. Naturally, the viruses within each of the six subgenera exhibit more than 50% sequence homology, as genetic homology is one of the foundations of the subtyping system. Within some subtypes, further divisions can be made, e.g. based on the receptor/receptor, combinations of each virus. In the subgenus B, a division into two groups can be made. Group B:1 contains e.g. the adenoviruses 3 and 7, which are known to cause acute airway infections. Group B:2 contains e.g. the viruses 11 and 35 which have tentatively been shown to possess a trypsin resistant receptor or receptor combination, which also seems to be resistant to EDTA. Despite this similarity, the viruses Ad 11 and 35 exhibit different binding patterns, as evidenced by the figures attached to the present application. There are also strong indications that Ad 11 in fact possesses a specific and hitherto unknown receptor structure (unpublished results). Further, the present sequence differs from that of EP 1 054 064 in those parts of the genome which are associated to the characterising features of the virus, such as features related to tropism and immune response. These differences, the heterology between the sequences, are of such magnitude, that they entail functional and qualitative differences between adenovirus 11 and 35. It should be kept in mind, that a difference of even one amino acid in the ligand structure can be of great significance for the binding properties of a virus. Similarly, minor differences in epitope structure influence the interaction with antibodies in the host organism.

It has previously been shown that adenovirus 11p exhibits high affinity to hematopoietic cells (Anna Segerman et al., Adenovirus types 11 p and 35 p show high binding efficiencies for committed hematopoietic cell lines and are infective to these cell lines, *J Virology*, February 2000, Vol. 74, No. 3, 1457-1467). This article however gives insufficient information on the interaction between the virus and normal cells or stem cells. Importantly, the experimental set-up results in the information being specific for cancerous cells, and the relevance on non-cancerous or pre-cancerous cells can be disputed. Further, important groups of cells subject of the present invention, were not studied in the work by Segerman et al.

In view of the above, it remains a problem to make available an adenoviral vector with both high infectivity to important cell types, and a low prevalence in society. It is very important to gain more knowledge of specific features responsible for the binding and immune response interaction of the viruses. Further problems and their solutions will be evident from the description and examples, as read by a person skilled in the art.

SUMMARY OF THE INVENTION

The present invention provides a purified and isolated DNA of an adenovirus consisting of a sequence encoding adenoviral proteins having the amino acid sequence of SEQ. ID. NO. 2 or homologues thereof. The invention further provides the purified and isolated DNA of an adenovirus having the nucleotide sequence of SEQ. ID. NO. 1, or a sequence hybridising thereto under stringent conditions. The invention also provides adenoviral vectors comprising these sequences or fragments thereof, in particular the nucleic acid or amino acid sequence fragments corresponding to the hexon and the fiber protein of the virus, including the use of these in methods for gene therapy.

BRIEF DESCRIPTION OF THE DRAWINGS

The present invention will be described in further detail below, in the description and attached sequence listing and drawings, in which.

DESCRIPTION

Figure 1:
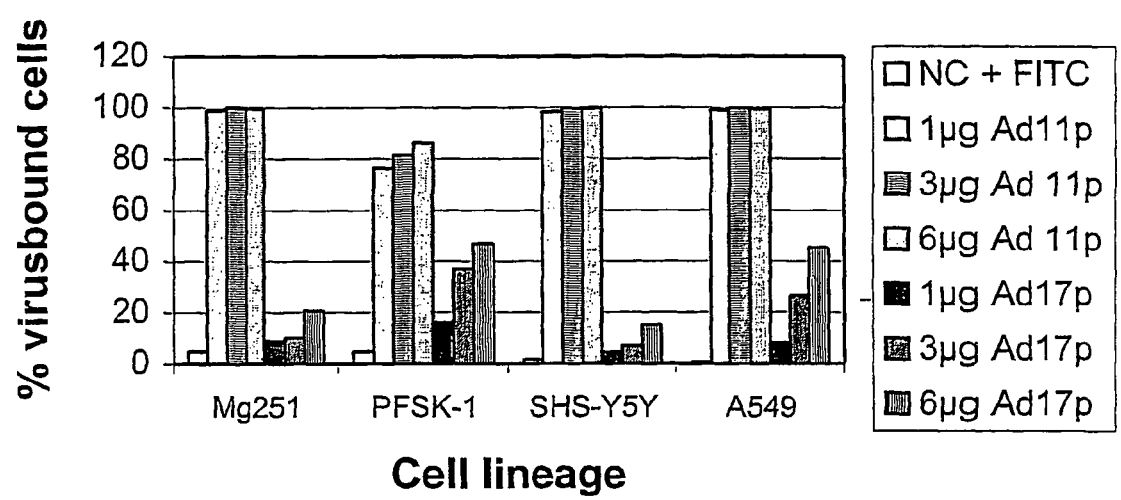
FIG. 1 shows the mean values of the FACS results in % virusbound cells for the neural cell lines Mg251, PFSK-1, SHS-Y5Y and the epithelial cell line A549.

The term "substantially homologous" as used herein refers to the ability of two nucleic acids to hybridise under at least moderately stringent hybridisation conditions. Stringency of hybridisation is a term of the art that refers to the conditions used for a hybridisation reaction whereby complementary single strands of nucleic acid join to one another to form double-stranded nucleic acid with some degree of mismatch, the degree of which is a function of the stringency-used. In particular, the stringency will depend upon the size and composition of the strands of nucleic acid that are caused to react, the degree of mismatching allowed, the desired cross reactivity, and the like. The degree of stringency can be affected by ionic conditions employed and temperature, among others, as is well known in the art (e.g. Sambrook et al., Molecular cloning: A laboratory manual, second edition, 1989).

The terms "functionally homologous" and "functionally similar" refers to homologies and similarities accounting for the same function or behaviour with respect to tropism, affinity to specific cells and immune response inducing behaviour.

The present inventive adenoviral vector preferably further comprises foreign nucleic acid, which will typically encode, and express within a host cell, a product that has therapeutic and/or prophylactic utility. The term "foreign nucleic acid" is used herein to refer to any sequence of DNA or RNA, in particular DNA, functionally inserted into a vector according to the present invention that is foreign to the adenoviral genome. Such foreign nucleic acid may constitute a gene, a portion of a gene, or any other nucleic acid sequence, including but not limited to a sequence that encodes RNA, antisense RNA, a synthetic oligonucleotide, and/or a polypeptide. Foreign nucleic acids having therapeutic utility include genes that encode a missing or impaired gene function, and genes influencing the behaviour of the cell, such as so called suicidal genes. Foreign nucleic acids having prophylactic utility include genes that encode a gene product that has an ability to prevent disease directly or indirectly, e.g. by providing a source of a polypeptide or other antigen to elicit an immune response thereto.

The term "therapeutic and/or prophylactic agent" and the term "product having therapeutic and/or prophylactic utility" are used as equivalents and are meant to comprise inter alia antigens and immunostimulating agents, such as cytokines etc.

The present invention provides the purified and isolated DNA of an adenovirus consisting of a sequence encoding adenoviral proteins having the amino acid sequence of SEQ. ID. NO. 2 or homologues thereof. As homologues are meant functional homologues or sequences exhibiting so high homology that also the characteristic features of the expressed virus proteins are the same, or a homology of at least 98%, preferably at least 99% to the sequence of SEQ. ID. NO. 2.

The present invention further provides the purified and isolated DNA of an adenovirus having the nucleotide sequence of SEQ. ID. NO. 1 or a sequence hybridising thereto under stringent conditions or substantially homologous therewith.

The present invention provides a novel adenoviral vector comprising a sequence with at least 98 % homology to the sequence of SEQ. ID. NO. 1, in particular an adenoviral vector comprising a sequence with at least 99% homology to the sequence of SEQ. ID. NO. 1 or most preferably an adenoviral vector comprising a sequence substantially homologous to the sequence of SEQ. ID. NO. 1.

The present invention also provides a purified and isolated DNA sequence comprising the nucleotide sequences defined by positions 30811-31788 and 18254-21100 in SEQ ID NO:1.

In particular, the present invention provides a novel adenoviral vector comprising the sequence of SEQ. ID. NO. 1 or a fragment thereof.

Further, the invention provides a vector as above, wherein said vector further comprises a foreign nucleic acid that can express in a human a therapeutic and/or prophylactic agent or a foreign nucleic acid which in itself has a therapeutic and/or prophylactic utility.

The present invention further provides a method of gene therapy comprising the administration to a human, preferably a human patient, in need of gene therapy a therapeutically effective amount of a vector as defined above.

The present invention further provides the use of a vector comprising a sequence of SEQ. ID. NO. 1 or a sequence substantially homologous therewith in gene therapy.

The present invention further provides the use of a vector comprising a sequence of SEQ. ID. NO. 1 or a sequence substantially homologous therewith in cancer therapy. The invention also encompasses the use of a vector comprising a sequence of SEQ. ID. NO. 1 or a sequence substantially homologous therewith in vascular therapy.

The use of a vector comprising a sequence of SEQ. ID. NO. 1 and a selected therapeutic gene operatively linked to regulatory sequences which direct expression of said gene in the production of a medicament for treating a patient having an acquired or inherited genetic defect.

The invention makes available the use of a vector as defined above for the transfection of human cells chosen among cells of neural origin, and in particular for the infection of human cells chosen among glioblastoma, neuroblastoma and medulloblastoma.

The invention makes available the use of a vector as defined above for the transfection of human cells chosen among hepatoma cells, breast cancer cells, prostatic cancer cells and endothelial cells.

The invention makes available the use of a vector as defined above for the transfection of human cells chosen among dendritic cells.

The invention makes available a vector with pronounced affinity for CD34 positive hematopoietic progenitor cells, and consequently a method for the transfection of such cells. One application of considerable clinical potential is therefor to use adenovirus 4 in an ex vivo process for purging bone marrow derived hematopoietic progenitor cells from metastatic epithelial tumor cells, e.g. breast cancer or prostatic cancer cells. In the course of chemotherapy, it is common that bone marrow is collected from the patient before the therapy is commenced, and returned to the patient after completed therapy. This however entails the risk that small amounts of tumor cells have remained in the bone marrow, and are returned to the patient. Studies performed by the present inventors have shown that adenovirus 4 has affinity for these cells but spares hematopoietic progenitor cells, thus making it a promising instrument for this treatment.

Cells of Neural Origin

The present inventors have evaluated the ability for adenoviruses of the subgenera B, C, D and E to bind, infect and replicate in cells of neural origin. Especially Ad17 was interesting to compare since there are reports indicating efficient infection of primary rat neural cells by Ad2 when its fibre was replaced by the Ad17 fibre (Chillon M, Bosch A, Zabner J, Law L, Armentano D, Welsh M. J., Davidson B. L.; Group D Adenoviruses infect primary central nervous system cells more efficiently than those from group C.; *Journal of Virology* 73(3): 2537-2540, 1999). Notably, adenoviruses are species specific and it is therefor important to test this hypothesis in human tissues. Three different human neural cell lines were assessed, cells from a glioblastoma, neuroblastoma and a medulloblastoma cell line.

To address whether a virus can be used as a vector for gene delivery to a certain cell type one must first know the binding efficiency of the virus to the particulate cell type. The immunostaining procedure showed that all of the virus types could be expressed in the three tested cell lines, but the amounts of Zircons produced were clearly different. The time span from infection to production of viral particles also differed between the serotypes.

Expression of viral proteins in the SDS-PAGE experiment indicates that the virion can attach to the cell and become internalised. It also indicates that the virus is efficiently transported to the nucleus of the specific cell type and express its DNA. This is a necessary property for a virus to function as a vector candidate. It is not certain that all of the bands not present in the negative control represent viral proteins. The virus infection can induce the expression or suppression of proteins. To further investigate this issue one can perform a western blot against the viral proteins. If the cellular protein bands are absent it indicates that the virus infection turns off the synthesis, however, if cellular bands do appear it is not certain that the virus leaves the cellular protein machinery intact. If not all of the cells are infected, the non-infected cells can produce a "background" with cellular protein bands that are not expressed in the infected cells.

The FACS experiment can give an idea of how large percentage of the cells are binding to the serotypes Ad11p and Ad17. Surprisingly, Ad11p attaches to nearly 100% of the cells with the virus/cell ratio used (according to the FACS result). This indicates that adenovirus type 11p does not turn off the cellular protein synthesis because the cellular protein bands are still present in the infected cells and there are not enough non-infected cells in that population to produce a "background".

It is also important to keep in mind that the radioactive labelling was initiated 22 h after the virus infection. The proteins produced before or much after that will not be labelled in the SDS-PAGE. The fact that viral Ad17 proteins were not detected in the neural cell lines does not necessarily mean that no viral particles were produced. The immunostaining indicates that Ad17 is expressed in all cell lines, but that expression in the neural cell lines is inefficient and delayed. Ad17 needs between 48 h and 5 days to get properly expressed except in the A549 cells. The FACS analysis indicates that Ad17 is binding to the neural cells, but not to the same degree as Ad11p. It should be kept in mind though, that binding is necessary for infection and viral expression, but the reverse is not always true. Binding does not necessarily lead to successful infection and expression.

Ad4p seems to have a very fast and effective expression in both PFSK-1 and Mg251 cells according to the immunostaining experiments performed by the present inventors. Importantly, Ad4p was also the only serotype showing expression in all the three neural cell lines.

The adenoviruses commonly used for gene transfer is Ad5v and Ad2 (both belonging to subgroup C) and they are used as representatives for most adenovirus-mediated gene transfers, no matter what tissue is addressed. This strategy is deleterious since gene transfer to neural cells by Ad5v is not optimal. Ad4p is infecting neural cells better than Ad5v. The high number of different adenoviruses and the fact that different adenoviruses have different tropisms (Wadell G., Adenoviruses (adenoviridae): General features. Encyclopaedia of Virology. Ed. Webster R. G., Granoff A., Academic Press Ltd London, pp 1-7, 1999) gives an indication that there is probably an optimal adenovirus type for each tissue. The task is just to find the appropriate vector for the specific purpose. Another important issue when choosing the best suited vector is the prevalence of immunity in the society. Ad5 is so common in most societies that more than 60% of the adult population are immune, whereas 10% or less have been infected by Ad11 or Ad17.

As mentioned in the introduction the adenovirus mediated expression cannot be sustained in a tissue if the individual has had an earlier contact with the virus and therefore can induce an anamnestic immune response against it. If a virus with high specificity for the target cells and high efficiency of internalisation and expression is chosen, low amounts of the viral vector can be used. This approach will reduce the risk of direct toxicity or immune response mediated adverse reactions, consequently it is important to improve the vectors used today and continue the search for good gene transfer vectors.

Endothelial and Carcinoma Cell Lines

The present inventors have also shown that Adenovirus type 11p shows markedly higher binding affinity than the conventionally used Ad5 to the endothelial cell line and the studied carcinoma cell lines. Ad 11p also exhibits higher infectivity in hepatoma, breast cancer and endothelial cell lines, compared to Ad 5.

Endothelial cells are essential target cells for gene therapy because they are intimately involved in disease processes associated with inflammation and angiogenesis and they are readily accessible to gene therapy vectors via the circulation. The above surprising finding, that endothelial cells are least permissive to the conventionally used vector Ad 5v, but more permissive to Ad 4p and Ad 11p supports the feasibility of the use of these vectors for gene therapy, as provided by the present invention.

According to one embodiment of the invention, Ad 11p is used for gene transfer in ex vivo and in vivo cancer gene therapy and for gene therapy of vascular diseases.

The adenovirus vector according to the present invention, which exhibits a high tropism towards endothelial cells, makes available methods for preventing the formation of neo-intima and microangiogenesis. The inventive vector is therefor used in vascular surgery, e.g. for preventing the formation of neo-intima in vascular prosthesis, such as vascular stents. The invention further provides the use of the vector in the prevention of scar formation in surgical applications, where one consequence of the surgical operation may be excessive scar formation. The invention also provides a method for the treatment of cancer, in that the formation of blood vessels in growing tumours can be prevented.

Disseminated metastatic tumours contain frequently the only dividing cells in the local environment. They can be addressed using a vector directed at microangiogenesis sites and with a capacity to bind, internalise and be expressed in the tumour cells. Specificity of the expression of the target genes can be obtained via the native tropism of the adenovirus vectors and/or organ-specific promoters. The inventive vector as defined in the description and claims is applicable also for this purpose.

The present invention also provides the use of Ad 4p for gene therapy of hepatoma, liver diseases in vivo, and prostatic cancer.

Dendritic Cells

The present inventors have also shown that Ad 11p exhibits high binding affinity to dendritic cells, and that the binding affinity is higher than that for the conventionally used viral vector Ad 5v. In a comparative analysis, Ad 11p but not Ad 5v manifested intranuclear expression in dendritic cells, as demonstrated by confocal microscopy, further underlining the utility of this vector as a vector for gene therapy.

An adenoviral vector according to the present invention bearing a gene encoding a product that has therapeutic and/or prophylactic utility may be administered to a human or other human patient, preferably suspended in a biologically compatible solution or a pharmaceutically acceptable delivery vehicle. A suitable vehicle is sterile saline solution. Other aqueous and non-aqueous isotonic sterile injection solutions and aqueous and non-aqueous sterile suspensions known to be pharmaceutically acceptable carriers and well known to those of skill in the art may be employed for this purpose.

A composition for administration of an adenoviral vector according to the invention may be formulated to contain other components, such as adjuvants, stabilisers, pH adjusters, preservatives and the like. Such components are well known to persons skilled in the relevant art of viral gene therapy.

The adenovirus vectors according to the invention are administered in a pharmaceutically effective amount, i.e. an amount that is effective to transfect the desired cells—in the chosen route of administration—and provide sufficient level of expression of the selected gene to provide a therapeutic benefit.

Conventional and pharmaceutically acceptable routes of administration include, but are not limited to, intranasal, intramuscular, intratracheal, subcutaneous, intradermal, rectal, oral, instillation into the urinary bladder and other parenteral routes of administration. Routes of administration may be combined, if desired, or adjusted depending upon the therapeutic goal, e.g. elicitation of immunity, and primarily on the nature of the disease being treated.

EXAMPLES

1. Cells of Neural Origin

1.1 Cell Lines and Virus Strains Used

A 549 (human oat cell carcinoma of the lung), Mg251 (human glioblastoma) and SHS-Y5Y (human neuroblastoma) was grown in Dulbecco's modified Eagle's medium (DMEM) (Sigma) containing 0.75% sodium bicarbonate (w/v), 10% foetal bovine serum (FBS) (Gibco BRL), 20 mM Hepes (pH 7.4) and 1×PEST (penicillin and streptomycin). PFSK-1 (humnan medulloblastoma) was grown in RPMI 1640 containing 10% FBS, 20 mM Hepes (pH 7.4) and 1×PEST. The viruses used in the study was Ad4p (prototype, strain RI-67), Ad5v (vector, strain pFG140), Ad11p (prototype, strain Slobitski) and Ad17 (prototype, strain Ch22).

1.2. Virus Purification

Ad4p, Ad5v, Ad11p and Ad17 were grown in A549 cells. 5 days after infection with the viruses the infected cells were harvested and pelleted for 5 min at 3000 rpm. The pellet was resuspended in 12 ml 20 mM Tris, pH 7.5. The solution was kept on ice and sonicated for 3×10 seconds at 70% power (Sonicator MSE). An equal volume of Arclon was added to the suspension and was then shaken for 20 minutes and centrifuged at 3000 rpm for 5 min. The supernatant was layered on a discontinuous caesium chloride (CsCl) gradient followed by centrifugation at 25 000 rpm (Beckman L5-65B Ultracentrifuge) for 2.5 h at 4° C. The CsCl gradient consisted of three phases, 1.37 g/ml, 1.32 g/ml and 1.27 g/ml. Adenoviruses have a density of 1.34 g/ml in CsCl. The virion band was removed using a syringe. After centrifugation, the virions were purified from the CsCl by desalting on a NAP-10 column (Pharmacia, Sweden) and eluted with 1.5 ml 10 mM PBS. The virions were aliquoted and frozen in −80° C. in 10% glycerol. The virion concentration was determined by spectrophotometer. One optical density unit at the absorbance$_{260\ nm}$ minus absorbance$_{330\ nm}$ corresponds to 280 µg virions or $10^{12}$ virus particles/ml.

1.3. Virus Labelling

To label the virions with biotin they were purified as described above with a CsCl gradient The virions in CsCl were put on a NAP-10 column, and eluted with 1.5 ml labelling buffer (50 mM NaHCO$_3$, 135 mM NaCl, pH 8.8). Three µl MgCl$_2$ (1M) was added to a concentration of 2 mM. 165 µl N-hydroxysuccimmidobiotin (1 mg/ml) dissolved in dimethylsulfoxide (DMSO) was added and the virions were mixed with the biotin in the dark over night at 4° C. The free biotin was removed on a NAP-10 column eluted with 10 mM PBS. Glycerol was added and the viruses were aliquoted and frozen until used.

1.4 FACS Experiment

The cells were washed with 0.05% EDTA in PBS and then trypsin digested. The trrpsin was inactivated by addition of growth media (10% FBS+DMEM/RPEM). The cells were pelleted (1000 rpm 5 min, Beckman model TJ-6) and then washed with 5 ml DMEM/RPMI containing 2% inactivated FBS and 0.01% NaN$_3$. After a centrifugation the cells were resuspended in 5 ml DMEM/RPMI containing 2% inactivated FBS and 0.01% NaN$_3$. The cells were counted and allowed to regenerate its surface receptors for 1h at 37° C., and was then pelleted and resuspended in PBS containing 2% inactive FBS and 0.01% NaN$_3$ (PBS—FBS—NaN$_3$) to a concentration of 1 million cells/100 µl. 1 million cells were then added to each well in a microtitre plate. The cells were then pelleted on the microtitre plate and the supernatant was discarded. Biotinylated virus diluted in PBS—FBS—NaN$_3$ was added to the cells in the amounts of 1, 3 and 6 pg virions/cell. This corresponds to 3600, 10700, respectively 21400 virions/cell. The cells were kept on ice to avoid internalisation of the virus particles and incubated for 30 min in 4° C. to allow virus attachment. The cells were washed twice with 150 µl PBS—FBS—NaN$_3$. 100 µl Streptavidin-fluorescein isothiocyanate (FITC; DAKO) diluted 1:100 was added and incubated for 30 min at 4° C. The cells were washed again and resuspended in 300 µl PBS—FBS—NaN$_3$ containing propidium iodide (7 ng/ml) to exclude dead cells from the analysis. The measurement included 10 000 cells/sample and the data were analysed with the LYSYS II software program (Becton Dickinson).

1.5. [$^{35}$S]Methionine-Cysteine Labelling of Proteins After Virus Infection The cell lines Mg251, A549, PFSK-1 and SHS-Y5Y were grown to an appropriate cell density in 25 cm$^2$ bottles, corresponding to approximately 1.5 million cells. The growth medium was replaced with a minimal amount of medium (2 ml) mixed with the virions, each bottle was infected with 3 µg virions, i.e. 10700 virions per cell. The infected cells were incubated for 90 min at 37° C. on a rocking platform. The medium used during the infection was DMEM for Mg251, A549 and SHS-Y5Y and RPMI 1640 for PFSK-1, containing 5% FBS, 20 mM Hepes pH 8.0 and 1×PEST.

Unbound virus particles were removed by washing. The cells were then incubated for 20 h in DMEM/RPMI 1640 containing 5% FBS, 20 mM Hepes pH 7.4 and 1×PEST at 37° C. The cells were washed with methionine and cysteine free DMEM/RPMI 1640 containing 5% FBS, 20 mM Hepes pH 7.4 and 1×PEST and then incubated for 2 h with 2.5 ml of the same type of medium to deplete endogenous methionine and cysteine. At 22 h post infection (p.i.) 0.35 mCi Tran$^{35}$S-label (1175 Ci/mmol, 10.5mCi/ml; ICN Biomedicals) was added to each bottle. After labelling for 1 h at 37° C., 26 µl (200 mM) unlabelled cysteine was added and after 4.5 h 26 µl unlabelled methionine (100 mM) was added. After labelling for 24 h another 26 µl of both unlabelled cysteine and methionine were added (making the final concentration 2 and 4 mM, respectively).

The infected cells were harvested at 72 h p.i. using a cell scraper. The cells were pelleted in falcon tubes and washed twice with 2 ml 0.1M Tris-HCl pH 8.0 containing 5 mM EDTA and 1 mM phenylmethylsulfonyl fluoride (PMSF). The cells were then dissolved in 90 µl of the same buffer, 10 µl of each sample were taken to protein separation on a 12% sodium dodecyl sulphate-polyacrylamide gel (SDS-PAGE). The gel was stained with Coomassie blue, dried and autoradiographed for 22 h. To distinguish the viral proteins from the cellular proteins, Tran$^{35}$S-labelled non-infected cells were used for each cell line as a control.

1.6. Immunostaining Procedures

The neural cell lines Mg251, PFSK-1 and SHS-Y5Y were grown in 24-well plates (2 cm$^2$/well) using DMEM (for Mg251 and SHS-Y5Y) and RPMI 1640 (for PFSK-1) containing 10% FBS, 20 mM Hepes pH 7.4 and 1×PEST. The cells were infected with Ad4p, Ad5v, Ad11p and Ad17 (2 pg/cell) during 1 h at 37° C. in 300 µl DMEM/RPMI 1640 with 20 mM Hepes pH 7.4 and 1×PEST (no FBS). After 1 h 1.2 ml DMEM/RPMI 1640 containing 2% FBS, 20 mM Hepes pH 7.4 and 1×PEST was added to each well. The cells were detached from the surface by washing with PBS containing 0.05% EDTA after 24 h, 48 h and 120 h p.i. The cells were then washed in PBS and the cells from each well were resuspended in 300 µl PBS each and allowed to dry on a glass slide. The cells were fixed in 100% ice-cold methanol for 10 min and then washed in PBS. Non specific binding was reduced by a blocking step using PBS containing 0,1% BSA and 1% rabbit serum for 20 min.

As a primary antibody sera from rabbits immunised with virions (Ad4p, Ad5v, Ad11p and Ad17) were used in a 1:200 dilution (Wadell, G., J. Immunol., 108, 622-632, 1972). The cells were then washed 2×5 min in PBS and incubated with the secondary antibody, a FITC conjugated swine-anti rabbit immunoglobulin G (DAKO), diluted 1:40 in PBS for 30 min at room temperature. The cells were washed again in PBS and then mounted with 80% glycerol in PBS and a coverslip. The photos were taken in a fluorescence microscope (Zeiss Axiovert) at 200× enlargement.

2. Results Concerning Binding to Cells of Neural Origin 2.1. FACS

Ad11p is binding very well to all of the cell lines used. 1 µg seems to be enough to saturate the 1 million cells except for the medulloblastoma cell line PFSK-1. One µg and 6 µg of Ad11p virions could label 76% and 86% of the PFSK-1 cells respectively. Ad17 is binding better to the PFSK-1 and A549 cells than to the other cell lines. In conclusion, Ad17 can bind to all of the cell lines, but not to the same extent as Ad11p. See FIG. 1.

2.2. [$^{35}$S]Methionine-Cysteine Labelling

Figure 2:
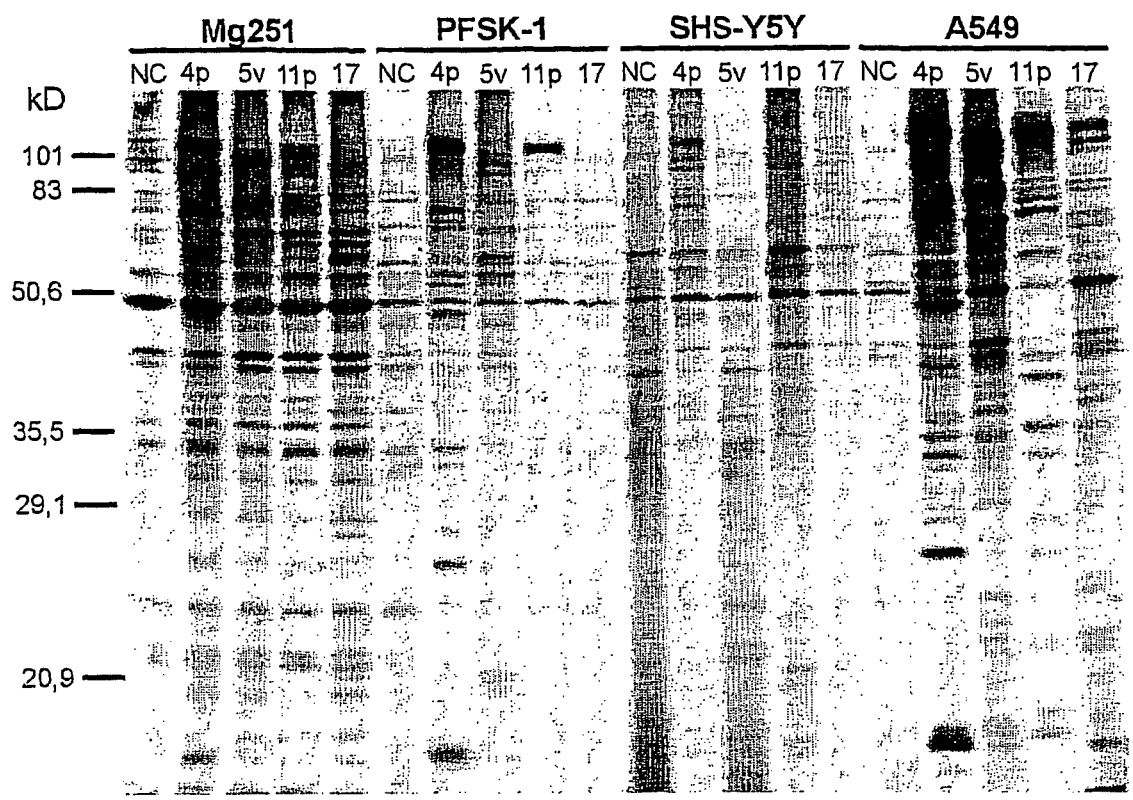
FIG. 2 shows the 12% SDS-PAGE with [$^{35}$S]methionine labelled proteins in virus infected neural cells. NC denotes the negative control (non-infected cells).

See FIG. 2: 12% SDS-PAGE with the [$^{35}$S]methionine labelled proteins. NC is negative control (non-infected cells).

Ad4p: Ad4p can be expressed in all cell lines. There is a strong protein band around 110 kD most likely representing the hexon protein. The viral polypeptides V and VI (48 and 24.5 kD, respectively, see table 1) seem to be strongly expressed in the A549 cells and also in PFSK-1. The cellular protein bands seems to be mostly unaffected, even if a small change in the level of cellular proteins can be detected compared to the control. Ad4p is the only virus type that can induce expression of virion proteins in the neuroblastoma cell line (SHS-Y5Y) even if the level of expression is significantly lower than in the other cell lines.

Ad5v: The Ad5v hexon is only expressed in the Mg251 and A549 cell line. Thus, only the glial cells of the neural cell types could support expression of Ad5v. Both cell lines show a strong expression of hexons as well as of other viral proteins.

Ad11p: Ad11p hexon is expressed in both the glioblastoma (Mg251) and the medulloblastoma cell line (PFSK-1) as well as in the epithelial cell line (A549). It is however interesting to see that some SHS-Y5Y bands are different compared to the control. A cellular band around 42 kD (probably the actin band) seems to be markedly decreased.

Ad17: Ad17 is expressed in the A549 cell line. The expression is not as strong as for the other virus types. However, neither hexon nor any other viral proteins are expressed in the neural cell lines.

TABLE 1

Characterised virion proteins
(Wadell, G., Hammarskjöld M-L., Winberg G.,
Varsanyi T. M., Sundell G. Annals of the New
York academy of sciences 354; 16-42, 1980.).

| Viral polypeptide | Ad4p kD | Ad5v kD | Ad11p kD | Ad17 kD |
|---|---|---|---|---|
| II (hexon) | 121 (117, 124) | 110 | 120 | 117 |
| III, IIIa, IV | 74, 72, 66 | 85, 66, 64 | 74, 70, 66 | 64, 62, 40 |
| V | 48 | 48.5 | 54 | 50.5 |
| VI | 24.5 | 24 | 24 | 23.2 |
| VII | 18 | 18.5 | 18 | 18.2 |
| VIII, IX | 11.8 | 13, 12 | 13, 12.5 | 11.7 |

2.3. Immunofluorescence

Ad4p: Virus specific staining in the Mg251 cells was detected already after 24 h p.i. and strong immunofluorescence after 48 h in both Mg251 and PFSK-1. SHS-Y5Y cells show no signs of infection at 48 h, but are strongly stained after 5 days p.i.

Ad5v: The Ad5v infected cells manifested weak virus specific immunofluorescence in the Mg251 cells after 48 h. Only a few PFSK-1 cells show a very strong expression after 48 h. SHS-Y5Y cells are not positive at 48 h, but have developed expression at 5 days.

Ad11p: There are some weakly positive cells at 24 h both in the Mg251 cells and the PFSK-1 cells. At 48 h and 5 days there is a strong viral expression. The SHS-Y5Y cells do not show any expression until 5 days p.i.

Ad17: There is a weak expression at 24 h p.i. that continues to be weak at 5 days p.i. in the Mg251 cells. Some of the PFSK-1 cells show strong expression at 5 days p.i., but the percentage of positive cells is low. SHS-Y5Y cells are positive at 5 days p.i.

3. Endothelial and Carcinoma Cells 3.1 Viruses Tested for Tropism for Endothelial and Carcinoma Cells Ad31p (prototype, 1315/63), Ad11p (Slobitski), Ad5v (vector strain, pFG140), Ad37p (GW), Ad4p (Ri-67) and Ad41p (tak) were used in this study and as representatives of adenoviral subgenera A, B, C, D, E and F. All serotypes were raised in A549 cells and purified by equilibrium centrifugation in CsCl. They were all typed with respect to their restriction pattern (Adrian et al., DNA restriction analysis of adenovirus prototypes 1 to 41., Arch. Virol. 91:277-290 (1986)).

3.2 Cell Lines and Culture Conditions

Eight human cell lines were used in this study. A549, from human oat cell carcinoma of the lung; HepG2, established from hepatoblastoma; HEP2, from larynx carcinoma; LNCaP and DU145 were both raised from metastatic prostate carcinoma; MG7 and CAMA, both from breast carcinoma. HMEC was an immortalised human microvascular endothelial cell line (Ades et al., J. Invest. Dermatol. 99:683-690 (1992)). A549, HepG2 and HEP2 cells were grown in DMEM containing 5%, 10% and 15% foetal calf serum (FCS) respectively, 2 mM HEPES, 0.75 g/l NaCO3 and 1× penicillin G (100 IU/ml)/streptomycin sulphate (100 μg/mnl) (PEST) at 37° C. These three cell lines were subcultured every 3 days.

LNCaP, DU145, CAMA and MG7 cells were all grown on RPMI 1640 containing 10% FCS, 20 mM HEPES, 0.75 g/l NaCO3, 1×PEST, with additional 10E-10 M methyltrienolene (NEN™ from Life Science Products) for LNCaP, 1 mM pyruvate and 2 mM glutamine for DU145 and 0.2 IE/1 ml insulin (Pharmacia & Upjohn AB) for MG7 at 37° C.

HMEC cells were grown in endothelial basal medium MCDB131 containing 10% dialysed FCS, 1×PEST, 2 μM hydrocortisone, 5 ng/ml human epidermal cell growth factor (HEGF) (Roche) and 2 mM glutamine. These five cell lines were subcultured every 5-7 days. For all the cell lines, the FCS concentration was decreased to 2% after virus infection.

3.3 Virus Labelling

The virions were labelled as described under 1.3. and frozen in glycerol (10% v/v) and kept at −70° C. until use.

3.4 Binding Experiments Using a FACScan Flow Cytometer

For each binding experiment 125 000-250 000 cells were used. The cells were incubated with 3 different concentrations, 1, 3 and 6 pg/cell, of biotinylated Ad 11p, Ad 5v, Ad 4p, Ad 31p, Ad 37p and Ad 41p virons in PBS containing 2% FCS and 0.01% $NaN_3$ (PBS—FCS—$NaN_3$) in a total volume of 100 μl at 4° C. on shaking for 30 min. The cells were washed once with 120 μl PBS—FCS—$NaN_3$ buffer, followed by addition of 1:100 dilution of streptavidin-fluoroscein isotiocyanate (DAKO) in PBS—FCS—$NaN_3$ buffer by shaking for another 30 min at 4° C. Then the cells were washed once again with the buffer described above and finally resuspended in 300 μl PBS—FCS—$NaN_3$ buffer containing 1 μg/ml propidium iodine (PI) to exclude dead cells from the fluorescence-activated cell sorting (FACS) analysis. The cell samples were measured by a FACScan (Becton Dickinson) flow cytometer and then analysed exploring the LYSYSII software (Becton Dickinson).

3.5 Immunofluorescence Procedures 200 000 cells of HepG2, HMEC and MG7 cell lines were stained as described under 1.6 above.

3.6 [$^{35}S$] Labelling of Infected Cell Proteins

One and a half million cells of HMEC, MG7, HepG2 and A549 were infected with 2 pg/cell (corresponding to 7200 virus particles/cell) of Ad 5v, Ad 11p and Ad 4p virions. In 1 ml medium without FCS, DMEM for A549 and HepG2 cells, RPMI 1640 for MG7 and HMEC cells, virions were absorbed by shaking the cell culture during 90 min, unbound viruses were then washed off with PBS. The infected cell cultures were washed once with methionine and cystein free RPMI medium 22 hours p.i. and incubated for 2 h in 2.5 ml methionine and cystein free DMEM (ICN Biomedicals, Inc.) or RPMI 1640 (ICN Biomedicals, Inc.) containing 5% FCS, 20 mM HEPES and. 1×PEST, to deplete endogenous methionine and cysteine. Twenty-four hours p.i., the cells were labelled with 0.45 mCi/bottle of 35S-labelled methionine and cysteine (1175 Ci/mmol, 10.5 mCi/ml; ICN). Fifty μl of cold cystein (100 mM) and 25 μl cold methionine (100 mM) was added 1 and 4.5 hours after labelling. After labelling for 24 hours both cold methionine and cysteine was added again. The infected cells were harvested 72 h p.i. and washed twice in 0.1 M Tris-HCl (pH 8.0)—4 mM EDTA—1 mM phenylmethylsulfonyl fluoride (PMSF) and resuspended in 90 μl of the same buffer (the final volumes were 100 μl). Then the samples were analysed by SDS-PAGE and autoradiography as described below.

3.7 SDS-PAGE and Autoradiography

Ten μl of each labelled sample was taken for electrophoresis by sodium dodecyl sulphate (SDS) polyacrylamide gel containing 12% acrylamide:bisacrylamide at a ratio of 29:1. The protein samples were mixed with equal volume of 2 × loading buffer and heated at 95° C. for 8 min before loading. The electrophoresis was performed at 200 volts for 3.5 h until the BPB dye reached the bottom of the gel. Then the gels were stained in coomassie brilliant blue for 3-5 hours and destained in 40% menthol and 10% acetic acid for 12-16 hours. The gels were dried using a gel drier (SAVANT) prior to autoradiography. The photographic film (Fuji-RX) was exposed for 1-3 days. The density of bands for hexon was analysed in a Gel-Pro ANALYSER program.

3.8 Titration of Viral Infectivity

HepG2, MG7, HMEC and A549 cells were analysed. 100 000 cells of each cell line were incubated with Ad 4p (0.2 pg/cell) in duplicate tubes for 1, 12, 24, 48, and 96 hours. After 1 h of adsorption in 200 μl of DMEM or RPMI 1640 containing 2% FCS on shaldng at 37° C., all cells were washed twice in PBS and then cultured in 1 ml fresh medium. Two tubes of infected cells were pooled together at the end of the incubation and freeze-thawed three times. The lysates were diluted in 10-fold steps, inoculated in five parallel A549 cell tubes for each dilution. The cytopathic effect was monitored every second day for 12 days.

4. Results Concerning Binding to Endothelial and Carcinoma Cells

Figure 3:
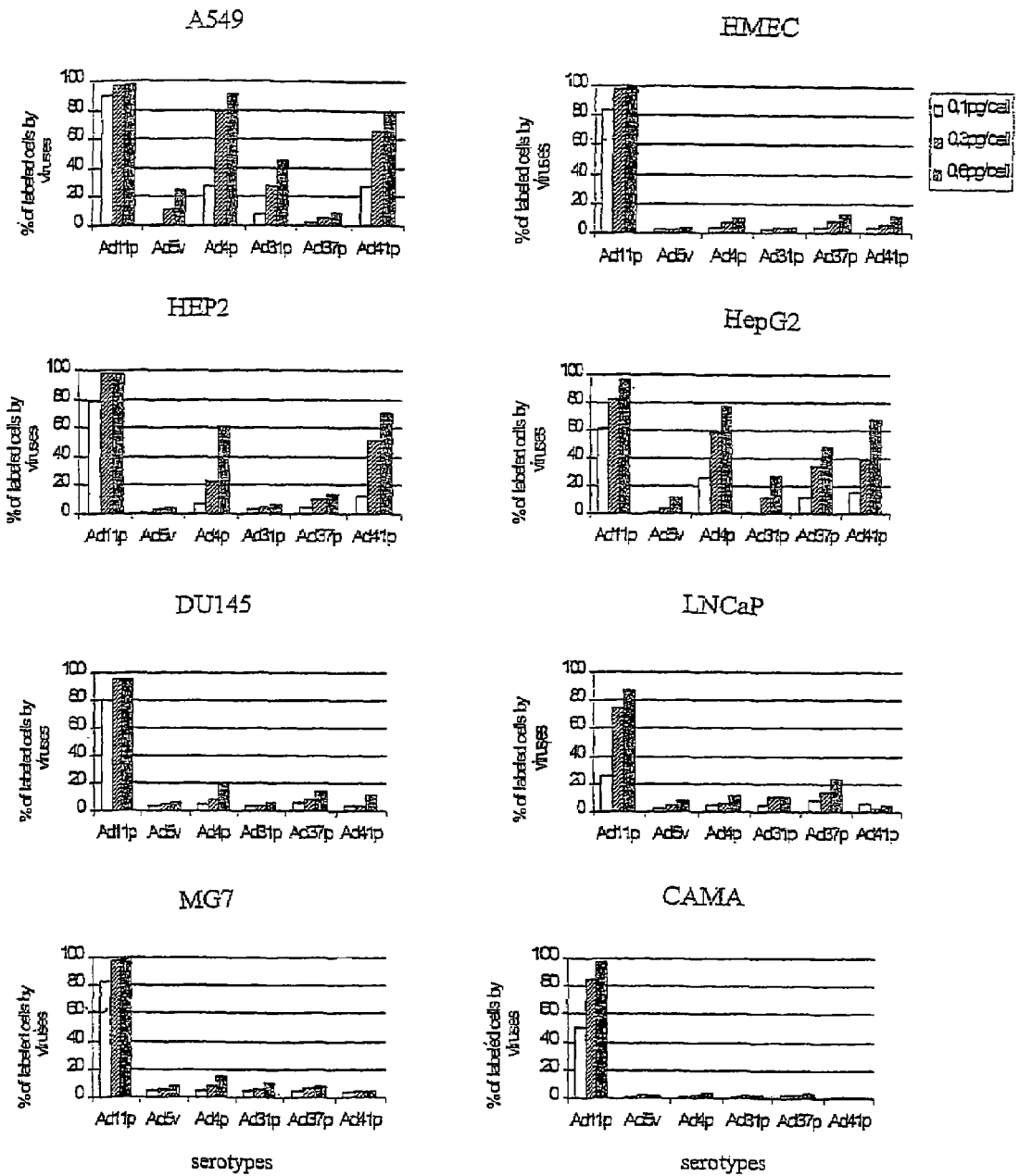
FIG. 3 shows the result of analysis of the binding capacity of Ad11p, Ad5v, Ad4p, Ad31p, Ad37p and Ad41p to endothelial cell line (HMEC, top right diagram), tumour cell lines A549 (a lung cancer cell line, top left diagram), HepG2 (hepatoma, second column, second line), LNCaP and DU145 (prostate carcinoma, third line, second and first column), CAMA and MG7 (breast carcinoma, fourth line, second and first column) and HEP2 (larynx carcinoma, second line, first column). Three-different concentrations of biotin-streptavidin-FITC labelled adenoviruses (0.1, 0.3 and 0.6 pg/cell) were incubated with cells of different origin, percentages of virus labelled cells were evaluated by flow cytometry. The values in the diagrams represent the means of three independent experiments.

Ad 11p showed markedly higher binding to the endothelial cell line and to all carcinoma cell lines studied than all other studied adenoviruses. See FIG. 3.

At the lowest virus concentration of 1 pg/cell, the labelled cells varied from 25% to over 80% in these cell lines, lowest in LNCaP cells with 25% labelled cells, highest in HMEC and DU145 cells with over 80% cells labelled by Ad11p. At a concentration of 6 pg/cell, Ad 11p virion labelled were more than 95% of HepG2, HEP2, MG7, CAMA, DU145 and HMEC cells, and over 85% of the LNCAP cells. However, Ad 5v displayed a low binding capacity to all investigated cell lines. Even at a high concentration of 6 pg virions /cell, Ad5v did not label more than 15% of the cells in any studied cell line.

It was also shown that Ad 4p shows preferential binding affinity to HepG2 and HEP2 cell lines. At a virus concentration of 6 pg/cell, Ad 4p virions could bind to 77% of HepG2 cells and 61% of HEP2 cells. They were much more efficient than Ad 5v (11% for HepG2 and 5% for HEP2), Ad 31p (27% and about 10%), Ad 37p (47% and 13%) and Ad 41p (68% and 71%), but still less efficient than Ad 11p (96% and 97%).

It was further shown, that Ad 4p and Ad 11p were more infectious than Ad 5v in hepatoma, breast cancer and endothelial cells. No sign of Ad 5v infection was noted in the breast cancer (MG7) cells.

The experiments also showed, that Ad4 p and Ad 11p viral structures and non-structural proteins were efficiently expressed in HepG2 and MG7 cell lines. Two fold more Ad 11p and Ad 4p hexons than Ad 5 hexons were produced in A549 cells, which also is in agreement with their differences in binding affinity. In MG7 cells, viral proteins were detected using Ad 11p and Ad 4p but not in Ad 5v infected cells. The efficient shut-off of the cellular proteins as a consequence of the efficient infections was seen in Ad 11p and Ad 4p but not Ad 5v infected A549 and MG7 cells. It was remarkable that the Ad 4p proteins were more efficiently expressed than the Ad 11p proteins in HepG2 and MG7 cells, even though Ad11p manifested a higher binding efficiency to these cells. See FIGS. 4 and 5.

The results show that Ad 11p from subgenus B:2 exhibits an impressive high binding efficiency for all cell lines tested, including the endothelial cell line and hepatoma, breast cancer, prostate cancer and larynx cancer cell lines. A high binding affinity of Ad 11 p to several hematopoietic cell lines has also been observed. Adenoviruses of subgenus B use a different unknown primary receptor.

5. Dendritic Cells 5.1 Virus Purification

Ad 5v, Ad 11p and Ad 35p were all raised and purified in A549 cells as follows:

A549 cells were grown in Dulbecco's modified Eagle medium (DMEM, Sigma) containing 5% foetal bovine serum (FBS), 20 mM HEPES, NaHCO$_3$ (0.75 g/l) and 1× penicillin G (100 IU/ml)-streptomycin sulphate (100 µg/ml)(PEST) at 37oC. Upon virus infection the FBS concentration was lowered to 1%. After virus was added to the cells, they were incubated at 37oC. on a rocker platform for 5 days. Thereafter the medium was removed and the cells resuspended in 0.01 M Tris-HCl pH 7.5. To break the cells they were frozen and thawed three times. An equal volume Arclon was added and the suspension shaken vigorously for 15 min. Finally the virus particles were separated on a discontinuous CsCl gradient (1.5 ml of 1.37 g/ml, 2 ml of 1.32 g/ml and 3 ml of 1.27 g/ml) by centrifugation at 100 000×g for 2.5 h. The buffer was changed to 0.05 M NaHCO$_3$, 0.135 M NaCl pH 8.8 on a nap-10 column, according to instructions by the manufacturer (Amersham Pharmacia Biotech).

5.2 Achieving Dendritic Cells

Human blood was collected from a healthy volunteer after 5 days of granulocyte-colony stimulating factor (G-CSF) subcutaneous injections (0.48 mg/injection). CD34+ cells were purified from the blood using magnetic activated cell sorter (MACS) with monoclonal anti-CD34 according to manufacturers description (Dynabead). To differentiate the CD34+ cells into dendritic cells (DC), cells were grown in 24-well plates at a concentration of 200 000 cells/well in 5% CO2 at 37° C. RPMI 1640 (Sigma) medium was used supplemented with 2.5×10E-8 M mercaptoethanol, 1×PEST, 2 mM L-glutamine, 10% heat inactivated FBS, 100 ng/ml granulocyte macrophage colony stimulating factor (GM-CSF) and 2.5 ng/ml tumour necrosis factor (TNF)-alpha. Interleukin (IL)-4 was added at a concentration of 50 ng/ml after 8-12 days. All recombinant human cytokines were purchased from R&D systems. The cells were split every 4-8 days.

5.3 Binding Studies Using FACScan Flow Cytometer

Cells were harvested after 16-19 days and kept in 1×PBS containing 2% FBS (heat inactivated). 10E6 cells were used in each reaction. Biotinylated Ad5v, 11p or 35p virions were added to the cells at a concentration of 10 500 virions/cell and allowed to bind for 30 min. The remaining method was as described under 1.4 above and the result evaluated using the CellQuest software (Becton Dickinson).

5.4 Studying Uptake of Virions by Immunohistochemistry 1.7×10E5 cells were used for each experiment. Cells grown for 18-22 days were infected with Ad5v, 11p or 35p at a concentration of 7000 virions/cell and further incubated at 37° C., 5% CO$_2$ for 1, 24 or 49 h. The cells were washed in 1 ml 1×PBS and put on a Super Frost glass slide (Menzel-Gläser) to dry over night. The cells were fixed in ice-cold 70% acetone, 30% methanol for 10 min followed by blocking with 5% human serum for 1 h at 37° C. The primary mouse anti-human CD1a antibody (Dako) was diluted 1:100 in 1×PBS containing 0.1% BSA (PBS—BSA). Unfractionated serum from rabbits immunised with whole virions (Ad5v, 11p and 35p) was diluted 1:200 and used as primary antibody against viral structural proteins. The cells were incubated with the primary antibodies for 1 h at 37° C. followed by washing in PBS 3×5 min. The secondary antibodies (tetramethyl-rhodamine-6-isothiocyanate (TRITC)-conjugated goat anti-mouse and FITC-conjugated swine anti-rabbit) were diluted 1:40 in PBS—BSA and incubated at 37° C. for 30 min and washed as before. 50% glycerol in 1×PBS was added to store the cells. The stainings were evaluated using a light microscope (Zeiss) and confocal microscope (Molecular probe 2001 by Molecular Dynamics). Pictures scanned in confocal microscope were processed using the software program Image Space (Molecular Dynamics).

Figure 6:
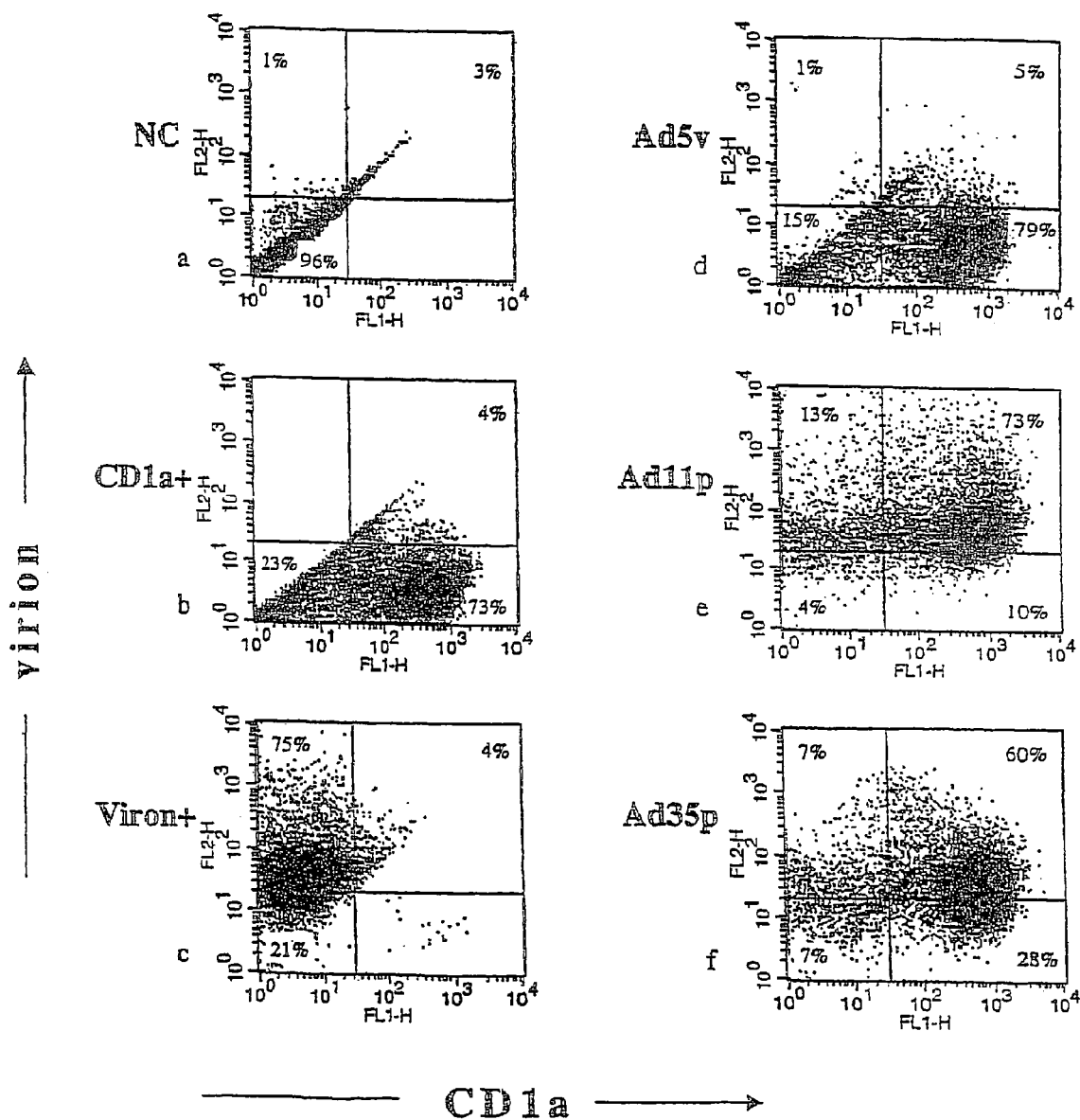
FIG. 6 shows the result of the FACS analysis of virus binding (Ad 5v, Ad 11p and Ad 35p) to dendritic cells.
Figure 7:
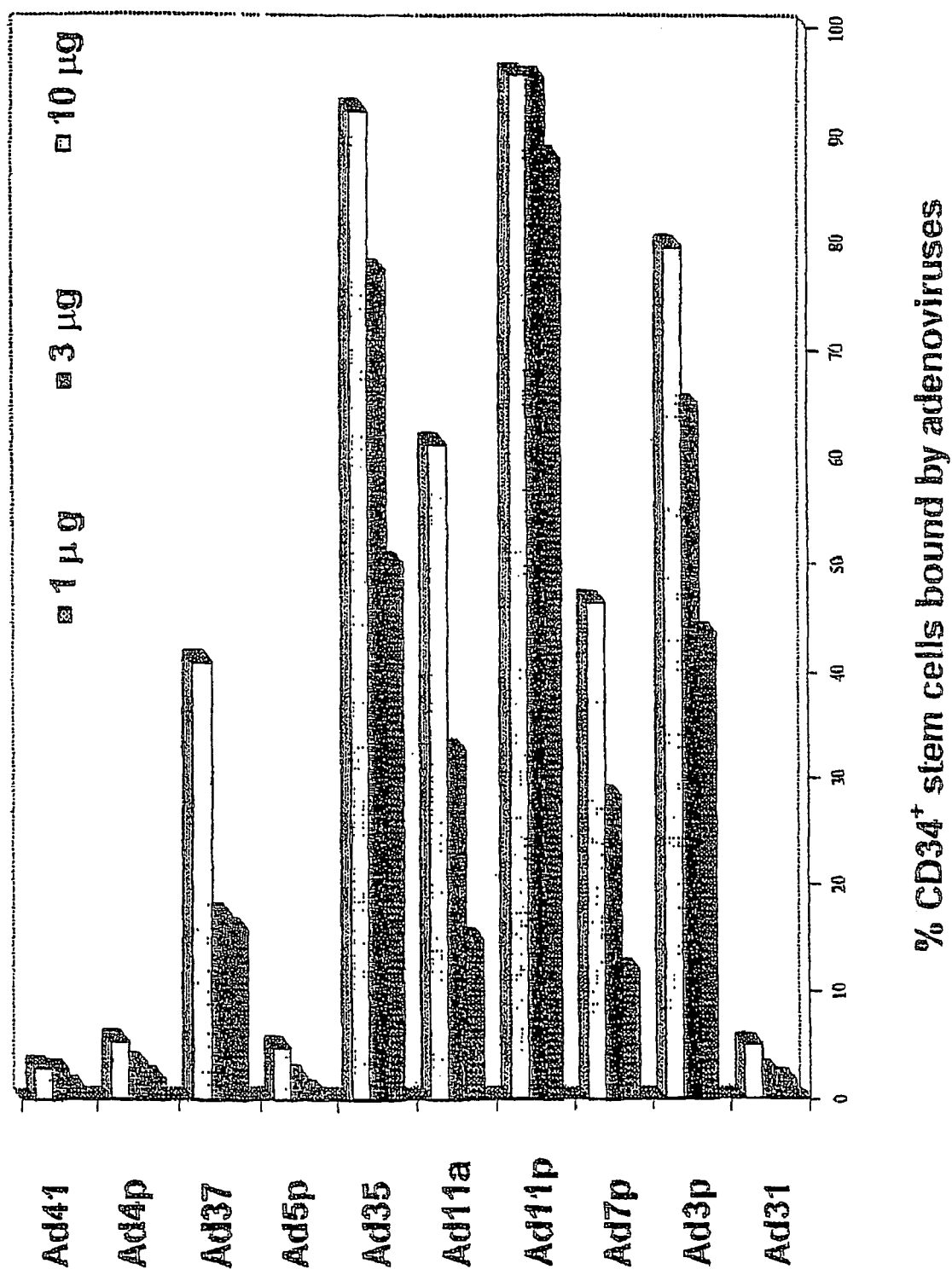
FIG. 7 shows the result of FACS analysis evaluating the binding capacities of adenoviruses with various tropisms to CD34+ progenitor cells from bone marrow.
Figure 8:
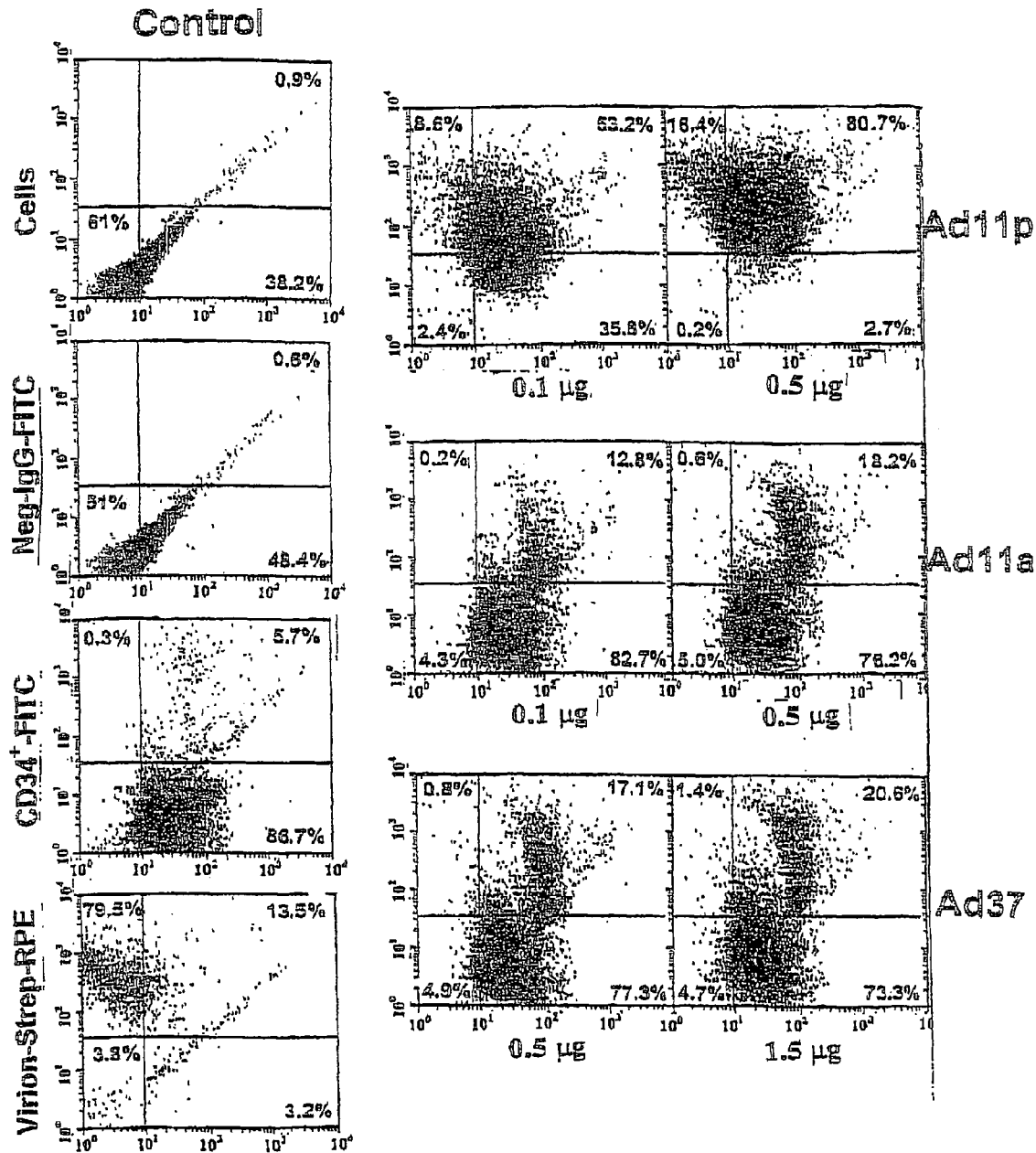
FIG. 8 shows the result of a FACS analysis using streptavidin RPE labelled virions, confirming that the cells binding adenoviruses represent CD34+ cells.

6. Results Concerning the Binding of Adenovirions to and Internalisation into Dendritic Cells Ad 11p exhibited high binding efficiency to CD1a dendritic cells, in particular in comparison to the conventionally used Ad 5v. See FIG. 6. Viral uptake and intranuclear expression was confirmed by confocal microscopy. No uptake was observed in parallel studies using the Ad5 vector.

Figure 4:
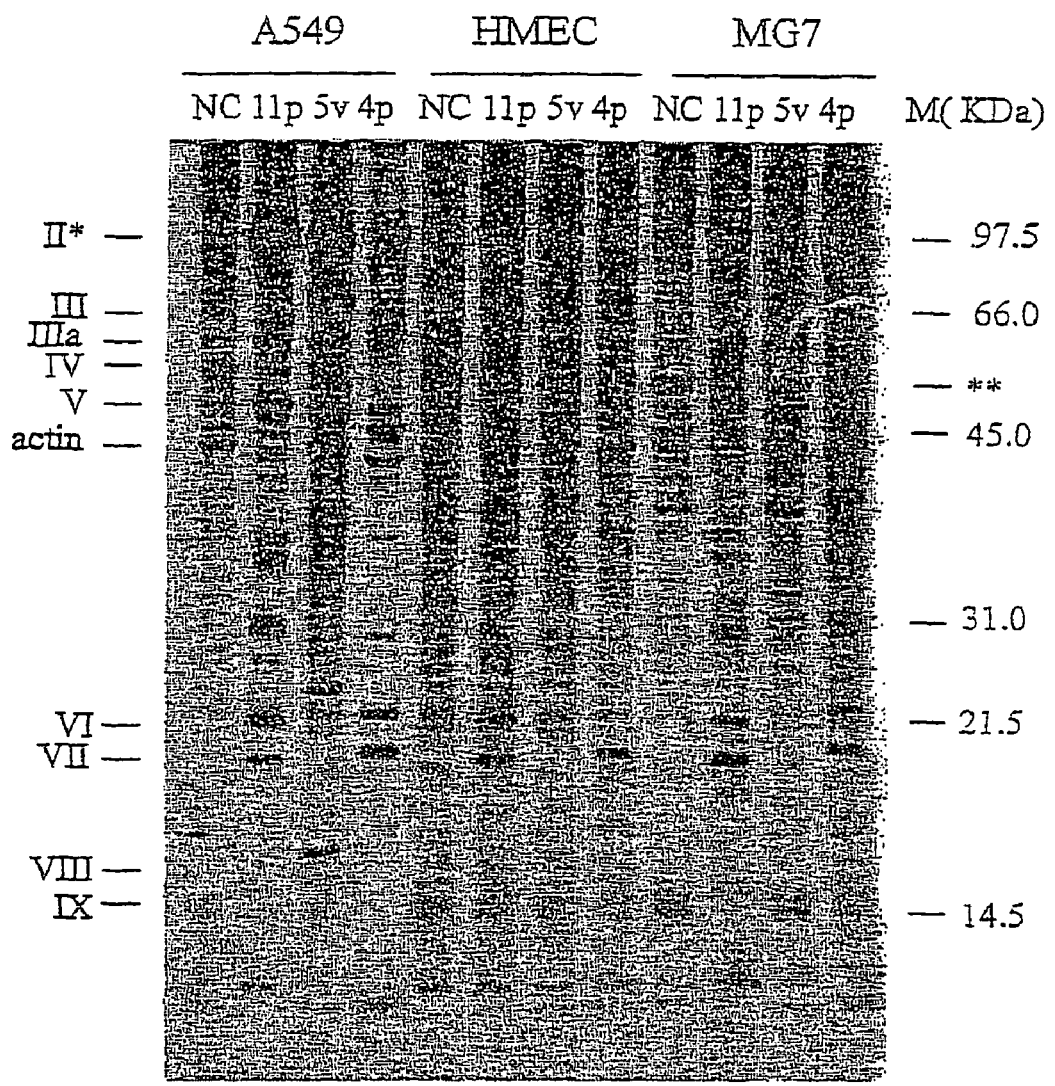
FIG. 4 shows the expression of viral structural and nonstructural proteins in the HMEC, MG7 and A549 cell lines. One and a half million cells of the different cell lines were infected by Ad11p, Ad5v and Ad4p (7200 viral physical particles/cell) and labelled with $^{35}$S-labelled methionine and cystein 24 h p.i. and harvested 72 h p.i. The same amount of cell lysates from different cell lines were separated by SDS-PAGE on a 12% gel and autoradiographed for 1-3 days. The arrows show the main structural polypeptides of Ad11p.
Figure 5:
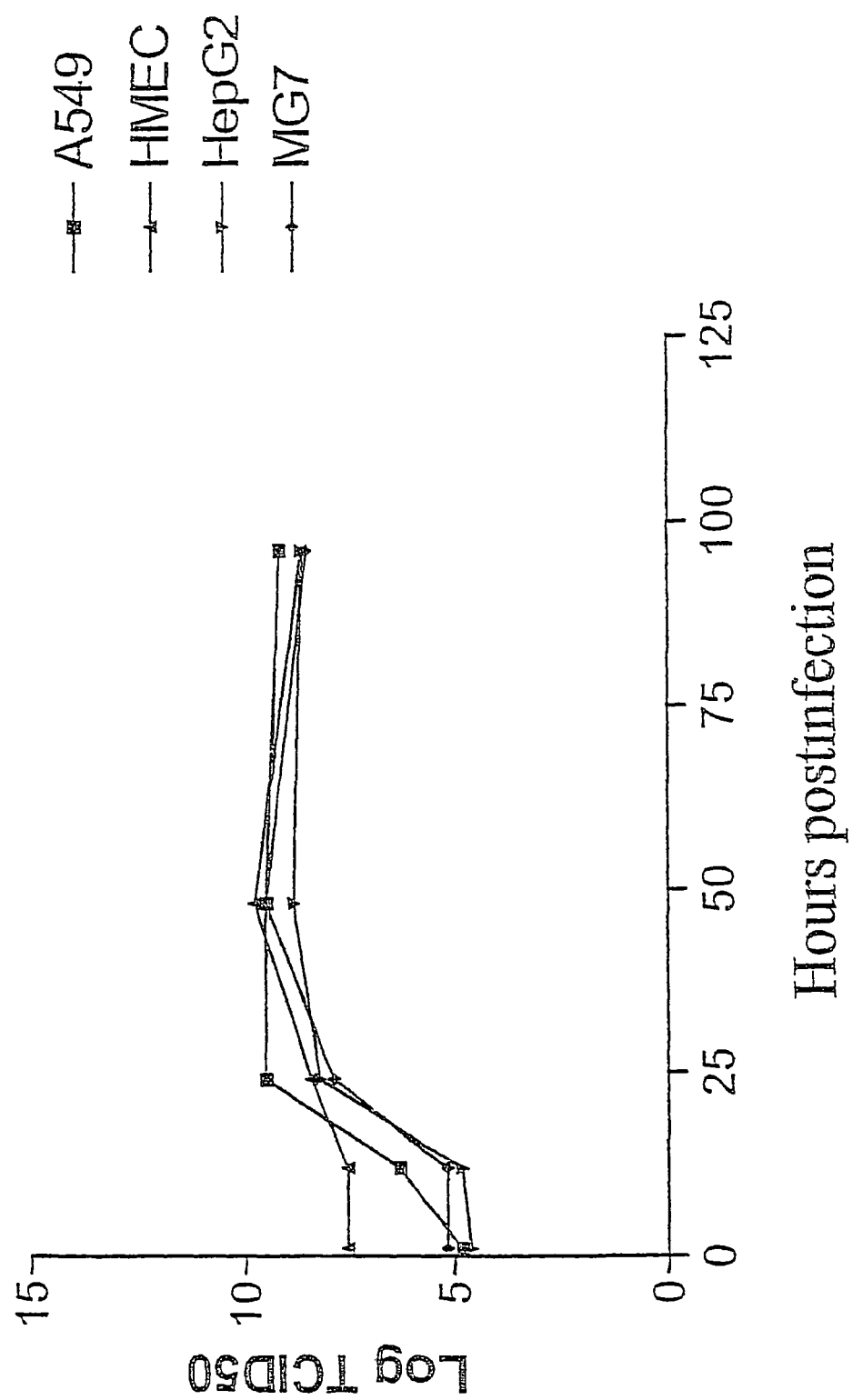
FIG. 5 shows the production of infectious Ad4p virus particles in HMEC, HepG2, MG7 and A549 cells (as a reference). 100 000 cells of the HNMC, HepG2, MG7 and A549 cell line were infected by Ad4p (0.2 pg/cell) and incubated for 1, 12, 24, 48 and 96 h The infected cells were freeze-thawed three times and the TCID$_{50}$ of the lysates determined by titration in A549 cells.

7. Results Concerning the Binding of Adenoviruses to Hematopoietic Progenitor Cells 7.1. Adenoviruses Belonging to Six Subgenera Manifested Different Binding Affinity to Hematopoietic Progenitor Cells The character of the hematopoietic progenitor cells surface components to which adenoviruses from six subgenera attach were investigated using a virus-binding assay, in which cells were freshly prepared using immunomagnetic beads (Dynal) coupled with mouse anti-human CD34+ monoclone antibody and incubated at 4° C. with biotinylated viruses and then streptavidin-FICT, and the amount of virus bound to the cell surface was quantified by FACS analysis. The binding capacities of adenoviruses with various tropisms to CD34+ progenitor cells from bone marrow are illustrated in FIG. 4, which represents one of three repeated observations.

The fluorescence histogram of adenoviruses manifests various binding affinity to CD34+ cells that can be classified into three groups; high, intermediate, and undetectable affinity. Virions of Ad3, Ad11p, and Ad35p displayed high binding affinity, i.e. with 1 µg of labelled virions, more than 90% of positive cells were detected for Ad11p, whereas about 50% were labelled for both Ad3 and Ad35. The Ad7, Ad11a, and Ad37 manifested an intermediate affinity to CD34+ cells, i.e. 20% cell scored positive with 1 µg of added virions. Virions of Ad31, Ad5, Ad4, and Ad41 manifested no detectable affinity to the stem cells 1, 3 and 10 µg of the virions were used per 1 million CD34+ cells.

7.2 Confirmation that the Cells Binding Adenoviruses Represent CD34+ Cells. Identification of CD34+ Cells Bound by Some Adenovirus Serotypes.

Freshly purified CD34+ cells were incubated with biotinylated ADVs at 4° C. for 30 min, the cells were washed once with PBS-FCS-NaN$_3$ buffer, and then simultaneously incubated with RPE-avidin and MAB-FITC specific for CD34+ cells, and submitted to flow cytometric analysis. The cells bound by ADVs showed Red-fluorescence (upper left). Green-fluorescence indicated the CD34+ cells (lower right). Double labelled cells showed intensities in the upper right window. See FIG. 5.

At the concentration 0.1 µg of Ad11p virions, the double labelled positive cells (CD34+ marker with fluorescence staining and virion marker with RPE staining) corresponded to 53.2% of total cells for Ad11p attachment. Comparison with Ad11p, Ad11a, and Ad37 showed a similar low affinity that was only 12.8% or 17.1% cells double labelling positive. By increasing the amount of virions, the portion of Ad11p labelled cells with double colour apparently increased to 80.7%, but only reached 18.2% for Ad11a and 20.6% for Ad37. Consequently, the cells bound by adenoviruses were interpreted to represent quiescent CD34+ cells.

8. Determination of the Ad11p Nucleotide and Amino Acid Sequence

The nucleic acid sequence and the preliminary amino acid sequence is attached as SEQ. ID. NO. 1 and SEQ. ID. NO. 2. A preliminary genomic analysis has been performed and the result is summarised in the table below:

TABLE 2

Adenovirus 11p genome

| Name of region | NA sequence and map unit | Size and % | Codon for ORF | Position of NA |
|---|---|---|---|---|
| ITR | 1-134 (0-0.38) | 134/0.38 | — | |
| E1A | 480-1530 (1.36-4.3 mu) | 1050/3.0 | 28K | 568-1161 |
| E1B | 1556-3949 (4.4-11.2 mu) | 2393/6.8 | 21K | 1610-2152 |
|  |  |  | 55K | 1915-3399 |
|  |  |  | Hexon associated protein IX | 3483-3902 |
| E2A | 23401-21845 (67.2-62.8 mu) | 1556/4.4 | DNA binding protein | 23401-21845 |
| E2B | 10342-3950 (29.7-11.4 mu) | 6392/18.4 | Protein IVa2 | 5588-3964 |
|  |  |  | DNA polymerase | 8435-5067 |
|  |  |  | Terminal protein | 10342-8438 |
| E3 | 26863-30633 (77.2-88 mu) | 3770/10.8 | 12.1K | 27184-27501 |
|  |  |  | 16.1K | 27455-27850 |
|  |  |  | 18.5K | 27835-28335 |
|  |  |  | 20.3K | 28355-28900 |
|  |  |  | 20.6K | 28918-29481 |
|  |  |  | 10.3K | 29525-29800 |
|  |  |  | 15.2K | 29805-30209 |
|  |  |  | 15.3K | 30202-30609 |
| IE | 5138-8255 (17.8-23.7) | 3117/9.0 | 11.5K | 6160-6480 |
|  |  |  | 15.3K agnoprotein | 7845-8255 |
| L1 | 10648-13602 (30.6-39.1 mu) | 2954/8.5 | 55K | 10648-11813 |
|  |  |  | IIIa protein | 11839-13602 |
| L2 | 13682-17314 (39.3-49.8 mu) | 3632/10.4 | Penton base | 13682-15367 |
|  |  |  | Protein VII | 15379-15957 |
|  |  |  | Protein V | 16000-17055 |
|  |  |  | 11K protein precursor | 17084-17314 |
| L3 | 17398-21766 (50-62.5 mu) | 4368/12.5 | Protein VI | 17398-18138 |
|  |  |  | Hexon | 18254-21100 |
|  |  |  | 23K proteinase | 21137-21766 |
| L4 | 23432-27184 (67.3-78.1 mu) | 3748/10.8 | 100K protein | 23432-25870 |
|  |  |  | 33K | 25602-26444 |
|  |  |  | VIII Hexon associated protein precursor | 26451-27184 |
| L5 | 30811-31788 (88.5-91.3 mu) | 975/2.8 | Fiber protein | 30811-31788 |
| ITR | 34659-34793 (99.6-100 mu) | 134/0.38 | — | |

Note:
NA, nucleotide.

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

The invention claimed is:

1. A purified and isolated DNA sequence comprising the nucleotide sequences defined by positions 30811-31788 and 18254-21100 in SEQ ID NO: 1.

2. An isolated and purified DNA sequence comprising the sequence of SEQ ID NO: 1.

3. A gene delivery vehicle comprising the sequence according to claim 2.

4. A vector comprising the sequence defined in claim 2.

5. The gene delivery vehicle of claim 3, wherein said vehicle further comprises a foreign nucleic acid capable of expressing in a human a therapeutic or prophylactic agent.

6. A method of gene therapy, comprising the step of administering a therapeutically effective amount of the gene delivery vehicle of claim 3 to a human in need thereof.

7. A method of gene therapy, comprising transfecting human cells of neural origin with the gene delivery vehicle according to claim 3.

8. A method of gene therapy, comprising transfecting human cells selected from the group consisting of hepatoma, breast cancer and endothelial cells with the gene delivery vehicle according to claim 3.

9. A method of gene therapy, comprising transfecting human dendritic cells with the gene delivery vehicle according to claim 3.

10. A method of gene therapy, comprising transfecting human endothelial cells with the gene delivery vehicle according to claim 3.

11. A method of gene therapy, comprising transfecting human hematopoietic progenitor cells with the gene delivery vehicle according to claim 3.

12. A method in the treatment of a patient having cancer, comprising the step of administering to the patient a therapeutically effective amount of the gene delivery vehicle of claim 3.

13. A method of gene therapy, comprising the step of administering a therapeutically effective amount of the gene delivery vehicle of claim 5 to a human in need thereof.

14. The method of claim 7, wherein said human cells are selected from the group consisting of glioblastoma, neuroblastoma and medulloblastoma cells.

15. The method of claim 12, wherein said cancer is selected from the group consisting of lung cancer, breast caner, prostate cancer, and bladder cancer.

* * * * *

(12) EX PARTE REEXAMINATION CERTIFICATE (10429th)
United States Patent
Wadell et al.

(10) Number: US 7,459,153 C1
(45) Certificate Issued: Dec. 10, 2014

(54) VIRAL VECTORS FOR GENE THERAPY

(76) Inventors: Göran Wadell, Umeå (SE); Ya-fang Mei, Umeå (SE); Anna Segerman, Umeå (SE); Johan Skog, Umeå (SE); Kristina Lindman, Umeå (SE)

Reexamination Request:
No. 90/012,556, Sep. 13, 2012

Reexamination Certificate for:
| | |
|---|---|
| Patent No.: | 7,459,153 |
| Issued: | Dec. 2, 2008 |
| Appl. No.: | 10/250,304 |
| Filed: | Jan. 23, 2004 |

(21) Appl. No.: 90/012,556

(22) PCT Filed: Jan. 4, 2002

(86) PCT No.: PCT/SE02/00013
§ 371 (c)(1),
(2), (4) Date: Jan. 23, 2004

(87) PCT Pub. No.: WO02/053759
PCT Pub. Date: Jul. 11, 2002

Related U.S. Application Data

(60) Provisional application No. 60/260,358, filed on Jan. 8, 2001.

(30) Foreign Application Priority Data

Jan. 4, 2001 (SE) .................................. 0100035

(51) Int. Cl.
*C12N 15/63* (2006.01)
*C12N 15/86* (2006.01)
*A61K 48/00* (2006.01)
*C07H 21/00* (2006.01)
*C07H 21/04* (2006.01)
*C12N 15/861* (2006.01)
*C07K 14/00* (2006.01)
*C07K 14/075* (2006.01)

(52) U.S. Cl.
CPC ...... *C12N 15/86* (2013.01); *C12N 2710/10345* (2013.01); *C12N 2710/10343* (2013.01); *C12N 2810/6018* (2013.01)
USPC ..... 424/93.2; 424/93.1; 424/93.6; 435/320.1; 536/23.1; 536/23.7; 536/23.72

(58) Field of Classification Search
None
See application file for complete search history.

(56) References Cited

To view the complete listing of prior art documents cited during the proceeding for Reexamination Control Number 90/012,556, please refer to the USPTO's public Patent Application Information Retrieval (PAIR) system under the Display References tab.

*Primary Examiner* — Johnny F Railey

(57) ABSTRACT

Adenovirus types 11p and 4p show a higher binding affinity and infectivity than type 5 for endothelial and carcinoma cell lines. Adenovirus type 11p shows a stronger binding to cells for neural origin, such as glioblastoma, neuroblastoma and medulloblastoma. The fact that adenovirus type 11 has a comparatively low prevalence in society, together with its high affinity and infectivity, makes it very suitable for use in gene therapy.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-15 are cancelled.

\* \* \* \* \*